(12) United States Patent
Meiyappan et al.

(10) Patent No.: US 9,708,590 B2
(45) Date of Patent: Jul. 18, 2017

(54) CRYSTAL STRUCTURE OF HUMAN α-N-ACETYLGLUCOSAMINIDASE

(71) Applicant: Shire Human Genetic Therapies, Inc., Lexington, MA (US)

(72) Inventors: Muthuraman Meiyappan, Jamaica Plain, MA (US); Michael F. Concino, Bolton, MA (US); Angela W. Norton, Reading, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

(21) Appl. No.: 14/120,882

(22) Filed: Jul. 7, 2014

(65) Prior Publication Data
US 2015/0031112 A1   Jan. 29, 2015

Related U.S. Application Data

(63) Continuation of application No. 13/136,092, filed on Jul. 22, 2011, now Pat. No. 8,775,146.
(Continued)

(51) Int. Cl.
*C12N 9/24*   (2006.01)
*C12Q 1/34*   (2006.01)
*G01N 33/573*   (2006.01)

(52) U.S. Cl.
CPC ............. *C12N 9/2402* (2013.01); *C12Q 1/34* (2013.01); *G01N 33/573* (2013.01);
(Continued)

(58) Field of Classification Search
CPC ...... C12N 9/2402; C12Q 1/34; G01N 33/573; G01N 2333/924; G01N 2500/00; C12Y 302/0105
See application file for complete search history.

(56) References Cited

U.S. PATENT DOCUMENTS 8,775,146 B2   7/2014   Meiyappan et al.
2008/0292642 A1*  11/2008  Borhani .......... A61K 39/39591
                                                           424/172.1

FOREIGN PATENT DOCUMENTS

WO   WO 97/19177 A1   5/1997
WO   WO 2004/041170 A2   5/2004
(Continued)

OTHER PUBLICATIONS

P54802 (last viewed on Aug. 26, 2015).*
(Continued)

*Primary Examiner* — Alexander Kim
(74) *Attorney, Agent, or Firm* — Wolf, Greenfield & Sacks, P.C.

(57) ABSTRACT

The present invention provides the three-dimensional structure of human α-N-acetylglucosaminidase (NAGLU) protein. This crystallographic information is useful in the identification and development of novel binding compounds of NAGLU, NAGLU mutants, for example, those associated with Sanfilippo syndrome type B (mucopolysaccharidosis III B (MPS III-B)), and other NAGLU family members (family 89 α-N-acetylglucosaminidase) which may modulate the activity and/or stability of mutated NAGLU. Such compounds may be useful for the treatment of Sanfilippo syndrome type B (mucopolysaccharidosis III B (MPS III-B)).

20 Claims, 19 Drawing Sheets

Related U.S. Application Data

(60) Provisional application No. 61/366,694, filed on Jul. 22, 2010.

(52) U.S. Cl.
CPC .. *C12Y 302/0105* (2013.01); *G01N 2333/924* (2013.01); *G01N 2500/00* (2013.01)

(56) References Cited

FOREIGN PATENT DOCUMENTS

| WO | WO 2009/131698 A2 | 10/2009 |
|---|---|---|
| WO | WO 2011/163652 A2 | 12/2011 |

OTHER PUBLICATIONS

John Kennedy (1986)., Carbohydrate Chmistry vol. 15 Part II, Whitstable Litho Ltd., p. 421.*
Chang et al., Glycoprotein Structural Genomics: Solving the Glycosylation Problem., Structure. (2007), vol. 15(3), pp. 267-273.*
McPherson et al., Review. Current approaches to Macromolecular crystallization., Eur. J. Biochem., (1990), vol. 189, p. 1-23.*
Weber, Overview of Crystallization Methods. Methods in Enzymology, 1997, vol. 276, pp. 13-22.*
Kundrot et al. (Cell. Mol. Life Sci. 2004, 61: 525-536.*
Cudney, Rigaku Journal, 1999, vol. 16, No. 1, pp. 1-7.*
Drenth et al., Principles of X-ray Crystallography, Springer, New York, 1999, pp. 1-21.*
Klyushnichenko, Protein crystallization: from HTS to kilogram-scale., Curr. Op. Drug Discovery, 2003, 6(6):848-54.*
Chayen, Turning protein crystallization from an art into a science., Current Opinion in Structural Biology, 2004, vol. 14, pp. 577-583.*
Yang et al., Crystalline monoclonal antibodies for subcutaneous delivery., PNAS Jun. 10, 2003, vol. 100, pp. 6934-6939.*
Tang et al., Effects of the silanized mica surface on protein crystallization, Acta Cryst (2005), vol. D61, pp. 53-59.*
Branden and Tooze, Introduction to Protein Structure (1999), 2nd edition, Garland Science Publisher, pp. 3-12.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Invitation to Pay Additional Fees, mailed Nov. 3, 2011 for Application No. PCT/US2011/045045.
International Search Report and Written Opinion, mailed Feb. 16, 2012 for Application No. PCT/US2011/045045.
International Preliminary Report on Patentability, mailed Jan. 22, 2013 for Application No. PCT/US2011/045045.
[No Author Listed], Glycoside Hydrolase Family 89. Carbohydrate Active Enzymes. http://www.cazy.org/GH89_all.html [last accessed Oct. 23, 2014]. 8 pages.
[No Author Listed], Grants Awarded in 2005: Dr. Matthew Ellinwood, Iowa State University, Department of Animal Sciences Ames, IA. "Therapy for MPS IIIB: Naglu Targeting to the CNS". 2005. http://www.mpssociety.org/wp-content/uploads/2011/07/2005-Research-Grants.pdf [last accessed Oct. 18, 2011]. 9 pages.
Amaral, Therapy through chaperones: sense or antisense? Cystic fibrosis as a model disease. J Inherit Metab Dis. Apr.-Jun. 2006;29(2-3):477-87. Review.
Asano et al., Therapeutic applications of sugar-mimicking glycosidase inhibitors. Mini Rev Med Chem. Jul. 2001;1(2):145-54. Review.
Asano, Glycosidase inhibitors: update and perspectives on practical use. Glycobiology. Oct. 2003;13(10):93R-104R. Epub Jul. 8, 2003.
Asano, Sugar-mimicking glycosidase inhibitors: bioactivity and application. Cell Mol Life Sci. May 2009;66(9):1479-92. doi: 10.1007/s00018-008-8522-3. Review.
Bartlett et al., CAVEAT: A program to facilitate the structure-derived design of biologically active molecules. Molecular Recognition in Chemical and Biological Problems. Royal Chem Soc. 1989;78:182-96.
Beer et al., Synthesis of 2-acetamido-2-deoxy-D-gluconhydroximolactone-derived and chitobionhydroximolactone-derived N-phenylcarbamates, potential inhibitors of beta-N-acetylglucosaminidase. Helv Chim Acta. 1990;73:1918-22.
Beesley et al., Identification of 12 novel mutations in the alpha-N-acetylglucosaminidase gene in 14 patients with Sanfilippo syndrome type B (mucopolysaccharidosis type IIIB). J Med Genet. Nov. 1998;35(11):910-4.
Beesley et al., Molecular defects in Sanfilippo syndrome type B (mucopolysaccharidosis IIIB). J Inherit Metab Dis. 2005;28(5):759-67.
Böhm, The computer program LUDI: a new method for the de novo design of enzyme inhibitors. J Comput Aided Mol Des. Feb. 1992;6(1):61-78.
Boraston et al., Carbohydrate-binding modules: fine-tuning polysaccharide recognition. Biochem J. Sep. 15, 2004;382(Pt 3):769-81.
Bricogne et al., Generation, representation and flow of phase information in structure determination: recent developments in and around SHARP 2.0. Acta Crystallogr D Biol Crystallogr. Nov. 2003;59(Pt 11):2023-30. Epub Oct. 23, 2003.
Brünger et al., Crystallography & NMR system: A new software suite for macromolecular structure determination. Acta Crystallogr D Biol Crystallogr. Sep. 1, 1998;54(Pt 5):905-21.
Brunger, Assessment of phase accuracy by cross validation: the free R value. Methods and applications. Acta Crystallogr D Biol Crystallogr. Jan. 1, 1993;49(Pt 1):24-36.
Buchan et al., tRNA properties help shape codon pair preferences in open reading frames. Nucleic Acids Res. Feb. 9, 2006;34(3):1015-27.
Bunge et al., Mucopolysaccharidosis type IIIB (Sanfilippo B): identification of 18 novel alpha-N-acetylglucosaminidase gene mutations. J Med Genet. Jan. 1999;36(1):28-31.
Bychkova et al., Folding intermediates are involved in genetic diseases? FEBS Lett. Feb. 6, 1995;359(1):6-8.
Chen et al., Facile synthesis of 2,4-dinitrophenyl alpha-D-glycopyranosides as chromogenic substrates for alpha-glycosidases. Chembiochem. May 7, 2007;8(7):719-22.
Cohen et al., Molecular modeling software and methods for medicinal chemistry. J Med Chem. Mar. 1990;33(3):883-94.
Collaborative Computational Project, No. 4. The CCP4 suite: programs for protein crystallography. Acta Crystallogr D Biol Crystallogr. Sep. 1, 1994;50(Pt 5):760-3.
Cowtan et al., Miscellaneous algorithms for density modification. Acta Crystallogr D Biol Crystallogr. Jul. 1, 1998;54(Pt 4):487-93.
Cressant et al., Improved behavior and neuropathology in the mouse model of Sanfilippo type IIIB disease after adeno-associated virus-mediated gene transfer in the striatum. J Neurosci. Nov. 10, 2004;24(45):10229-39.
Davies et al., Structures and mechanisms of glycosyl hydrolases. Structure. Sep. 15, 1995;3(9):853-9.
Di Domenico et al., Intracranial gene delivery of LV-NAGLU vector corrects neuropathology in murine MPS IIIB. Am J Med Genet A. Jun. 2009;149A(6):1209-18.
Di Natale et al., Biosynthesis of alpha-N-acetylglucosaminidase in cultured human kidney carcinoma cells. Enzyme. 1985;33(2):75-83.
Di Natale et al., Treatment of the mouse model of mucopolysaccharidosis type IIIB with lentiviral-NAGLU vector. Biochem J. Jun. 1, 2005;388(Pt 2):639-46.
Ellgaard et al., Setting the standards: quality control in the secretory pathway. Science. Dec. 3, 1999;286(5446):1882-8. Review.
Ellinwood et al., A model of mucopolysaccharidosis IIIB (Sanfilippo syndrome type IIIB): N-acetyl-alpha-D-glucosaminidase deficiency in Schipperke dogs. J Inherit Metab Dis. 2003;26(5):489-504.

(56) References Cited

OTHER PUBLICATIONS

Emre et al., Sanfilippo syndrome in Turkey: Identification of novel mutations in subtypes A and B. Hum Mutat. Feb. 2002;19(2):184-5.
Emsley et al., Coot: model-building tools for molecular graphics. Acta Crystallogr D Biol Crystallogr. Dec. 2004;60(Pt 12 Pt 1):2126-32. Epub Nov. 26, 2004.
Fan et al., Accelerated transport and maturation of lysosomal alpha-galactosidase A in Fabry lymphoblasts by an enzyme inhibitor. Nat Med. Jan. 1999;5(1):112-5.
Fan, A counterintuitive approach to treat enzyme deficiencies: use of enzyme inhibitors for restoring mutant enzyme activity. Biol Chem. Jan. 2008;389(1):1-11. Review.
Ficko-Blean et al., Structural and mechanistic insight into the basis of mucopolysaccharidosis IIIB. Proc Natl Acad Sci U S A. May 6, 2008;105(18):6560-5. doi: 10.1073/pnas.0711491105. Epub Apr. 28, 2008.
Ficko-Blean et al., The interaction of a carbohydrate-binding module from a Clostridium perfringens N-acetyl-beta-hexosaminidase with its carbohydrate receptor. J Biol Chem. Dec. 8, 2006;281(49):37748-57. Epub Sep. 21, 2006.
Fu et al., Neurological correction of lysosomal storage in a mucopolysaccharidosis IIIB mouse model by adeno-associated virus-mediated gene delivery. Mol Ther. Jan. 2002;5(1):42-9.
Gething et al., Protein folding in the cell. Nature. Jan. 2, 1992;355(6355):33-45. Review.
Good et al., Hydrogen ion buffers for biological research. Biochemistry. Feb. 1966;5(2):467-77.
Goodford et al., A computational procedure for determining energetically favorable binding sites on biologically important macromolecules. J Med Chem. Jul. 1985;28(7):849-57.
Goodsell et al., Automated docking of substrates to proteins by simulated annealing. Proteins. 1990;8(3):195-202.
Graham et al., Characteristics of a human cell line transformed by DNA from human adenovirus type 5. J Gen Virol. Jul. 1977;36(1):59-74.
Helenius et al., Calnexin, calreticulin and the folding of glycoproteins. Trends Cell Biol. 1997;7:193-200.
Helenius et al., The endoplasmic reticulum as a protein-folding compartment. Trends Cell Biol. Aug. 1992;2(8):227-31.
Henrissat et al., Structural and sequence-based classification of glycoside hydrolases. Curr Opin Struct Biol. Oct. 1997;7(5):637-44.
Hopwood et al., The mucopolysaccharidoses. Diagnosis, molecular genetics and treatment. Mol Biol Med. Oct. 1990;7(5):381-404.
Horsch et al., N-acetylglucosaminono-1,5-lactone oxime and the corresponding (phenylcarbamoyl)oxime. Novel and potent inhibitors of beta-N-acetylglucosaminidase. Eur J Biochem. May 8, 1991;197(3):815-8.
Hurtley et al., Protein oligomerization in the endoplasmic reticulum. Annu Rev Cell Biol. 1989;5:277-307. Review.
Ikeda et al., Synthesis of a trisulfated heparan sulfate disaccharide analog and its use as a template for preliminary molecular imprinting studies. Carbohydr Res. Mar. 17, 2008;343(4):587-95. doi: 10.1016/j.carres.2007.12.020. Epub Dec. 28, 2007.
Jakob et al., Degradation of misfolded endoplasmic reticulum glycoproteins in Saccharomyces cerevisiae is determined by a specific oligosaccharide structure. J Cell Biol. Sep. 7, 1998;142(5):1223-33.
Kearse et al., Persistence of glucose residues on core oligosaccharides prevents association of TCR alpha and TCR beta proteins with calnexin and results specifically in accelerated degradation of nascent TCR alpha proteins within the endoplasmic reticulum. EMBO J. Aug. 15, 1994;13(16):3678-86.
Koide, Engineering of recombinant crystallization chaperones. Curr Opin Struct Biol. Aug. 2009;19(4):449-57. doi: 10.1016/j.sbi.2009.04.008. Epub May 26, 2009. Review.
Korneeld et al., The biogenesis of lysosomes. Annu Rev Cell Biol. 1989;5:483-525. Review.
Kuntz et al., A geometric approach to macromolecule-ligand interactions. J Mol Biol. Oct. 25, 1982;161(2):269-88.

Landon et al., Detection of ligand binding hot spots on protein surfaces via fragment-based methods: application to DJ-1 and glucocerebrosidase. J Comput Aided Mol Des. Aug. 2009;23(8):491-500. doi: 10.1007/s10822-009-9283-2. Epub Jun. 12, 2009.
Laskowski et al., Procheck: A program to check the stereochemical quality of protein structures. J Appl Crystallogr. 1993;26:283-91.
Li et al., Mouse model of Sanfilippo syndrome type B produced by targeted disruption of the gene encoding alpha-N-acetylglucosaminidase. Proc Natl Acad Sci U S A. Dec. 7, 1999;96(25):14505-10.
Lieberman et al., Structure of acid beta-glucosidase with pharmacological chaperone provides insight into Gaucher disease. Nat Chem Biol. Feb. 2007;3(2):101-7. Epub Dec. 24, 2006.
Liu et al., A potent inhibitor of beta-N-acetylglucosaminidases: 6-acetamido-6-deoxycastanospermine. Tetrahedron Lett. 1991;32:719-20.
Liu et al., Intracellular disposal of incompletely folded human alpha1-antitrypsin involves release from calnexin and post-translational trimming of asparagine-linked oligosaccharides. J Biol Chem. Mar. 21, 1997;272(12):7946-51.
Liu et al., Oligosaccharide modification in the early secretory pathway directs the selection of a misfolded glycoprotein for degradation by the proteasome. J Biol Chem. Feb. 26, 1999;274(9):5861-7.
Loo et al., Chemical and pharmacological chaperones as new therapeutic agents. Expert Rev Mol Med. Jun. 28, 2007;9(16):1-18. Review.
Maas et al., A role for protein misfolding in immunogenicity of biopharmaceuticals. J Biol Chem. Jan. 26, 2007;282(4):2229-36. Epub Nov. 29, 2006.
MacAuley et al., O-GlcNAcase uses substrate-assisted catalysis: kinetic analysis and development of highly selective mechanism-inspired inhibitors. J Biol Chem. Jul. 8, 2005;280(27):25313-22. Epub Mar. 28, 2005.
Mahuran, Biochemical consequences of mutations causing the GM2 gangliosidoses. Biochim Biophys Acta. Oct. 8, 1999;1455(2-3):105-38.
Malinowska et al., Genistein reduces lysosomal storage in peripheral tissues of mucopolysaccharide IIIB mice. Mol Genet Metab. Nov. 2009;98(3):235-42. doi:10.1016/j.ymgme.2009.06.013. Epub Jun. 27, 2009.
Marcus et al., Glucosidase and mannosidase inhibitors mediate increased secretion of mutant alpha1 antitrypsin Z. J Biol Chem. Jan. 21, 2000;275(3):1987-92.
Martin, 3D database searching in drug design. J Med Chem. Jun. 12, 1992;35(12):2145-54. Review.
Mather et al., Culture of testicular cells in hormone-supplemented serum-free medium. Ann N Y Acad Sci. 1982;383:44-68. Review.
Mather, Establishment and characterization of two distinct mouse testicular epithelial cell lines. Biol Reprod. Aug. 1980;23(1):243-52.
Mattos et al., Multiple solvent crystal structures: probing binding sites, plasticity and hydration. J Mol Biol. Apr. 14, 2006;357(5):1471-82. Epub Jan. 30, 2006.
Miranker et al., Functionality maps of binding sites: a multiple copy simultaneous search method. Proteins. 1991;11(1):29-34.
Moore et al., Inhibition of glucose trimming by castanospermine results in rapid degradation of unassembled major histocompatibility complex class I molecules. J Biol Chem. Feb. 25, 1993;268(6):3809-12.
Moura et al., Large scale comparative codon-pair context analysis unveils general rules that fine-tune evolution of mRNA primary structure. PLoS One. Sep. 5, 2007;2(9):e847.
Murshudov et al., Refinement of macromolecular structures by the maximum-likelihood method. Acta Crystallogr D Biol Crystallogr. May 1, 1997;53(Pt 3):240-55.
Navaza, AmoRe: an Automated Package for Molecular Replacement. Acta Cryst. 1994;A50:157-63.
Navia et al., Use of structural information in drug design. Current Opinions in Structural Biology. 1992;2:202-10.

(56) References Cited

OTHER PUBLICATIONS

Nishibata et al., Automatic Cretion of Drug Candidate Sructures Based on Receptor Structure. Starting Point fo Artificial Lead Generation. Tetrahedron. 1991;47:8985-90.
Ogawa et al., Development and medical application of unsaturated carbaglycosylamine glycosidase inhibitors. Mini Rev Med Chem. Jul. 2007;7(7):679-91.
Ohmi et al., Sanfilippo syndrome type B, a lysosomal storage disease, is also a tauopathy. Proc Natl Acad Sci U S A. May 19, 2009;106(20):8332-7. Epub May 5, 2009.
Peltekian et al., Sanfilippo Syndrome: current knowledge and perspectives for therapies. Alliance Sanfilippo. France. Dec. 2006 36 pages.
Perrakis et al., Automated protein model building combined with iterative structure refinement. Nat Struct Biol. May 1999;6(5):458-63.
Pflugrath, The finer things in X-ray diffraction data collection. Acta Crystallogr D Biol Crystallogr. Oct. 1999;55(Pt 10):1718-25.
Read, Improved Fourier coefficients for maps using phases from partial structures with errors. Acta Crystallog A. 1986;42:140-9.
Rempel et al., A homology model for human alpha-1-iduronidase: insights into human disease. Mol Genet Metab. May 2005;85(1):28-37. Epub Feb. 10, 2005.
Ringe et al., What are pharmacological chaperones and why are they interesting? J Biol. Oct. 13, 2009;8(9):80. doi: 10.1186/jbiol186.
Ringe, What makes a binding site a binding site? Curr Opin Struct Biol. Dec. 1995;5(6):825-9. Review.
Salvatore et al., Biosynthesis of α-N-acetylglucosaminidase in human kidney cells. Biol Cell. 1982;45:212.
Salvatore et al., Lysomal α-N-Acetylglucosaminidase: Purification and Characterization of the Human Urinary Enzyme. Bull Mol Biol Med. 1984;9:111-21.
Sanchez-Ruiz, Ligand effects on protein thermodynamic stability. Biophys Chem. Mar. 2007;126(1-3):43-9. Epub Jun. 14, 2006. Review.
Sasaki et al., Purification and partial characterization of alpha-N-acetylglucosaminidase from human liver. J Biochem. Nov. 1991;110(5):842-6.
Sawkar et al., Chemical chaperones increase the cellular activity of N370S beta-glucosidase: a therapeutic strategy for Gaucher disease. Proc Natl Acad Sci U S A. Nov. 26, 2002;99(24):15428-33. Epub Nov. 14, 2002.
Schmidtchen et al., NAGLU mutations underlying Sanfilippo syndrome type B. Am J Hum Genet. Jan. 1998;62(1):64-9.
Schneider et al., Substructure solution with SHELXD. Acta Crystallogr D Biol Crystallogr. Oct. 2002;58(Pt 10 Pt 2):1772-9. Epub Sep. 28, 2002.
Schwede et al., SWISS-MODEL: An automated protein homology-modeling server. Nucleic Acids Res. Jul. 1, 2003;31(13):3381-5.
Steet et al., The iminosugar isofagomine increases the activity of N370S mutant acid beta-glucosidase in Gaucher fibroblasts by several mechanisms. Proc Natl Acad Sci U S A. Sep. 12, 2006;103(37):13813-8. Epub Aug. 31, 2006.
Tanaka et al., Molecular analysis of the alpha-N-acetylglucosaminidase gene in seven Japanese patients from six unrelated families with mucopolysaccharidosis IIIB (Sanfilippo type B), including two novel mutations. J Hum Genet. 2002;47(9):484-7.
Tats et al., Preferred and avoided codon pairs in three domains of life. BMC Genomics. Oct. 8, 2008;9:463. 15 pages.
Tessitore et al., Molecular defects in the alpha-N-acetylglucosaminidase gene in Italian Sanfilippo type B patients. Hum Genet. Dec. 2000;107(6):568-76.
Tropak et al., Pharmacological enhancement of beta-hexosaminidase activity in fibroblasts from adult Tay-Sachs and Sandhoff Patients. J Biol Chem. Apr. 2, 2004;279(14):13478-87. Epub Jan. 14, 2004.
Urlaub et al., Isolation of Chinese hamster cell mutants deficient in dihydrofolate reductase activity. Proc Natl Acad Sci U S A. Jul. 1980;77(7):4216-20.
Vallmitjana et al., Mechanism of the family 1 beta-glucosidase from *Streptomyces* sp: catalytic residues and kinetic studies. Biochemistry. May 22, 2001;40(20):5975-82.
Van Aalten et al., PRODRG, a program for generating molecular topologies and unique molecular descriptors from coordinates of small molecules. J Comput Aided Mol Des. Jun. 1996;10(3):255-62.
Verhoeven et al., Secretion and apparent activation of human hepatic lipase requires proper oligosaccharide processing in the endoplasmic reticulum. Biochem J. Jan. 1, 1999;337 ( Pt 1):133-40.
Von Figura et al., Biosynthesis and maturation of alpha-N-acetylglucosaminidase in normal and Sanfilippo B-fibroblasts. Am J Hum Genet. Jan. 1984;36(1):93-100.
Weber et al., Cloning and expression of the gene involved in Sanfilippo B syndrome (mucopolysaccharidosis III B). Hum Mol Genet. Jun. 1996;5(6):771-7.
Weber et al., Expression and characterization of human recombinant and alpha-N-acetylglucosaminidase. Protein Expr Purif. Mar. 2001;21(2):251-9.
Weber et al., Sanfilippo type B syndrome (mucopolysaccharidosis III B): allelic heterogeneity corresponds to the wide spectrum of clinical phenotypes. Eur J Hum Genet. Jan. 1999;7(1):34-44.
Welch et al., Influence of molecular and chemical chaperones on protein folding. Cell Stress Chaperones. Jun. 1996;1(2):109-15. Review.
Winchester et al., Amino-sugar glycosidase inhibitors: versatile tools for glycobiologists. Glycobiology. Jun. 1992;2(3):199-210. Review.
Wiseman et al., Rapid measurement of binding constants and heats of binding using a new titration calorimeter. Anal Biochem. May 15, 1989;179(1):131-7.
Yang et al., Novel aspects of degradation of T cell receptor subunits from the endoplasmic reticulum (ER) in T cells: importance of oligosaccharide processing, ubiquitination, and proteasome-dependent removal from ER membranes. J Exp Med. Mar. 16, 1998;187(6):835-46.
Yates et al., Highly diverse heparan sulfate analogue libraries: providing access to expanded areas of sequence space for bioactivity screening. J Med Chem. Jan. 1, 2004;47(1):277-80.
Yogalingam et al., Molecular genetics of mucopolysaccharidosis type IIIA and IIIB: Diagnostic, clinical, and biological implications. Hum Mutat. Oct. 2001;18(4):264-81. Review.
Yogalingam et al., Mucopolysaccharidosis type IIIB: characterisation and expression of wild-type and mutant recombinant alpha-N-acetylglucosaminidase and relationship with sanfilippo phenotype in an attenuated patient. Biochim Biophys Acta. Nov. 15, 2000;1502(3):415-25.
Yu et al., Short-term enzyme replacement in the murine model of Sanfilippo syndrome type B. Mol Genet Metab. Dec. 2000;71(4):573-80.
Zapun et al., Conformation-independent binding of monoglucosylated ribonuclease B to calnexin. Cell. Jan. 10, 1997;88(1):29-38.
Zechel et al., Mechanism, mutagenesis, and chemical rescue of a beta-mannosidase from cellulomonas fimi. Biochemistry. Jun. 17, 2003;42(23):7195-204.
Zhao et al., Purification and characterization of recombinant human alpha-N-acetylglucosaminidase secreted by Chinese hamster ovary cells. Protein Expr Purif. Jun. 2000;19(1):202-11.
Zhao et al., The molecular basis of Sanfilippo syndrome type B. Proc Natl Acad Sci U S A. Jun. 11, 1996;93(12):6101-5.
Zheng et al., Retrovirally transduced bone marrow has a therapeutic effect on brain in the mouse model of mucopolysaccharidosis IIIB. Mol Genet Metab. Aug. 2004;82(4):286-95.

\* cited by examiner

Figure 2

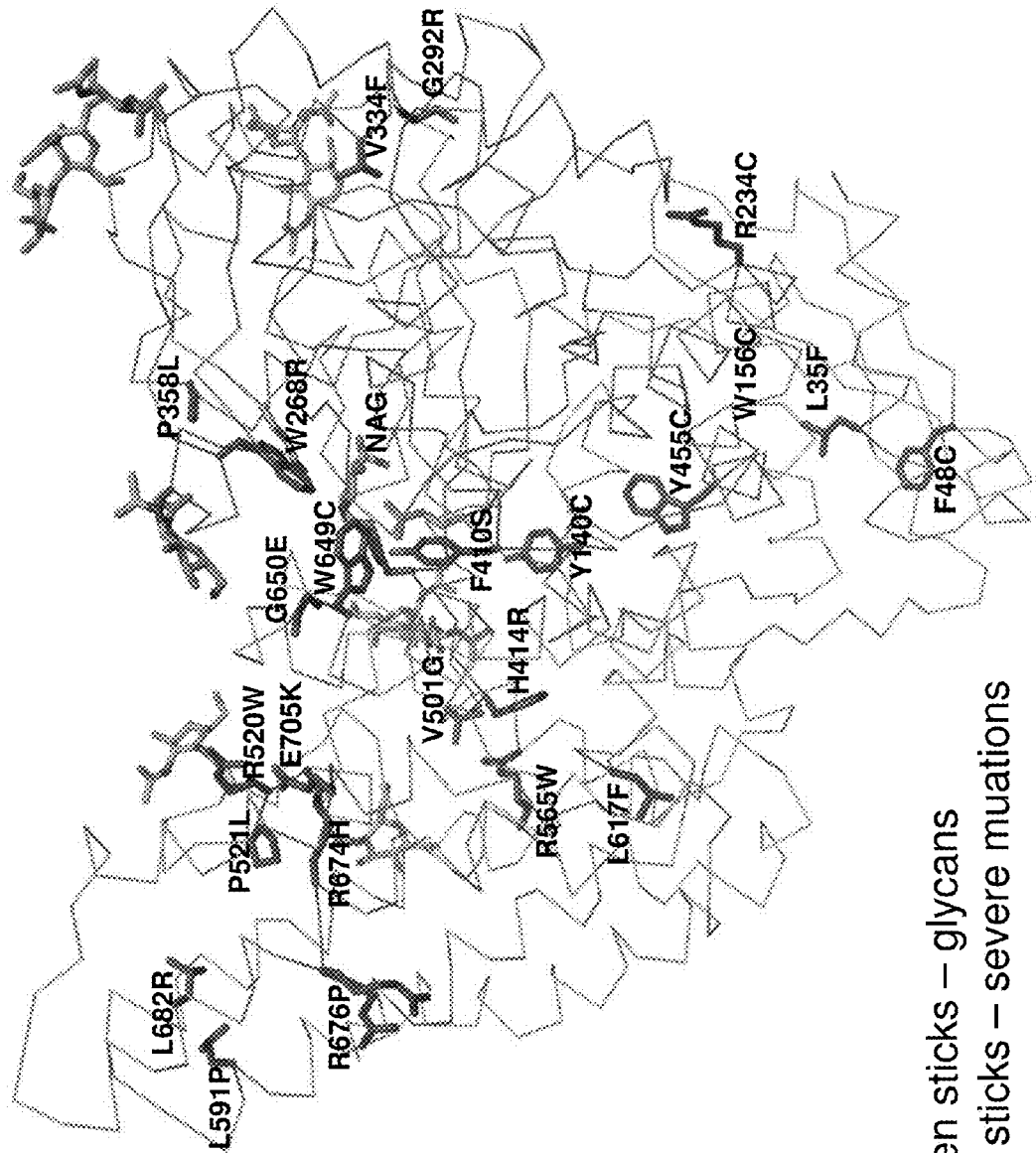
Figure 10: Severe mutations mapped on Naglu structure
Green sticks – glycans
Red sticks – severe mutations

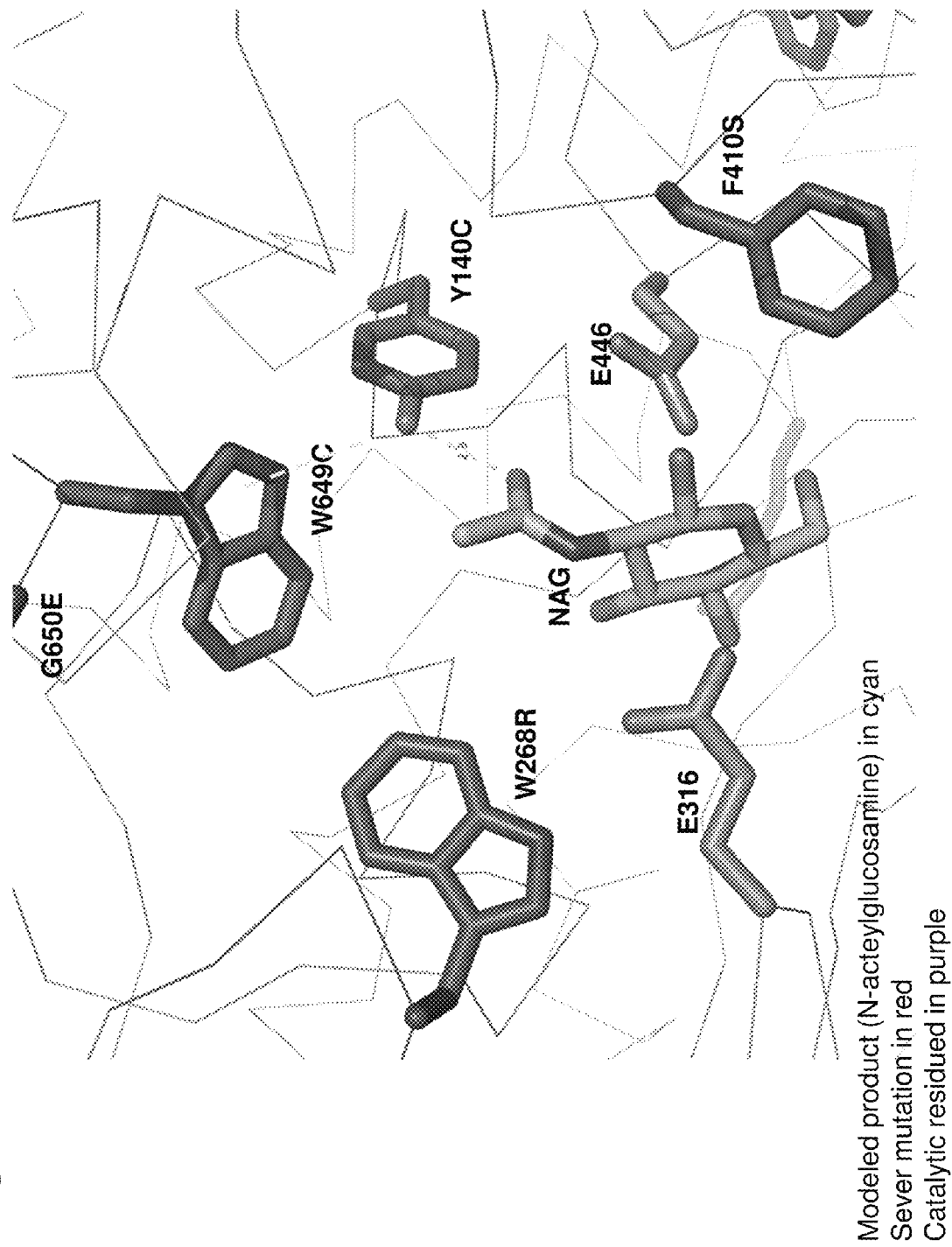
Figure 11: Active Site Mutations

Figure 12: Cluster of mutations around a loop containing three glycosylation sites.
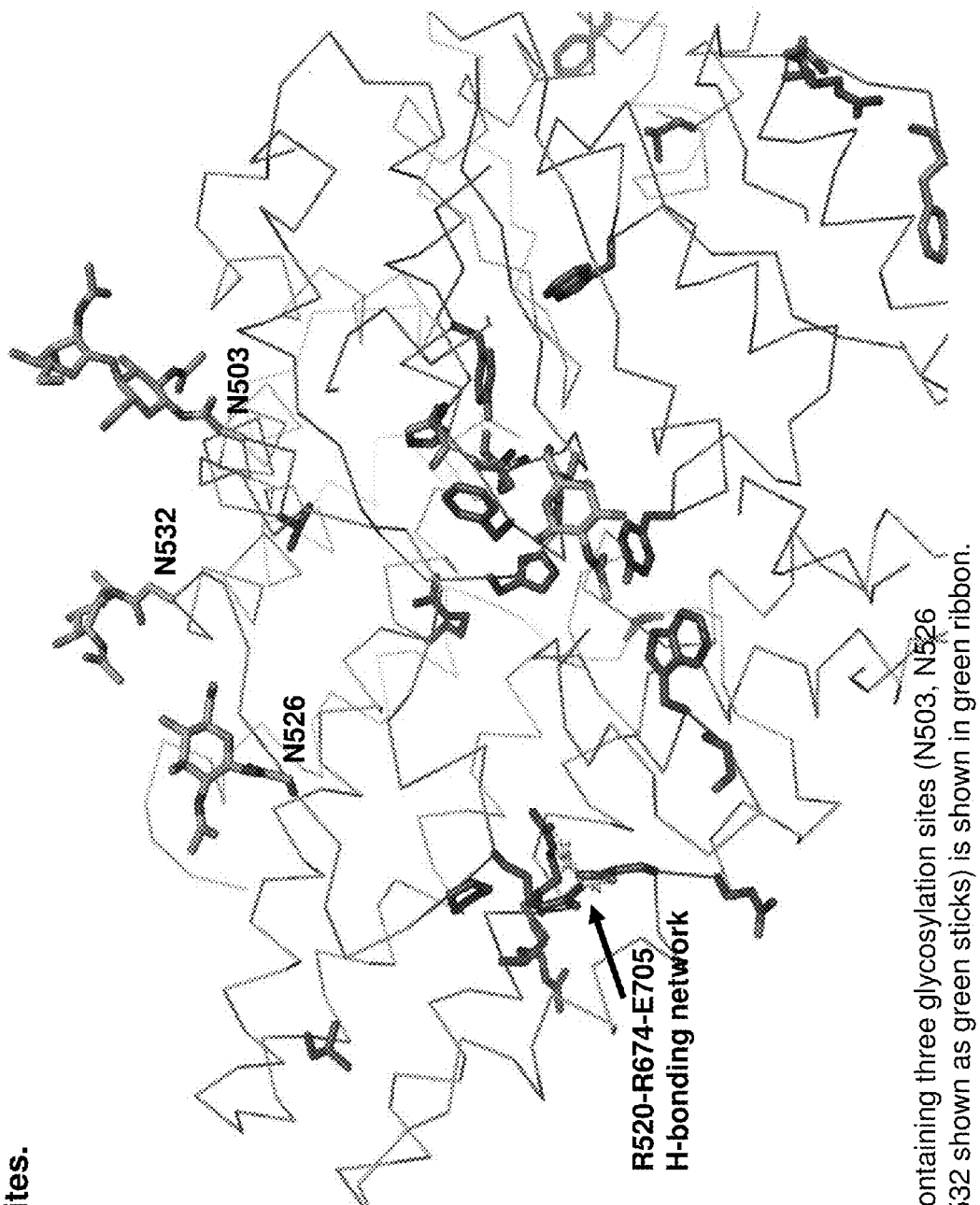
Loop containing three glycosylation sites (N503, N526 and N532 shown as green sticks) is shown in green ribbon.

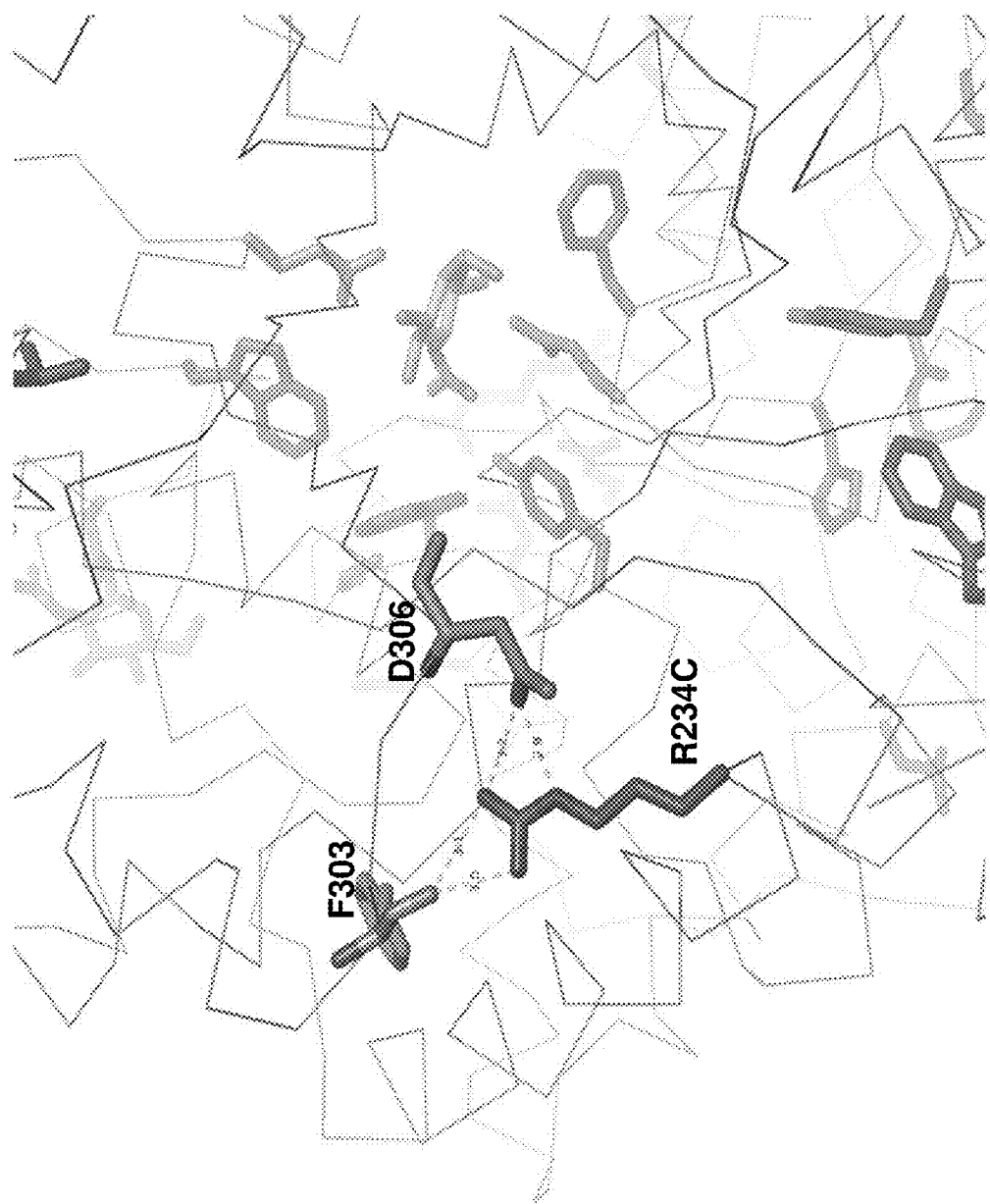
Figure 13: Severe Naglu muation R234C

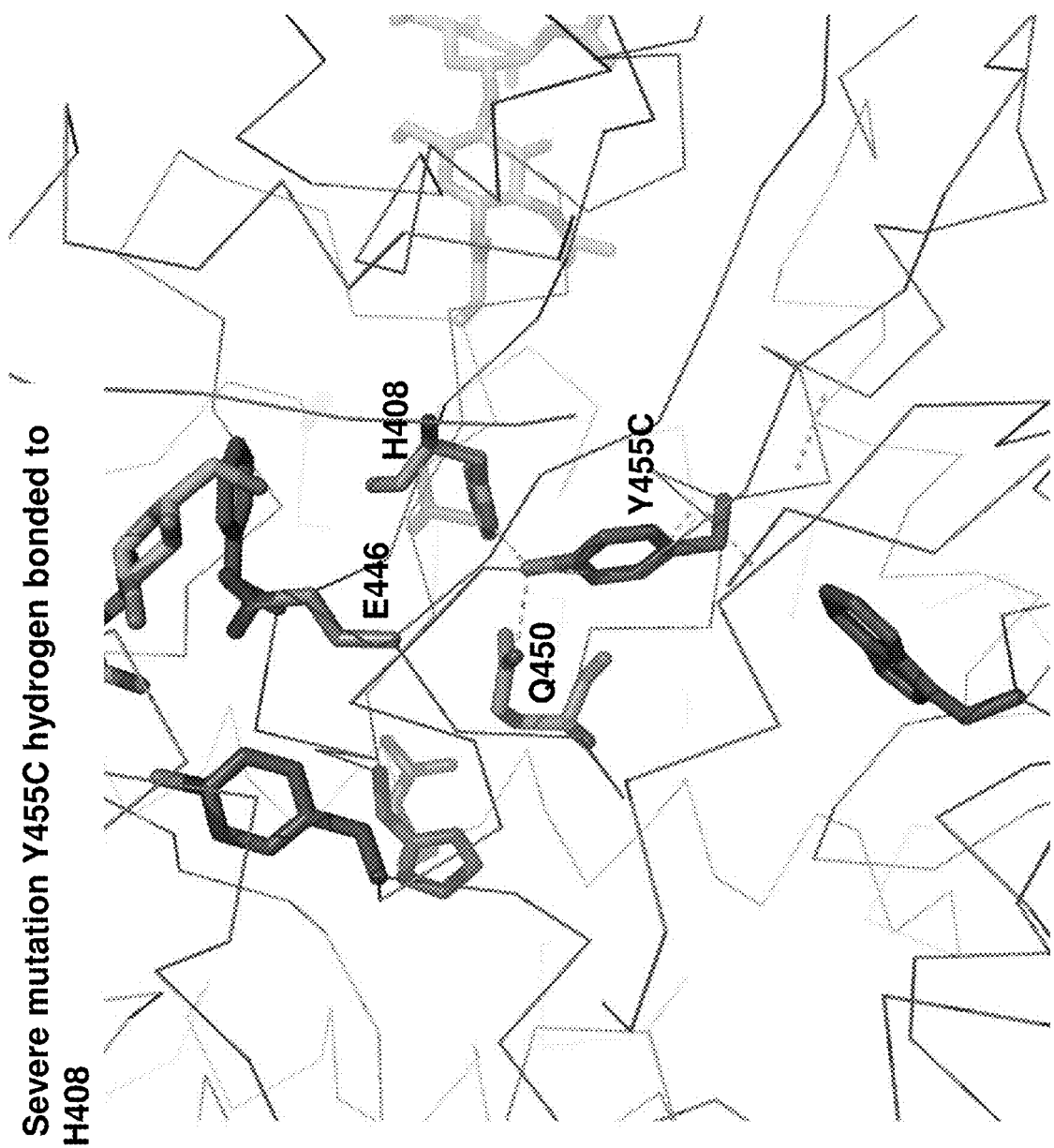
Figure 14: Severe mutation Y455C hydrogen bonded to Q450 and H408

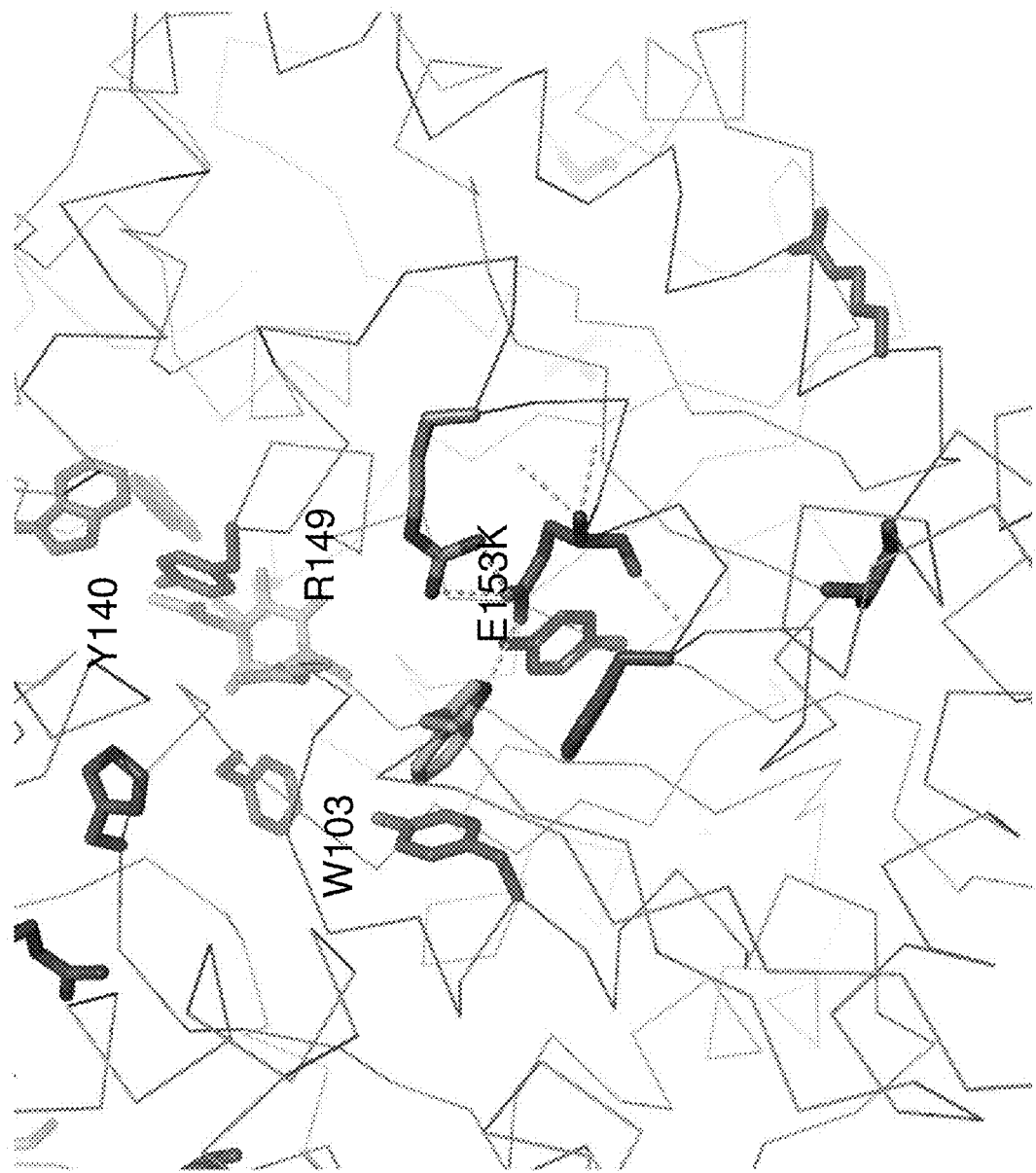
Figure 15: E153K Mutation

Figure 16: Mutation Clusters

Red: Severe
Yellow: Attenuated
Blue: N.R
Green: Glycans

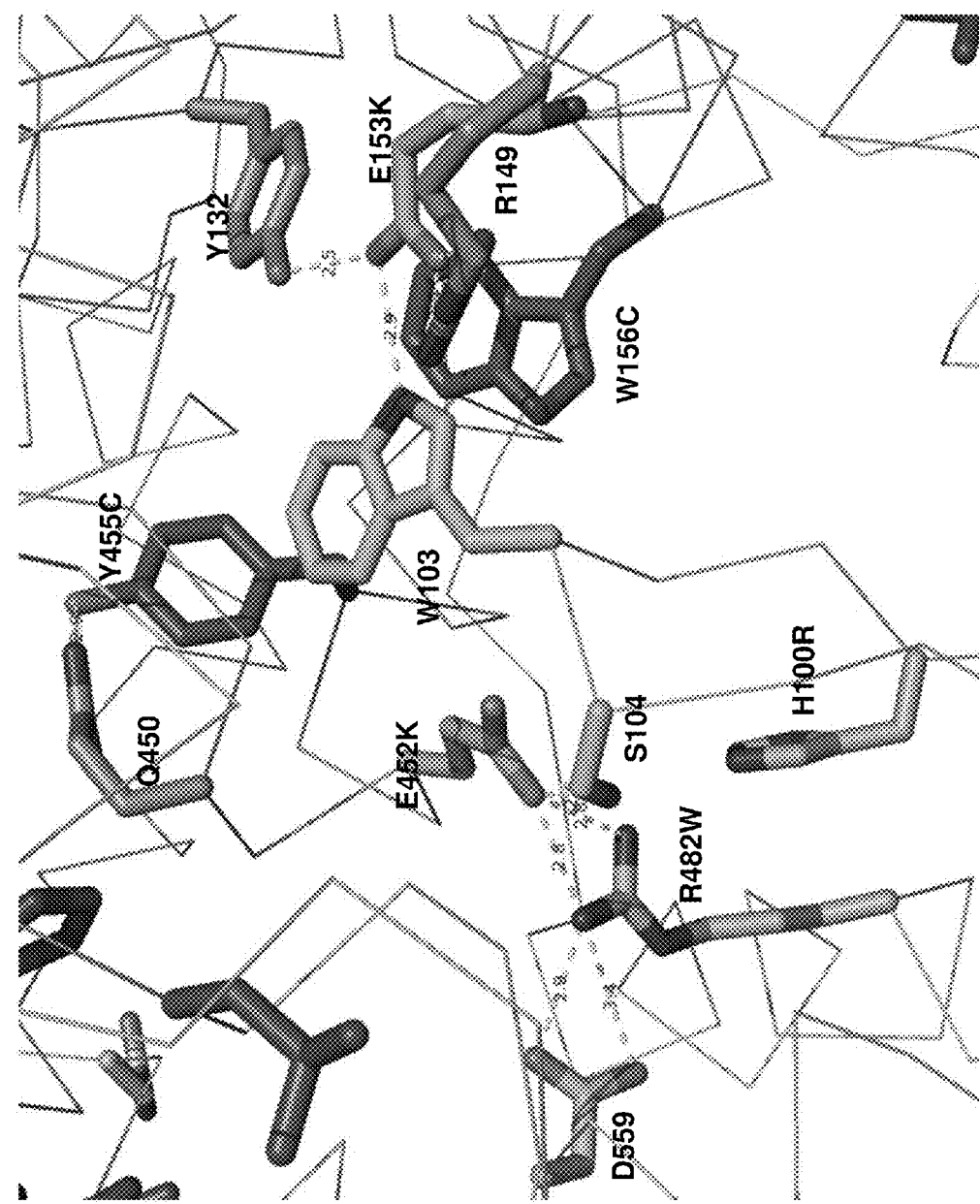
Figure 17: Six Mutations at Domain Interface

Blue: rhNAGLU
Red: NAGLU-kif

SEQUENCE LISTING

```
<160> NUMBER OF SEQ ID NOS: 6

<210> SEQ ID NO 1
<211> LENGTH: 743
<212> TYPE: PRT
<213> ORGANISM: Homo sapiens

<400> SEQUENCE: 1

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190
```

```
Phe Thr Gly Pro Ala Phe Leu Ala Trp Gly Arg Met Gly Asn Leu His
    195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
            275                 280                 285

Pro Ile Ile Gly Ser Leu Phe Leu Arg Glu Leu Ile Lys Glu Phe Gly
            290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
            370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
                500                 505                 510

Asn Arg Ser Pro Leu Val Arg Arg Pro Ser Leu Gln Met Asn Thr Ser
            515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
            595                 600                 605
```

Val Leu Ala Ser Asp Ser Arg Phe Leu Leu Gly Ser Trp Leu Glu Gln
610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
                660                 665                 670

Pro Arg Trp Arg Leu Phe Leu Glu Ala Leu Val Asp Ser Val Ala Gln
                675                 680                 685

Gly Ile Pro Phe Gln Gln His Gln Phe Asp Lys Asn Val Phe Gln Leu
690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
                740

<210> SEQ ID NO 2
<211> LENGTH: 891
<212> TYPE: PRT
<213> ORGANISM: Clostridium perfringens

<400> SEQUENCE: 2

Gly Val Glu Ile Thr Glu Gly Val Thr Val Thr Ala Lys Gly Asn Thr
1               5                   10                  15

Glu Gly Asn Thr Ala Asp Leu Ala Ile Asp Gly Asp Leu Ser Thr Tyr
                20                  25                  30

Trp Glu Ser Ser Asn Asp Tyr Lys Trp Ile Glu Val Asp Leu Gly Gly
            35                  40                  45

Ile Tyr Glu Leu Ser Lys Ile Glu Ile Phe Asn Lys Asp Glu Ala Val
        50                  55                  60

Tyr Lys Tyr Asn Ile Tyr Ala Ser Glu Asp Gly Glu Asn Phe Asn Lys
65                  70                  75                  80

Ile Ala Tyr Lys Asn Asn Asp Asn Val Ser Asp Ser Asn Gly Asn Met
                85                  90                  95

His Thr Ile Asp Asn Val Arg Ala Gly Lys Ile Arg Ile Asp Val Val
                100                 105                 110

Gln Asn Ser Asn Ser Asp Arg Val Asn Ile Ala Glu Ile Asn Val Phe
            115                 120                 125

Gly Lys Asn Thr Gly Glu Ser Leu Pro Glu Val Lys Lys Ile Ala Thr
130                 135                 140

Ser Asn Phe Ser Glu Thr Pro Trp Ala Thr Glu Tyr Glu Lys Phe Asn
145                 150                 155                 160

Ser Asp Ser Ala Tyr Ala Asn Glu Lys Thr Leu Asn Glu Ile Lys Asn
                165                 170                 175

Leu Val Gly Arg Val Ile Gly Arg Glu Phe Lys Asp Lys Phe Ile Phe
                180                 185                 190

Glu Ile Arg Asp Gln Leu Asn Gly Asn Asp Val Phe Glu Val Ser Asp
            195                 200                 205

Ser Gly Asp Gly Lys Val Leu Ile Lys Gly Asn Asn Gly Val Ser Leu
210                 215                 220

Ala Ser Gly Phe Asn Tyr Tyr Leu Lys Asn Tyr Cys Asn Val Ser Tyr
225                 230                 235                 240

-continued

```
Asn Pro Ile Met Gly Ser Asn Leu Lys Met Pro Glu Thr Met Pro Ser
            245                 250                 255

Val Gly Glu Arg Val Val Ile Asp Thr Pro Tyr Glu His Arg Tyr Ala
        260                 265                 270

Leu Asn Phe Cys Thr Tyr Ser Tyr Thr Met Ser Phe Trp Asp Trp Asp
    275                 280                 285

Gln Tyr Glu Glu Phe Leu Asp Trp Cys Ala Met Asn Gly Val Asn Leu
290                 295                 300

Val Leu Asp Ile Ile Gly Gln Glu Glu Val Leu Arg Arg Thr Leu Asn
305                 310                 315                 320

Glu Phe Gly Tyr Ser Asp Glu Glu Val Lys Glu Phe Ile Ser Gly Pro
                325                 330                 335

Ala Tyr Phe Ala Trp Phe Tyr Met Gln Asn Met Thr Gly Phe Gly Gly
            340                 345                 350

Pro Leu Pro Asn Asp Trp Phe Glu Gln Arg Ala Glu Leu Gly Arg Lys
        355                 360                 365

Met His Asp Arg Met Gln Ser Phe Gly Ile Asn Pro Val Leu Gln Gly
    370                 375                 380

Tyr Ser Gly Met Val Pro Arg Asp Phe Lys Lys Asn Gln Glu Ala
385                 390                 395                 400

Gln Thr Ile Ser Gln Gly Gly Trp Cys Gly Phe Asp Arg Pro Asp Met
                405                 410                 415

Leu Lys Thr Tyr Val Asn Glu Gly Glu Ala Asp Tyr Phe Gln Lys Val
            420                 425                 430

Ala Asp Val Phe Tyr Glu Lys Gln Lys Glu Val Phe Gly Asp Val Thr
        435                 440                 445

Asn Phe Tyr Gly Val Asp Pro Phe His Glu Gly Gly Asn Thr Gly Asp
    450                 455                 460

Leu Asp Asn Gly Lys Ile Tyr Glu Ile Ile Gln Asn Lys Met Ile Glu
465                 470                 475                 480

His Asp Asn Asp Ala Val Trp Val Ile Gln Asn Trp Gln Gly Asn Pro
                485                 490                 495

Ser Asn Asn Lys Leu Glu Gly Leu Thr Lys Lys Asp Gln Ala Met Val
            500                 505                 510

Leu Asp Leu Phe Ser Glu Val Ser Pro Asp Trp Asn Arg Leu Glu Glu
        515                 520                 525

Arg Asp Leu Pro Trp Ile Trp Asn Met Leu His Asn Phe Gly Gly Arg
    530                 535                 540

Met Gly Met Asp Ala Ala Pro Glu Lys Leu Ala Thr Glu Ile Pro Lys
545                 550                 555                 560

Ala Leu Ala Asn Ser Glu His Met Val Gly Ile Gly Ile Thr Pro Glu
                565                 570                 575

Ala Ile Asn Thr Asn Pro Leu Ala Tyr Glu Leu Leu Phe Asp Met Ala
            580                 585                 590

Trp Thr Arg Asp Gln Ile Asn Phe Arg Thr Trp Thr Glu Asp Tyr Ile
        595                 600                 605

Glu Arg Arg Tyr Gly Lys Thr Asn Lys Glu Ile Leu Glu Ala Trp Asn
    610                 615                 620

Ile Ile Leu Asp Thr Ala Tyr Lys Lys Arg Asn Asp Tyr Tyr Gln Gly
625                 630                 635                 640

Ala Ala Glu Ser Ile Ile Asn Ala Arg Pro Gly Phe Gly Ile Lys Ser
                645                 650                 655
```

-continued

```
Ala Ser Thr Trp Gly His Ser Lys Ile Val Tyr Asp Lys Ser Glu Phe
                660                 665                 670

Glu Lys Ala Ile Glu Ile Phe Ala Lys Asn Tyr Asp Glu Phe Lys Asp
            675                 680                 685

Ser Asp Ala Phe Leu Tyr Asp Phe Ala Asp Ile Leu Lys Gln Leu Leu
        690                 695                 700

Ala Asn Ser Ala Gln Glu Tyr Tyr Glu Val Met Cys Asn Ala Tyr Asn
705                 710                 715                 720

Asn Gly Asn Gly Glu Lys Phe Lys Phe Val Ser Gly Lys Phe Leu Glu
                725                 730                 735

Leu Ile Lys Leu Gln Glu Arg Val Leu Ser Thr Arg Pro Glu Phe Leu
            740                 745                 750

Ile Gly Asn Trp Ile Glu Asp Ala Arg Thr Met Leu Lys Asp Ser Asp
        755                 760                 765

Asp Trp Thr Lys Asp Leu Phe Glu Phe Asn Ala Arg Ala Leu Val Thr
    770                 775                 780

Thr Trp Gly Ser Arg Asn Asn Ala Asp Gly Gly Leu Lys Asp Tyr
785                 790                 795                 800

Ser Asn Arg Gln Trp Ser Gly Leu Thr Glu Asp Tyr Tyr Ala Arg
                805                 810                 815

Trp Glu Lys Trp Ile Asn Gly Leu Gln Ala Glu Leu Asp Gly Gly Ala
            820                 825                 830

Lys Ala Pro Asn Ile Asp Trp Phe Lys Met Glu Tyr Asp Trp Val Asn
        835                 840                 845

Lys Lys Ser Asp Thr Asp Lys Leu Tyr Pro Thr Glu Ala Ser Asn Glu
    850                 855                 860

Asn Leu Gly Glu Leu Ala Lys Ile Ala Met Glu Ser Tyr Ser Val Thr
865                 870                 875                 880

Asn Met Asp Lys Ile Leu Gly Glu Asn Glu Ser
                885                 890

<210> SEQ ID NO 3
<211> LENGTH: 720
<212> TYPE: PRT
<213> ORGANISM: Homo sapiens

<400> SEQUENCE: 3

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
        35                  40                  45

Ala Ala Arg Val Arg Val Arg Gly Ser Thr Gly Val Ala Ala Ala Ala
    50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Tyr Gln Asn Val
            100                 105                 110

Cys Thr Gln Ser Tyr Ser Phe Val Trp Trp Asp Trp Ala Arg Trp Glu
        115                 120                 125

Arg Glu Ile Asp Trp Met Ala Leu Asn Gly Ile Asn Leu Ala Leu Ala
    130                 135                 140
```

```
Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
            165                 170                 175

Ala Trp Gly Arg Met Gly Asn Leu His Thr Trp Asp Gly Pro Leu Pro
        180                 185                 190

Pro Ser Trp His Ile Lys Gln Leu Tyr Leu Gln His Arg Val Leu Asp
    195                 200                 205

Gln Met Arg Ser Phe Gly Met Thr Pro Val Leu Pro Ala Phe Ala Gly
210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
            245                 250                 255

Leu Leu Ala Pro Glu Asp Pro Ile Phe Pro Ile Ile Gly Ser Leu Phe
        260                 265                 270

Leu Arg Glu Leu Ile Lys Glu Phe Gly Thr Asp His Ile Tyr Gly Ala
    275                 280                 285

Asp Thr Phe Asn Glu Met Gln Pro Pro Ser Ser Glu Pro Ser Tyr Leu
290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
            325                 330                 335

Phe Trp Gly Pro Ala Gln Ile Arg Ala Val Leu Gly Ala Val Pro Arg
        340                 345                 350

Gly Arg Leu Leu Val Leu Asp Leu Phe Ala Glu Ser Gln Pro Val Tyr
    355                 360                 365

Thr Arg Thr Ala Ser Phe Gln Gly Gln Pro Phe Ile Trp Cys Met Leu
370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
            405                 410                 415

Gly Thr Gly Met Ala Pro Glu Gly Ile Ser Gln Asn Glu Val Val Tyr
        420                 425                 430

Ser Leu Met Ala Glu Leu Gly Trp Arg Lys Asp Pro Val Pro Asp Leu
    435                 440                 445

Ala Ala Trp Val Thr Ser Phe Ala Ala Arg Arg Tyr Gly Val Ser His
450                 455                 460

Pro Asp Ala Gly Ala Ala Trp Arg Leu Leu Arg Ser Val Tyr Asn
465                 470                 475                 480

Cys Ser Gly Glu Ala Cys Arg Gly His Asn Arg Ser Pro Leu Val Arg
            485                 490                 495

Arg Pro Ser Leu Gln Met Asn Thr Ser Ile Trp Tyr Asn Arg Ser Asp
        500                 505                 510

Val Phe Glu Ala Trp Arg Leu Leu Thr Ser Ala Pro Ser Leu Ala
    515                 520                 525

Thr Ser Pro Ala Phe Arg Tyr Asp Leu Leu Asp Leu Thr Arg Gln Ala
530                 535                 540

Val Gln Glu Leu Val Ser Leu Tyr Tyr Glu Glu Ala Arg Ser Ala Tyr
545                 550                 555                 560
```

| | | | | | | | | | | | |
|---|---|---|---|---|---|---|---|---|---|---|---|
|Leu|Ser|Lys|Glu|Leu|Ala|Ser|Leu|Leu|Arg|Ala|Gly Gly Val Leu Ala|
| | | | |565| | |570| | | |575|

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Ala Val Ser
        595                 600                 605

Glu Ala Glu Ala Asp Phe Tyr Glu Gln Asn Ser Arg Tyr Gln Leu Thr
    610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
                660                 665                 670

Gln Phe Asp Lys Asn Val Phe Gln Leu Glu Gln Ala Phe Val Leu Ser
            675                 680                 685

Lys Gln Arg Tyr Pro Ser Gln Pro Arg Gly Asp Thr Val Asp Leu Ala
690                 695                 700

Lys Lys Ile Phe Leu Lys Tyr Tyr Pro Arg Trp Val Ala Gly Ser Trp
705                 710                 715                 720

<210> SEQ ID NO 4
<211> LENGTH: 2232
<212> TYPE: DNA
<213> ORGANISM: Homo sapiens

<400> SEQUENCE: 4

```
atggaggcgg tggcggtggc cgcggcggtg ggggtccttc tcctggccgg ggccgggggc      60
gcggcaggcg acgaggcccg ggaggcggcg gccgtgcggg cgctcgtggc ccggctgctg     120
gggccaggcc ccgcggccga cttctccgtg tcggtggagc gcgctctggc tgccaagccg     180
ggcttggaca cctacagcct gggcggcggc ggcgcggcgc gcgtgcgggt gcgcggctcc     240
acgggcgtgg cggccgccgc ggggctgcac cgctacctgc gcgacttctg tgctgccac      300 gtggcctggt ccggctctca gctgcgcctg ccgcggccac tgccagccgt gccggggag     360 ctgaccgagg ccacgcccaa caggtaccgc tattaccaga atgtgtgcac gcaaagctac      420
tccttcgtgt ggtgggactg ggcccgctgg gagcgagaga tagactggat ggcgctgaat      480
ggcatcaacc tggcactggc ctggagcggc caggaggcca tctggcagcg ggtgtacctg      540
gccttgggcc tgacccaggc agagatcaat gagttcttta ctggtcctgc cttcctggcc      600
tgggggcgaa tgggcaacct gcacacctgg gatggccccc tgcccccctc ctggcacatc      660
aagcagcttt acctgcagca ccgggtcctg gaccagatgc gctccttcgg catgaccca      720 gtgctgcctg cattcgcggg gcatgttccc gaggctgtca ccagggtgtt ccctcaggtc      780
aatgtcacga agatgggcag ttggggccac tttaactgtt cctactcctg ctccttcctt      840
ctggctccgg aagaccccat attccccatc atcgggagcc tcttcctgcg agagctgatc      900
aaagagtttg gcacagacca catctatggg gccgacactt caatgagat gcagccacct      960 tcctcagagc cctcctacct tgccgcagcc accactgccg tctatgaggc catgactgca     1020
gtggatactg aggctgtgtg ctgctccaa ggctggctct ccagcacca gccgcagttc     1080 tggggggccg cccagatcag ggctgtgctg ggagctgtgc ccgtggccg cctcctggtt     1140 ctggacctgt tgctgagag ccagcctgtg tatacccgca ctgcctcctt ccagggccag     1200
cccttcatct ggtgcatgct gcacaacttt gggggaaaacc atggtctttt tggagcccta    1260
```

```
gaggctgtga acggaggccc agaagctgcc cgcctcttcc ccaactccac catggtaggc   1320
acgggcatgg cccccgaggg catcagccag aacgaagtgg tctattccct catggctgag   1380
ctgggctggc gaaaggaccc agtgccagat ttggcagcct gggtgaccag ctttgccgcc   1440
cggcggtatg gggtctccca cccggacgca ggggcagcgt ggaggctact gctccggagt   1500
gtgtacaact gctccgggga ggcctgcagg ggccacaatc gtagcccgct ggtcaggcgg   1560
ccgtccctac agatgaatac cagcatctgg tacaaccgat ctgatgtgtt tgaggcctgg   1620
cggctgctgc tcacatctgc tccctccctg gccaccagcc ccgccttccg ctacgacctg   1680
ctggacctca ctcggcaggc agtgcaggag ctggtcagct tgtactatga ggaggcaaga   1740
agcgcctacc tgagcaagga gctggcctcc ctgttgaggg ctggaggcgt cctggcctat   1800
gagctgctgc cggcactgga cgaggtgctg gctagtgaca gccgcttctt gctgggcagc   1860
tggctagagc aggcccgagc agcggcagtc agtgaggccg aggccgattt ctacgagcag   1920
aacagccgct accagctgac cttgtggggg ccagaaggca acatcctgga ctatgccaac   1980
aagcagctgg cggggttggt ggccaactac tacacccctc gctggcggct tttcctggag   2040
gcgctggttg acagtgtggc ccagggcatc cctttccaac agcaccagtt tgacaaaaat   2100
gtcttccaac tggagcaggc cttcgttctc agcaagcaga ggtaccccag ccagccgcga   2160
ggagacactg tggacctggc caagaagatc ttcctcaaat attaccccccg ctgggtggcc   2220 ggctcttggt ga                                                       2232

<210> SEQ ID NO 5
<211> LENGTH: 11977
<212> TYPE: DNA
<213> ORGANISM: Artificial Sequence
<220> FEATURE:
<223> OTHER INFORMATION: Synthetic Polynucleotide

<400> SEQUENCE: 5
gaattctcga gtcgagatcc cccgggctgc aggaattcga ggctgcagtg cccccagatc     60
acactactgc actccagcct gggtgataaa gtgagacctt ctcaataaat aaataaatac    120
aaaattaaaa accagcactt aactcttcag ctaccacatt aattctcagc aaataccttc    180
ttagcagtcg tttgacaatc aagtcaacta gaactggaac tagaatgaga taacatggta    240
ttgcttcttc tcacagagta gatcctcaat gaatgtttga aggagatgt cagtccgatg    300 tttacctttg atcaaagaaa ggaatataag attaagacat cagggcctcg tcaggctgtt    360
ctgcatttct gtattagcca gactctcaac cattttcttg ccatatataa acatgtggcc    420
cagtttgtaa tcagtgggtt ataggaagct aaagaaatta tctttttcttt catagaaaat    480 aatttgggca taggaaccca ggtattaacc gtctagcacc aaagttgtag gaatctttag    540
tctcctctgc ctcccttctt ccatccctct actctcagtc ttgacccac cccaccccttt    600 acttgttttt cctttctactc attttctcct ccctcccctct ccctctccc cacactagaa    660 ccatcagggc cctcaccagg gcattcagtt caggttctgg gtcagctctc acagctctac    720
cagtcccacc cccatcccca ggaaaaactg ctccttattt ggagtcacaa aaatatttaa    780
cagagatcta actgaccact aaaaattcct cctttaaaac aaacacctaa tcaactattt    840
tcccccaagt tatatggaaa aacagctgca attagaactt gattctcact ttaagaaaga    900
aagattcttg tttggttttc tccactttca tttttttgttt ctaggtccag ggcctcccac    960
caaatgctga cggctgcctg cttcaaaccc tgccacatca gcagggaggg agcacagcgg   1020
```

```
catttggtat ttgcatcagt ttccaggaat gcttttcaag ttatcagttc actctgctgc      1080
ctttagcaga gacgttttcc ctctaagttt atagatgtct gcttcaattt acagtcctct      1140
aattctcaaa aacttgctga ggatttttct tttttggcta aaagagaaat tataatcaca      1200
cttctaaaaa cattctatgt tttaaactat tttgacaaca acaacaaaac ctacaatgaa      1260
atgtttaaaa cttgggatat ctattgcaaa tccaatgatt gagccaactt gaccccagaa      1320
gcgttatcag ataaccctca ctgaagggtat ttggagggtt tctttcataa atctgttgca     1380
ttaccaccct gagtcatttt gctcagaatt agtctctgac tctcagcaac acaggacaaa      1440
tacacacata tgccctgcaa aggtaattca gcacagtggt aacaatgatt cttagaaatc      1500
atttctcact cttctgatat gcagaaaaaa atttgttatg atgtagtatt gaagttttc       1560 tttcctgata aaaatgattt ccactttaaa agttttttgt tagttctgta acggtgatat      1620
ttcagggaaa tgttaaaaat gttcttggaa tatacaattc aacctcaggt cttttgttgt      1680
tgttgttcct agaacctaga aaacttcaaa cattgttgcc tagttagaaa aaaatttgaa      1740
tgtggattgc tccctgtaaa ccccccttcta ggaatgacca gtaaccctt caaattcttt      1800 cactcccagt tacttcaaaa aatcatccaa agtggtctcc caagtgagtg cctttaatta     1860
gaataaaaca agagtttatt atagtttttg gttatccact tttacttgca ttaacctttt     1920
tttcttcttt tacatttaga aagagtaacc tgctttagaa tagtcccttt tatttacaga     1980
agctgctgat ggagttaact tctgcagaaa ttcttcctta aggcaaagca aaaaaagcgg      2040
ggagggggtg gggggaagga agggaaaaag attctcaggg aactacagcc cacttgcttc     2100
tgtttcttag agacagaact gacctaaaga tgccccctt gcgatgactt ctgggataga     2160
gcagcactct aactaggccc ccgctgcctc atggggacct taggcaagta gaggagaggc      2220
ctgacacaca cacacacaca cacacacaca cacgcacacg cgcgcgcgcg cacacacaca      2280
cacacagcct ttcaaaccta gggcctggaa tgccatccca agaggcttta gaaaaaggca     2340
caggaccttt ggcctcccac ctcagggtca aagtaccagt tcctcctctc cctagtaggg     2400
agtggagggt tggatggagg cggccagaga agagggaagt tgggtgctgg ggagagagtt     2460
aacatccacg ttggtgggcg cactgcttgg ggtgttacca gcgaagacta cgaagacccc     2520
aagctcgaat cagaagggcc tctggatgtg ctaggggagg tgcttgggtg tggctgtaag     2580
agatgggaca gagagtaagc agcaaggtca agagggaccg gggggctcac gggagggttg     2640
aagggtccag gctcagggta gaactggtaa atccagacaa ggagcccatg gagaagggga     2700
ggggagactg gaaccatga aagatccccc accgcagcct cagaaaggag agactgagaa     2760
ataagttctc ggtctccagg tcggttggag tcgtgtcgga gtgccagacc atcccccaaa     2820
agaccctctt tggaatgagc ctcagcaaag gcaagctagg aggtcgaagg acttccccag     2880
gtgactcggt ctagtctaga gttcgcaaag cctatcctcc ctgtagccgg gtgccaagca     2940
gcctcgagcc tgctccccag cccacctgcc aacaaaaggc gccctccgac tgcaacccag     3000
ccctccacag acaggacccg ccctttcccg aagtcataag acaaagagag tgcatcactg     3060
ctgaaacagt gggcgcacac gagccccaaa gctagagaaa agctggacgg ggctggggc      3120 ggggtgcagg ggtggagggg cggggaggcg ggctccggct gcgccacgct atcgagtctt     3180 ccctcccctcc ttctctgccc cctccgctcc cgctggagcc ctccacccta caagtggcct     3240
acagggcaca ggtgaggcgg gactggacag ctcctgcttt gatcgccgga gatctgcaaa     3300
ttctgcccat gtcgggctgc agagcactcc gacgtgtccc atagtgtttc caaacttgga     3360
aagggcgggg gagggcggga ggatgcggag gcggaggta tgcagacaac gagtcagagt     3420
```

```
ttcccccttga aagcctcaaa agtgtccacg tcctcaaaaa gaatggaacc aatttaagaa    3480
gccagccccg tggccacgtc cctaccgggt tggtaccgag ctcaataatg acgtatgttc    3540
ccatagtaac gccaataggg actttccatt gacgtcaatg ggtggagtat ttacggtaaa    3600
ctgcccactt ggcagtacat caagtgtatc atatgccaag tacgccccct attgacgtca    3660
atgacggtaa atggcccgcc tggcattatg cccagtacat gaccttatgg gactttccta    3720
cttggcagta catctacgta ttagtcatcg ctattaccat ggtgatgcgg ttttggcagt    3780
acatcaatgg gcgtggatag cggtttgact cacggggatt tccaagtctc cacccattg    3840
acgtcaatgg gagtttgttt tgggtaccaa cccggtattc gctccctcct ctgcgccccc    3900
gcaggctcct cccagctgtg gctgcccggg ccccagccc cagccctccc attggtggag    3960
gccctttttgg aggcacccta gggccaggga aacttttgcc gtataaatag gcagatccg    4020
ggctttatta ttttagcacc acggcagcag gaggtttcgg ctaagttgga ggtactggcc    4080
acgactgcat tcccgcgccc gccatttgat acctccgccg gtgacccagg gctctgcgac    4140
acaaggagtc gcatttctaa gtgctagaca aaaggccggc gccgccttcc gcctgcccgc    4200
ctcctgcgcc gcccccttccg aggctaaatc ggctgcgttc ctctcggaac gcgccgcaga    4260
aggggtcctg gtgacgagtc ccgcgttctc tccttgaatc cactcgccag cccgccgccc    4320
tctgccgccg caccctgcac acccgcccct ctcctgtgcc aggtgagcgc ccctcttcac    4380
gtgcggggac cagggaccgt ggagagggat cttggggggca gtggcgggtt gggcgtccgc    4440
gtggaggcct cccccatccc atgccagcgt ctccccacta ccaggcacac acaggctccc    4500
cggcccctcc agcctgaggt cctctaactg cgcaatgcag cggctgcgcg cgctgagtca    4560
tggcggggga ggaagccgga cgagatgaag gaccattctc ccccttttct tgcagggacc    4620
cctgtggcaa aggattaggg ccccttagcc ctggcgggga tcctaagagg cagtgagggg    4680
tgggggccgg cccatgtaca gccccagggt tctcgcaagt gggagcttgg ttctgtcct    4740
gggaaacggg gcgcccttcg cgaggaggga accccctccg cggtgcttga tgcccccttta    4800
acactttccc tgtctctcct tatcgggcga ccttgattct gagcccggaa cagctgcagc    4860
catgcgaagc gacgggagca ttttttcaggg gaaggcgctt gctcctccac gttcttgccc    4920
cgtaggaaca gtgacgatgg caaagcttac cgctttcctc gcctcgggct agggcttgtt    4980
ccgccgccct ttcctgggct tctccttgct ctcttatatt tttcctaatg cccctttcct    5040
accacccgcc ccctcccttg tggggaaaag cctgaccttg ggatgtcctt gaagccttgg    5100
agcccgggcc agccctggga tcttgagggg attggaagga acaccccagt ggcagtcaga    5160
agagctgggt tctaatctca gatctggctc cggggttgct gtgtggcttg aagcacagac    5220
ctttcccata tctgggccct ttcccacgag ggtgttgggc cctctgcttg attcacgatc    5280
tttacattct aaaatactcc ggttcggttt tgttttcagg caaggtgacc ccatggcaag    5340
gcgcaagcca aagggtccag gcttcaacat gacccacctg tccatggcta tggccttttc    5400
cttttccccca gttgccagtg ggcaactcca ccctcagctg ggcaacaccc agcaccagac    5460
agagttagga aaggtacagg ggcaggccta gcaaagggaa gttgggcgta agagagagct    5520
ggggaccaga agtgccccag ggcctgctgg gtgtggggca gggaggtag gaacatttc    5580
cctgacctcc aggagagggg ccctggtcat cgggagatga tgggaaaccc tagctaacta    5640
gtccttcccc tctgtttcct gtatccagga acttgctact accagcaccg tcgctagcac    5700
gcgtttaatt aagtttaaac gggtggcatc cctgtgaccc ctccccagtg cctctcctgg    5760
```

```
ccctggaagt tgccactcca gtgcccacca gccttgtcct aataaaatta agttgcatca    5820
ttttgtctga ctaggtgtcc ttctataata ttatggggtg gagggggtg gtatggagca    5880 aggggcaagt tgggaagaca acctgtaggg cctgcgggt ctattgggaa ccaagctgga    5940
gtgcagtggc acaatcttgg ctcactgcaa tctccgcctc ctgggttcaa gcgattctcc    6000
tgcctcagcc tcccgagttg ttgggattcc aggcatgcat gactgcagga attcgatatc    6060
aagcttatcg ataagagctt ggctgtggaa tgtgtgtcag ttagggtgtg aaagtcccc    6120 aggctcccca gcaggcagaa gtatgcaaag catgcatctc aattagtcag caaccaggtg    6180
tggaaagtcc ccaggctccc cagcaggcag aagtatgcaa agcatgcatc tcaattagtc    6240
agcaaccata gtcccgcccc taactccgcc catcccgccc ctaactccgc ccagttccgc    6300
ccattctccg ccccatggct gactgatttt ttttatttat gcagaggccg aggccgcctc    6360
ggcctctgag ctattccaga agtagtgagg aggcttttt ggaggcctag gcttttgcaa    6420
aaagctcctc gaggaactga aaaccagaa agttaactgg taagtttagt ctttttgtct    6480
tttatttcag gtcccggatc tgatcaagag acaggatgag gatcgtttcg catgattgaa    6540
caagatggat tgcacgcagg ttctccggcc gcttgggtgg agaggctatt cggctatgac    6600
tgggcacaac agacaatcgg ctgctctgat gccgccgtgt tccggctgtc agcgcagggg    6660
cgcccggttc tttttgtcaa gaccgacctg tccggtgccc tgaatgaact gcaggacgag    6720
gcagcgcggc tatcgtggct ggccacgacg ggcgttcctt gcgcagctgt gctcgacgtt    6780
gtcactgaag cgggaaggga ctggctgcta ttgggcgaag tgccggggca ggatctcctg    6840
tcatctcacc ttgctcctgc cgagaaagta tccatcatgg ctgatgcaat gcggcggctg    6900
catacgcttg atccggctac ctgcccattc gaccaccaag cgaaacatcg catcgagcga    6960
gcacgtactc ggatggaagc cggtcttgtc gatcaggatg atctggacga agagcatcag    7020
gggctcgcgc cagccgaact gttcgccagg ctcaaggcgc gcatgcccga cggcgaggat    7080
ctcgtcgtga cccatggcga tgcctgcttg ccgaatatca tggtggaaaa tggccgcttt    7140
tctggattca tcgactgtgg ccggctgggt gtggcggacc gctatcagga catagcgttg    7200
gctacccgtg atattgctga agagcttggc ggcgaatggg ctgaccgctt cctcgtgctt    7260
tacggtatcg ccgctcccga ttcgcagcgc atcgccttct atcgccttct tgacgagttc    7320
ttctgagcgg gactctgggg ttcgaaatga ccgaccaagc gacgcccaac ctgccatcac    7380
gagatttcga ttccaccgcc gccttctatg aaaggttggg cttcggaatc gttttccggg    7440
acgccggctg gatgatcctc cagcgcgggg atctcatgct ggagttcttc gcccaccccg    7500
ggctcgatcc cctcgcgagt tggttcagct gctgcctgag gctggacgac ctcgcggagt    7560
tctaccggca gtgcaaatcc gtcggcatcc aggaaaccag cagcggctat ccgcgcatcc    7620 atgccccga actgcaggag tggggaggca cgatggccgc tttggtcccg gatccagaca    7680
tgataagata cattgatgag tttggacaaa ccacaactag aatgcagtga aaaaatgct    7740 ttatttgtga atttgtgat gctattgctt tatttgtaac cattataagc tgcaataaac    7800
aagttaacaa caacaattgc attcatttta tgtttcaggt tcaggggggag gtgtgggagg    7860 ttttttaaag caagtaaaac ctctacaaat gtggtatggc tgattatgat ccggctgcct    7920
cgcgcgtttc ggtgatgacg gtgaaaacct ctgacacatg cagctcccgg agacggtcac    7980
agcttgtctg taagcggatg ccgggagcag acaagcccgt cagggcgcgt cagcgggtgt    8040
tggcgggtgt cggggcgcag ccatgaccca gtcacgtagc gatagcggag tgcggccgca    8100
aggatctaaa gccagcaaaa gtcccatggt cttataaaaa tgcatagctt taggagggga    8160
```

```
gcagagaact tgaaagcatc ttcctgttag tctttcttct cgtagacttc aaacttatac    8220
ttgatgcctt tttcctcctg gacctcagag aggacgcctg ggtattctgg gagaagttta    8280
tatttcccca aatcaatttc tgggaaaaac gtgtcacttt caaattcctg catgatcctt    8340
gtcacaaaga gtctgaggtg gcctggttga ttcatggctt cctggtaaac agaactgcct    8400
ccgactatcc aaaccatgtc tactttactt gccaattccg gttgttcaat aagtcttaag    8460
gcatcatcca aactttggc aagaaaatga gctcctcgtg gtggttcttt gagttctcta    8520
ctgagaacta tattaattct gtcctttaaa ggtcgattct tctcaggaat ggagaaccag    8580
gttttcctac ccataatcac cagattctgt ttaccttcca ctgaagaggt tgtggtcatt    8640
ctttggaagt acttgaactc gttcctgagc ggaggccagg gtaggtctcc gttcttgcca    8700
atccccatat tttgggacac ggcgacgatg cagttcaatg gtcgaaccat gatggcagcg    8760
gggataaaat cctcttatcg cgataagctt tttgcaaaag cctaggcctc caaaaaagcc    8820
tcctcactac ttctggaata gctcagaggc cgaggcggcc tcggcctctg cataaataaa    8880
aaaaattagt cagccatggg gcggagaatg ggcggaactg ggcggagtta ggggcgggat    8940
gggcggagtt aggggcggga ctatggttgc tgactaattg agatgcatgc tttgcatact    9000
tctgcctgct ggggagcctg gggactttcc acacctggtt gctgactaat tgagatgcat    9060
gctttgcata cttctgcctg ctggggagcc tgggactttt ccacacccta actgacacac    9120
attccacagc tggttctttc cgcctcagaa ggtacctaac caagttcctc tttcagaggt    9180
tatttcaggc catggtgctg cgccgaattc atcgataccg tcgatccgaa caaacgaccc    9240
aacacccgtg cgttttattc tgtcttttta ttgccgcggc cgctcgacct cgaggggggg    9300
cccggtaccc agcttttgtt ccctttagtg agggttaatt gcgcgcttgg cgtaatcatg    9360
gtcatagctg tttcctgtgt gaaattgtta tccgctcaca attccacaca acatacgagc    9420
cgggagcata aagtgtaaag cctggggtgc ctaatgagtg agctaactca cattaattgc    9480
gttgcgctca ctgcccgctt tccagtcggg aaacctgtcg tgccagctgc attaatgaat    9540
cggccaacgc gcggggagag gcggtttgcg tattgggcgc tcttccgctt cctcgctcac    9600
tgactcgctg cgctcggtcg ttcggctgcg gcgagcggta tcagctcact caaaggcggt    9660
aatacggtta tccacagaat caggggataa cgcaggaaag aacatgtgag caaaaggcca    9720
gcaaaaggcc aggaaccgta aaaaggccgc gttgctggcg ttttttccata ggctccgccc    9780 ccctgacgag catcacaaaa atcgacgctc aagtcagagg tggcgaaacc cgacaggact    9840
ataaagatac caggcgtttc cccctggaag ctccctcgtg cgctctcctg ttccgaccct    9900
gccgcttacc ggatacctgt ccgcctttct cccttcggga agcgtggcgc tttctcatag    9960
ctcacgctgt aggtatctca gttcggtgta ggtcgttcgc tccaagctgg gctgtgtgca   10020 cgaaccccc gttcagcccg accgctgcgc cttatccggt aactatcgtc ttgagtccaa   10080
cccggtaaga cacgacttat cgccactggc agcagccact ggtaacagga ttagcagagc   10140
gaggtatgta ggcggtgcta cagagttctt gaagtggtgg cctaactacg gctacactag   10200
aagaacagta tttggtatct gcgctctgct gaagccagtt accttcggaa aaagagttgg   10260
tagctcttga tccggcaaac aaaccaccgc tggtagcggt ggtttttttg tttgcaagca   10320
gcagattacg cgcagaaaaa aaggatctca agaagatcct ttgatctttt ctacggggtc   10380
tgacgctcag tggaacgaaa actcacgtta agggattttg gtcatgagat tatcaaaaag   10440
gatcttcacc tagatccttt taaattaaaa atgaagtttt aaatcaatct aaagtatata   10500
```

-continued

```
tgagtaaact tggtctgaca gttaccaatg cttaatcagt gaggcaccta tctcagcgat   10560
ctgtctattt cgttcatcca tagttgcctg actccccgtc gtgtagataa ctacgatacg   10620
ggagggctta ccatctggcc ccagtgctgc aatgataccg cgagacccac gctcaccggc   10680
tccagattta tcagcaataa accagccagc cggaagggcc gagcgcagaa gtggtcctgc   10740
aactttatcc gcctccatcc agtctattaa ttgttgccgg gaagctagag taagtagttc   10800
gccagttaat agtttgcgca acgttgttgc cattgctaca ggcatcgtgg tgtcacgctc   10860
gtcgtttggt atggcttcat tcagctccgg ttcccaacga tcaaggcgag ttacatgatc   10920
ccccatgttg tgcaaaaaag cggttagctc cttcggtcct ccgatcgttg tcagaagtaa   10980
gttggccgca gtgttatcac tcatggttat ggcagcactg cataattctc ttactgtcat   11040
gccatccgta agatgctttt ctgtgactgg tgagtactca accaagtcat tctgagaata   11100
gtgtatgcgg cgaccgagtt gctcttgccc ggcgtcaata cgggataata ccgcgccaca   11160
tagcagaact ttaaaagtgc tcatcattgg aaaacgttct cggggcgaaa actctcaag   11220 gatcttaccg ctgttgagat ccagttcgat gtaacccact cgtgcaccca actgatcttc   11280
agcatctttt actttcacca gcgtttctgg gtgagcaaaa acaggaaggc aaaatgccgc   11340
aaaaaaggga ataagggcga cacgaaatg ttgaatactc atactcttcc tttttcaata   11400
ttattgaagc atttatcagg gttattgtct catgagcgga tacatatttg aatgtattta   11460
gaaaaataaa caaatagggg ttccgcgcac atttccccga aaagtgccac ctgacgtcta   11520
agaaaccatt attatcatga cattaaccta taaaaatagg cgtatacga ggccctttcg   11580 tctcgcgcgt ttcggtgatg acggtgaaaa cctctgacac atgcagctcc cggagacggt   11640
cacagcttgt ctgtaagcgg atgccgggag cagacaagcc cgtcagggcg cgtcagcggg   11700
tgttggcggg tgtcggggct ggcttaacta tgcggcatca gagcagattg tactgagagt   11760
gcaccatatg cggtgtgaaa taccgcacag atgcgtaagg agaaaatacc gcatcaggcg   11820
ccattcgcca ttcaggctgc gcaactgttg ggaagggcga tcggtgcggg cctcttcgct   11880
attacgccag ctggcgaaag ggggatgtgc tgcaaggcga ttaagttggg taacgccagg   11940
gttttcccag tcacgacgtt gtaaaacgac ggccagt                            11977
```

<210> SEQ ID NO 6
<211> LENGTH: 905
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (142)..(142)
<223> OTHER INFORMATION: Xaa can be Ile or Val
<220> FEATURE:
<221> NAME/KEY: misc_feature
<222> LOCATION: (174)..(174)
<223> OTHER INFORMATION: Xaa can be Ile or Val
<220> FEATURE:
<221> NAME/KEY: misc_feature
<222> LOCATION: (185)..(185)
<223> OTHER INFORMATION: Xaa can be Asn, Asp, Gln, or Glu
<220> FEATURE:
<221> NAME/KEY: misc_feature
<222> LOCATION: (204)..(204)
<223> OTHER INFORMATION: Xaa can be Phe or Tyr
<220> FEATURE:
<221> NAME/KEY: misc_feature
<222> LOCATION: (216)..(216)
<223> OTHER INFORMATION: Xaa can be Ile or Val
<220> FEATURE:
<221> NAME/KEY: misc_feature

```
<222> LOCATION: (234)..(234)
<223> OTHER INFORMATION: Xaa can be Asn, Asp, Gln, or Glu
<220> FEATURE:
<221> NAME/KEY: misc_feature
<222> LOCATION: (235)..(235)
<223> OTHER INFORMATION: Xaa can be Phe or Tyr
<220> FEATURE:
<221> NAME/KEY: misc_feature
<222> LOCATION: (247)..(247)
<223> OTHER INFORMATION: Xaa can be Asn, Asp, Gln, or Glu
<220> FEATURE:
<221> NAME/KEY: misc_feature
<222> LOCATION: (250)..(250)
<223> OTHER INFORMATION: Xaa can be Leu or Met
<220> FEATURE:
<221> NAME/KEY: misc_feature
<222> LOCATION: (254)..(254)
<223> OTHER INFORMATION: Xaa can be Leu or Met
<220> FEATURE:
<221> NAME/KEY: misc_feature
<222> LOCATION: (299)..(299)
<223> OTHER INFORMATION: Xaa can be Leu or Met
<220> FEATURE:
<221> NAME/KEY: misc_feature
<222> LOCATION: (302)..(302)
<223> OTHER INFORMATION: Xaa can be Ile or Val
<220> FEATURE:
<221> NAME/KEY: misc_feature
<222> LOCATION: (314)..(314)
<223> OTHER INFORMATION: Xaa can be Ile or Val
<220> FEATURE:
<221> NAME/KEY: misc_feature
<222> LOCATION: (326)..(326)
<223> OTHER INFORMATION: Xaa can be Asn, Asp, Gln, or Glu
<220> FEATURE:
<221> NAME/KEY: misc_feature
<222> LOCATION: (329)..(329)
<223> OTHER INFORMATION: Xaa can be Ile or Val
<220> FEATURE:
<221> NAME/KEY: misc_feature
<222> LOCATION: (338)..(338)
<223> OTHER INFORMATION: Xaa can be Phe or Tyr
<220> FEATURE:
<221> NAME/KEY: misc_feature
<222> LOCATION: (347)..(347)
<223> OTHER INFORMATION: Xaa can be Leu or Met
<220> FEATURE:
<221> NAME/KEY: misc_feature
<222> LOCATION: (385)..(385)
<223> OTHER INFORMATION: Xaa can be Phe or Tyr
<220> FEATURE:
<221> NAME/KEY: misc_feature
<222> LOCATION: (399)..(399)
<223> OTHER INFORMATION: Xaa can be Asn, Asp, Gln, or Glu
<220> FEATURE:
<221> NAME/KEY: misc_feature
<222> LOCATION: (401)..(401)
<223> OTHER INFORMATION: Xaa can be Asn, Asp, Gln, or Glu
<220> FEATURE:
<221> NAME/KEY: misc_feature
<222> LOCATION: (412)..(412)
<223> OTHER INFORMATION: Xaa can be Asn, Asp, Gln, or Glu
<220> FEATURE:
<221> NAME/KEY: misc_feature
<222> LOCATION: (420)..(420)
<223> OTHER INFORMATION: Xaa can be Phe or Tyr
<220> FEATURE:
<221> NAME/KEY: misc_feature
<222> LOCATION: (432)..(432)
<223> OTHER INFORMATION: Xaa can be Ile or Val
<220> FEATURE:
<221> NAME/KEY: misc_feature
<222> LOCATION: (476)..(476)
<223> OTHER INFORMATION: Xaa can be Ile or Val
<220> FEATURE:
<221> NAME/KEY: misc_feature
<222> LOCATION: (478)..(478)
<223> OTHER INFORMATION: Xaa can be Asn, Asp, Gln, or Glu
<220> FEATURE:
```

```
<221> NAME/KEY: misc_feature
<222> LOCATION: (486)..(486)
<223> OTHER INFORMATION: Xaa can be Asn, Asp, Gln, or Glu
<220> FEATURE:
<221> NAME/KEY: misc_feature
<222> LOCATION: (521)..(521)
<223> OTHER INFORMATION: Xaa can be Leu or Met
<220> FEATURE:
<221> NAME/KEY: misc_feature
<222> LOCATION: (558)..(558)
<223> OTHER INFORMATION: Xaa can be Leu or Met
<220> FEATURE:
<221> NAME/KEY: misc_feature
<222> LOCATION: (600)..(600)
<223> OTHER INFORMATION: Xaa can be Leu or Met
<220> FEATURE:
<221> NAME/KEY: misc_feature
<222> LOCATION: (602)..(602)
<223> OTHER INFORMATION: Xaa can be Asn, Asp, Gln, or Glu
<220> FEATURE:
<221> NAME/KEY: misc_feature
<222> LOCATION: (603)..(603)
<223> OTHER INFORMATION: Xaa can be Leu or Met
<220> FEATURE:
<221> NAME/KEY: misc_feature
<222> LOCATION: (610)..(610)
<223> OTHER INFORMATION: Xaa can be Ile or Val
<220> FEATURE:
<221> NAME/KEY: misc_feature
<222> LOCATION: (612)..(612)
<223> OTHER INFORMATION: Xaa can be Asn, Asp, Gln, or Glu
<220> FEATURE:
<221> NAME/KEY: misc_feature
<222> LOCATION: (620)..(620)
<223> OTHER INFORMATION: Xaa can be Phe or Tyr
<220> FEATURE:
<221> NAME/KEY: misc_feature
<222> LOCATION: (631)..(631)
<223> OTHER INFORMATION: Xaa can be Asn, Asp, Gln, or Glu
<220> FEATURE:
<221> NAME/KEY: misc_feature
<222> LOCATION: (649)..(649)
<223> OTHER INFORMATION: Xaa can be Asn, Asp, Gln, or Glu
<220> FEATURE:
<221> NAME/KEY: misc_feature
<222> LOCATION: (681)..(681)
<223> OTHER INFORMATION: Xaa can be Asn, Asp, Gln, or Glu
<220> FEATURE:
<221> NAME/KEY: misc_feature
<222> LOCATION: (684)..(684)
<223> OTHER INFORMATION: Xaa can be Asn, Asp, Gln, or Glu
<220> FEATURE:
<221> NAME/KEY: misc_feature
<222> LOCATION: (719)..(719)
<223> OTHER INFORMATION: Xaa can be Asn, Asp, Gln, or Glu
<220> FEATURE:
<221> NAME/KEY: misc_feature
<222> LOCATION: (736)..(736)
<223> OTHER INFORMATION: Xaa can be Asn, Asp, Gln, or Glu
<220> FEATURE:
<221> NAME/KEY: misc_feature
<222> LOCATION: (756)..(756)
<223> OTHER INFORMATION: Xaa can be Asn, Asp, Gln, or Glu
<220> FEATURE:
<221> NAME/KEY: misc_feature
<222> LOCATION: (773)..(773)
<223> OTHER INFORMATION: Xaa can be Asn, Asp, Gln, or Glu
<220> FEATURE:
<221> NAME/KEY: misc_feature
<222> LOCATION: (783)..(783)
<223> OTHER INFORMATION: Xaa can be Asn, Asp, Gln, or Glu
<220> FEATURE:
<221> NAME/KEY: misc_feature
<222> LOCATION: (789)..(789)
<223> OTHER INFORMATION: Xaa can be Phe or Tyr
<220> FEATURE:
<221> NAME/KEY: misc_feature
<222> LOCATION: (825)..(825)
<223> OTHER INFORMATION: Xaa can be Asn, Asp, Gln, or Glu
```

```
<220> FEATURE:
<221> NAME/KEY: misc_feature
<222> LOCATION: (836)..(836)
<223> OTHER INFORMATION: Xaa can be Asn, Asp, Gln, or Glu
<220> FEATURE:
<221> NAME/KEY: misc_feature
<222> LOCATION: (850)..(850)
<223> OTHER INFORMATION: Xaa can be Asn, Asp, Gln, or Glu
<220> FEATURE:
<221> NAME/KEY: misc_feature
<222> LOCATION: (852)..(852)
<223> OTHER INFORMATION: Xaa can be Asn, Asp, Gln, or Glu
<220> FEATURE:
<221> NAME/KEY: misc_feature
<222> LOCATION: (858)..(858)
<223> OTHER INFORMATION: Xaa can be Phe or Tyr
<220> FEATURE:
<221> NAME/KEY: misc_feature
<222> LOCATION: (859)..(859)
<223> OTHER INFORMATION: Xaa can be Asn, Asp, Gln, or Glu
<220> FEATURE:
<221> NAME/KEY: misc_feature
<222> LOCATION: (862)..(862)
<223> OTHER INFORMATION: Xaa can be Asn, Asp, Gln, or Glu
<220> FEATURE:
<221> NAME/KEY: misc_feature
<222> LOCATION: (874)..(874)
<223> OTHER INFORMATION: Xaa can be Asn, Asp, Gln, or Glu
<220> FEATURE:
<221> NAME/KEY: misc_feature
<222> LOCATION: (878)..(878)
<223> OTHER INFORMATION: Xaa can be Asn, Asp, Gln, or Glu
<220> FEATURE:
<221> NAME/KEY: misc_feature
<222> LOCATION: (888)..(888)
<223> OTHER INFORMATION: Xaa can be Leu or Met

<400> SEQUENCE: 6

Gly Val Glu Ile Thr Glu Gly Val Thr Val Thr Ala Lys Gly Asn Thr
1               5                   10                  15

Glu Gly Asn Thr Ala Asp Leu Ala Ile Asp Gly Asp Leu Ser Thr Tyr
            20                  25                  30

Trp Glu Ser Ser Asn Asp Tyr Lys Trp Ile Glu Val Asp Leu Gly Gly
        35                  40                  45

Ile Tyr Glu Leu Ser Lys Ile Glu Ile Phe Asn Lys Asp Glu Ala Val
50                  55                  60

Tyr Lys Tyr Asn Ile Tyr Ala Ser Glu Asp Gly Glu Asn Phe Asn Lys
65                  70                  75                  80

Ile Ala Tyr Lys Asn Asn Asp Asn Val Ser Asp Ser Asn Gly Asn Met
                85                  90                  95

His Thr Ile Asp Asn Val Arg Ala Gly Lys Ile Arg Ile Asp Val Val
            100                 105                 110

Gln Asn Ser Asn Ser Asp Arg Val Asn Ile Ala Glu Ile Asn Val Phe
        115                 120                 125

Gly Lys Asn Thr Gly Glu Ser Leu Pro Glu Met Glu Ala Xaa Ala Thr
    130                 135                 140

Ala Ala Ala Ser Glu Thr Leu Leu Ala Ala Glu Ala Glu Gly Ala Ala
145                 150                 155                 160

Gly Asp Glu Ala Arg Ala Ala Ala Thr Arg Ala Glu Xaa Ala Arg
                165                 170                 175

Leu Leu Gly Arg Gly Ile Ala Ala Xaa Phe Lys Asp Lys Phe Glu Arg
            180                 185                 190

Ala Ile Ala Ala Gln Leu Asn Gly Asn Asp Thr Xaa Glu Leu Gly Asp
        195                 200                 205

Gly Gly Ala Ala Arg Val Arg Xaa Arg Gly Asn Asn Gly Val Ala Ala
```

```
                210                 215                 220
Ala Ala Gly Leu Asn Arg Tyr Leu Arg Xaa Xaa Cys Asn Cys Ser His
225                 230                 235                 240

Asn Ala Ile Met Gly Ser Xaa Leu Arg Xaa Pro Arg Pro Xaa Pro Ala
                245                 250                 255

Val Gly Glu Arg Leu Thr Glu Ala Thr Pro Asn Arg His Arg Tyr Ala
            260                 265                 270

Gln Asn Phe Cys Thr Gln Ser Tyr Ser Met Ser Phe Trp Asp Trp Ala
            275                 280                 285

Arg Trp Glu Arg Glu Ile Asp Trp Cys Ala Xaa Asn Gly Xaa Asn Leu
        290                 295                 300

Ala Leu Ala Ile Ile Gly Gln Glu Ala Xaa Leu Arg Arg Thr Leu Asn
305                 310                 315                 320

Ala Leu Gly Leu Ser Xaa Ala Glu Xaa Asn Glu Phe Ile Ser Gly Pro
                325                 330                 335

Ala Xaa Leu Ala Trp Gly Arg Met Gln Asn Xaa His Gly Phe Asp Gly
            340                 345                 350

Pro Leu Pro Asn Asp Trp His Glu Gln Arg Ala Glu Leu Gln Arg Arg
        355                 360                 365

Met His Asp Arg Met Arg Ser Phe Gly Ile Asn Pro Val Leu Gln Ala
370                 375                 380

Xaa Ala Gly His Val Pro Arg Ala Phe Lys Arg Lys Asn Gln Xaa Ala
385                 390                 395                 400

Xaa Thr Ile Lys Gln Gly Gly Trp Cys Gly Phe Xaa Arg Pro Asp Met
                405                 410                 415

Cys Lys Ser Xaa Leu Asn Ala Gly Glu Ala Asp Ile Phe Gln Ile Xaa
            420                 425                 430

Ala Asp Leu Phe Leu Arg Glu Gln Ile Glu Glu Phe Gly Asp Thr Asp
            435                 440                 445

Asn Ile Tyr Gly Ala Asp Pro Phe Asn Glu Gly Gln Asn Pro Gly Asp
        450                 455                 460

Glu Asp Asn Tyr Leu Ala Ala Ala Thr Glu Ala Xaa Gln Xaa Ala Met
465                 470                 475                 480

Ile Ala His Asp Asn Xaa Ala Val Trp Leu Ile Gln Asn Trp Gln Phe
                485                 490                 495

Gln His Gln Pro Gln Phe Trp Gly Asn Ala Gln Asn Arg Ala Leu Glu
            500                 505                 510

Gly Ala Thr Lys Arg Asp Arg Ala Xaa Val Leu Asp Leu Phe Ala Glu
        515                 520                 525

Ser Gln Pro Asp Trp Asn Arg Leu Ala Glu Phe Arg Asp Gln Pro Phe
530                 535                 540

Ile Trp Asn Met Leu His Asn Phe Gly Gly Arg His Gly Xaa Asp Ala
545                 550                 555                 560

Ala Leu Glu Ala Leu Ala Gly Glu Ile Glu Ala Ala Arg Leu Ala Asn
                565                 570                 575

Asn Glu His Met Val Gly Ile Gly Ile Ala Pro Glu Ala Ile Asn Gln
            580                 585                 590

Asn Glu Leu Ala Tyr Glu Leu Xaa Ala Xaa Xaa Ala Trp Arg Arg Asp
        595                 600                 605

Gln Xaa Pro Xaa Leu Ala Ala Trp Thr Glu Asp Xaa Ala Ala Arg Arg
    610                 615                 620

Tyr Gly Lys Ser Asn Lys Xaa Ala Gly Ala Ala Trp Arg Ile Ile Leu
625                 630                 635                 640
```

-continued

```
Arg Ser Ala Tyr Asn Cys Arg Asn Xaa Ala Cys Arg Gly Ala Ala Arg
            645             650             655

Ser Ile Ile Asn Ala Arg Pro Gly Leu Gln Ile Asn Ser Ala Ser Thr
            660             665             670

Trp Gly His Ser Lys Ile Trp Tyr Xaa Arg Ser Xaa Phe Glu Glu Ala
            675             680             685

Ile Arg Ile Leu Ala Lys Asn Ala Asp Glu Leu Ala Asp Ser Asp Ala
    690             695             700

Phe Arg Tyr Asp Leu Ala Asp Ile Leu Arg Gln Ala Leu Ala Xaa Leu
705             710             715             720

Ala Gln Glu Tyr Tyr Glu Glu Ala Arg Asn Ala Tyr Asn Asn Gly Xaa
            725             730             735

Gly Ala Lys Leu Leu Arg Ala Gly Gly Lys Leu Ala Tyr Glu Leu Ile
            740             745             750

Lys Ala Gln Xaa Arg Val Leu Ala Ser Arg Pro Arg Phe Leu Ile Gly
            755             760             765

Asn Trp Ile Glu Xaa Ala Arg Ala Ala Ala Lys Asp Glu Ala Xaa Trp
    770             775             780

Thr Ala Asp Leu Xaa Glu Gln Asn Ala Arg Ala Gln Leu Thr Leu Trp
785             790             795             800

Gly Pro Arg Asn Asn Ala Asp Gly Gly Gly Ile Leu Asp Tyr Ala Asn
            805             810             815

Arg Gln Leu Ala Gly Leu Thr Ala Xaa Tyr Tyr Thr Ala Arg Trp Arg
            820             825             830

Leu Phe Ile Xaa Ala Leu Gln Ala Glu Leu Ala Gln Gly Ala Lys Ala
            835             840             845

Gln Xaa His Xaa Phe Asp Lys Asn Glu Xaa Xaa Leu Glu Xaa Ala Lys
    850             855             860

Ser Asp Ser Asp Gln Arg Tyr Pro Ser Xaa Ala Arg Asn Xaa Asn Leu
865             870             875             880

Asp Glu Ala Ala Lys Ile Ala Xaa Glu Ser Tyr Pro Gly Thr Asn Ala
            885             890             895

Asp Lys Ile Leu Gly Glu Asn Glu Ser
            900             905
```

CRYSTAL STRUCTURE OF HUMAN α-N-ACETYLGLUCOSAMINIDASE

RELATED APPLICATIONS

This application is a continuation of and claims priority under 35 U.S.C. §120 to U.S. application, U.S. Ser. No. 13/136,092, filed Jul. 22, 2011, which claims priority under 35 U.S.C. §119(e) to United States provisional patent application, U.S. Ser. No. 61/366,694, filed Jul. 22, 2010, the entire contents of each of which is incorporated herein by reference in their entirety.

BACKGROUND OF THE INVENTION

Sanfilippo syndrome type B (mucopolysaccharidosis III B (MPS III-B)) is a rare autosomal recessive lysosomal storage disorder. Sanfilippo syndrome type B caused by deficiency of α-N-acetylglucosaminidase (NAGLU), one of the enzymes required for the lysosomal degradation of the glycosaminoglycan heparan sulfate. Heparan sulfate is normally found in the extracellular matrix and on cell surface glycoproteins. NAGLU degrades heparan sulfate by hydrolysis of terminal N-acetyl-D-glucosamine residues in N-acetyl-alpha-D-glucosaminides. The enzyme deficiency leads to the accumulation of heparan sulfate in various organs. The incidence of Sanfilippo syndrome type B is about 0.4 per 100,000 births. Sanfilippo syndrome type B is biochemically characterized by the lysosomal accumulation and urinary excretion of heparan sulfate. The disease initially manifests as aggressiveness and hyperactivity in humans between the ages of 2 and 6 years, later progressing to mental retardation and CNS degeneration, and ultimately death in early adulthood.

Sanfilippo syndrome type B displays wide clinical variability that is likely caused by a high degree of molecular heterogeneity of the NAGLU gene, with more than 100 different mutations in the naglu gene, ranging from small deletions and insertions to nonsense and missense mutations, that have been identified to date. Biochemical studies have confirmed the deleterious effects of many of these mutations (Yogalingam et al. (2001) *Hum Mutat* 18:264-281; Beesley et al. (2005) *J Inherit Metab Dis* 28:759-767; Beesley et al. (1998) *J Med Genet* 35:910-914; Emre et al. (2002) *Hum Mutat* 19:184-185; Tanaka et al. (2002) *J Hum Genet* 47:484-487; Tessitore et al. (2000) *Hum Genet* 107: 568-576; Schmidtchen et al. (1998) *Am J Hum Genet* 62:64-69; Bunge et al. (1999) *J Med Genet* 36:28-31; Weber B, et al. (1999) *Eur J Hum Genet* 7:34-44, and referenced in Table 4). Despite having been cloned over ten years ago and having been studied for more than twenty years, no structural or mechanistic data for mammalian NAGLU have been obtained, hindering the development of potential therapeutic strategies to treat patients suffering from mucopolysaccharidosis III B (MPS III-B). Treatment today is largely supportive. There is currently no cure for Sanfilippo syndrome type B.

SUMMARY OF THE INVENTION

Many diseases are thought to be associated with protein misfolding, such as cystic fibrosis, amyloidoses, Parkinson's disease, Alzheimer's disease, Lou Gehrig's disease, or protein-destabilization, such as Gaucher disease and Sanfilippo syndrome type B (mucopolysaccharidosis III B), which are autosomal-recessive lysosomal storage disorders. Sanfilippo syndrome type B mucopolysaccharidosis III B (MPS III-B) is caused by impaired activity of α-N-acetylglucosaminidase (NAGLU). The impaired activity of NAGLU is caused by protein destabilizing mutations in the gene for naglu. More than a hundred mutations are known for NAGLU. However, very few of these mutations affect amino acid residues in the active site of the enzyme. Most of the disease-causing mutations occur throughout the protein and lead to an unstable NAGLU protein form that is either degraded in the lysosome, where NAGLU normally functions, or the unstable, mutated protein fails to exit the endoplasmic reticulum (ER). Enzyme replacement therapy using injections of the normal enzyme may under certain circumstances alleviate some of the symptoms associated with disease. However, the injected enzyme does not necessarily reach every affected organ system (e.g. passing the blood-brain barrier) and such treatment is usually difficult and very expensive. Before the present invention, no structural information was available for NAGLU, largely due to the difficulty of generating enough pure homogeneous protein for structural studies and to the difficulties in generating crystals of sufficient quality for X-ray diffraction studies given heterogeneous glycosylation of the protein. Recently, Ficko-Blean et al. (2008) *Proc Natl Acad Sci USA*, 105(18): 6560-6565 reported the crystal of the protein structure of a bacterial homolog of NAGLU, CpGH89, which shares about 30% sequence identity with NAGLU. The structure of the bacterial homolog provided some understanding of the enzymatic function of NAGLU. However, the atomic level structural information of the human form (NAGLU) had not been obtained before the present invention. This information is crucial for understanding the effects of pathogenic mutations on the activity of this important enzyme in humans and provides structure-function relationships that allow for the design of novel therapeutic strategies to treat mucopolysaccharidosis III B (MPS III-B).

Aspects of the invention are based at least in part on the crystallization and determination of the structure of α-N-acetylglucosaminidase and the identification of active portions or fragments of α-N-acetylglucosaminidase (collectively herein referred to as "NAGLU") that can be utilized in developing therapeutics. In certain embodiments, the invention provides methods for identifying or designing compounds that bind NAGLU using the structural information provided herein. In other embodiments, the invention provides methods of crystallizing NAGLU and methods of expressing and purifying NAGLU. In certain embodiments, the invention provides isolated α-N-acetylglucosaminidase (NAGLU) having altered glycosylation patterns as compared to native NAGLU. In certain embodiments, the invention provides nucleic acids (including vectors) encoding NAGLU and host cells expressing NAGLU. The atomic coordinates provided herein for NAGLU and the three dimensional structural models that may be generated using the atomic coordinates provided herein can be useful for the identification, characterization and/or molecular modeling (design) of NAGLU binding compounds that stabilize the NAGLU protein to increase or restore (at least partially) NAGLU enzymatic activity in cells that have reduced or missing NAGLU enzymatic activity. In certain embodiments, the binding compound comprises chemical or biological chaperones. NAGLU binding compounds may be useful to treat Sanfilippo syndrome type B (mucopolysaccharidosis III B) in a subject having the disease and being in need of such treatment. Such therapies involving chaperoning of NAGLU may be as effective as proposed gene therapy, easier to implement, and/or more cost effective. NAGLU binding compounds may also be useful for other applications, such as scientific research, e.g., as stabilizing agents in crystallography. Some uses may involve small-molecule chaperoning of NAGLU, for example, in vitro. For example, one therapeutic approach in treating MPS III-B involves enzyme replacement therapy, where it is proposed to inject isolated or recombinantly produced wild-type NAGLU into subjects suffering from Sanfilippo syndrome type B. Some uses may involve biological chaperoning of NAGLU by, for example, binding or linking NAGLU to an amino acid sequence such as, for example, an antibody or fragment thereof. Such chaperones may be used to direct and/or shuttle the NAGLU binding compound to a particular location and/or target, such as across the blood brain barrier and/or for takeup into a lysosome. NAGLU binding compounds as described herein may be used to stabilize isolated or recombinantly produced wild-type NAGLU, which may be relatively unstable, both during purification/manufacture and in storage. It is known in the art that injected human proteins can cause an immune responses induced by mis-folded proteins in the preparation (Maas et al. (2007) *J. Biol. Chem.* 282:2229-2236). NAGLU binding compounds as identified using the atomic coordinates provided herein may be included in the manufacture and storage of NAGLU to reduce or eliminate these problems. Combining the NAGLU binding compound with the isolated NAGLU enzyme during treatment may also improve in vivo stability and/or bioavailability, and may reduce the need for frequent dosing.

Aspects of the invention relate to methods of identifying a NAGLU polypeptide binding compound. Such compounds may be for example computationally identified using the atomic coordinates set forth in Table 3 and displaying the atomic coordinates to form a three-dimensional structure of the NAGLU polypeptide. Three-dimensional structures of NAGLU variants, such as NAGLU mutants comprising amino acid substitution, deletion or duplication that are associated with or lead to mucopolysaccharidosis III B (MPS III-B), such as provided in Table 4, may also be modeled using the three-dimensional structure based on the atomic coordinates provided herein as a template. NAGLU binding compounds may be small molecules and may act as chemical chaperones, having a stabilizing effect on NAGLU. NAGLU binding compounds may bind to the active site of NAGLU, for example as an inhibitor, which may be a reversible inhibitor, or as substrate. NAGLU binding compounds may also bind outside of the active site of NAGLU (exosites). Exosites that are suitable for NAGLU stabilization may comprise a mutation (e.g. substitution, deletion or duplication) that is associated with or leads to mucopolysaccharidosis III B (MPS III-B). Suitable exosites may also be adjacent or in close proximity to NAGLU mutations. Proximity may be determined based on either the primary structure, secondary structure or tertiary structure of the polypeptide. Binding compounds may be designed in silico and may be designed from a known compound. Binding compounds may be tested in vitro or in vivo for their ability to bind to the NAGLU polypeptide, to stabilize the NAGLU polypeptide and/or to modulate the enzymatic activity of the NAGLU polypeptide. For example, biological assays may be used to determine if the binding compound a) modulates the enzymatic activity, b) modulates the stability, and/or c) modulates intracellular trafficking of a mutated NAGLU polypeptide when bound to the mutated NAGLU polypeptide compared to a mutated NAGLU polypeptide that is not bound by the chemical chaperone. Suitable binding compounds may be selected based on their ability to increase the activity, stability, or intracellular trafficking of mutated NAGLU polypeptide. Any of the aforementioned methods may also be suitable to identify drug candidate test compounds for the treatment of mucopolysaccharidosis III B (MPS III-B).

Aspects of the invention relate to computer-assisted methods for identifying potential NAGLU polypeptide binding compounds, using a programmed computer comprising a processor, a data storage system, an input device, and an output device. Such methods may involve, for example, a) inputting into the programmed computer through an input device data comprising the atomic coordinates of a subset of the atoms generated from a complex of NAGLU and a binding compound, thereby generating a criteria data set; b) comparing, using the processor, the criteria data set to a computer database of chemical structures stored in the computer data storage system; c) selecting from the database, using computer methods, chemical structures having a portion that is structurally similar to said criteria data set; and d) outputting to an output device the selected chemical structures having a portion similar to said criteria data set. Such methods may also be employed using computationally represented the three-dimensional models that include altered structural information, wherein one or more of the locations of known NAGLU polypeptide amino acid mutations that are associated with or lead to mucopolysaccharidosis III B (MPS III-B) as set forth in Table 4 are modeled into the structure that is based on the atomic coordinates provided in Table 3, or a suitable subset thereof. NAGLU variants, such as NAGLU homologs or orthologs may also be modeled into the structure that is based on the atomic coordinates provided in Table 3, or a suitable subset thereof. The aforementioned computer-assisted methods may be used to identify potential NAGLU variant polypeptide binding compounds. Aspects of the invention relate to computer readable media comprising the atomic coordinates for a NAGLU polypeptide (e.g. as set forth in Table 3) or a subset thereof, optionally further comprising programming for displaying a molecular model of the NAGLU polypeptide, programming for identifying a chemical chaperone that binds to the NAGLU polypeptide and/or further comprising a database of structures of drug candidate test compounds. Such test compounds may, for example, be based on known inhibitors, activators or substrates of lysosomal glycosidases. Aspects of the invention relate to computers comprising any of the afore-mentioned computer-readable media, as well as computer systems comprising a memory comprising x-ray crystallographic structure coordinates defining the NAGLU polypeptide as set forth in Table 3 and a processor in electrical communication with the memory. The processor may generate a molecular model having a three dimensional structure representative of at least a portion of said NAGLU polypeptide, or a variant thereof.

Aspects of the invention relate to methods of obtaining a purified recombinant NAGLU polypeptide with an altered glycosylation pattern compared to native NAGLU. NAGLU polypeptides comprising amino acids 24-743 of the amino acid sequence set forth in SEQ ID NO: 1 contain six asparagine (N) residues N261, N272, N435, N503, N526, and N532 that are suitable for N-linked glycosylation. The methods provided may involve a) expressing a recombinant NAGLU polypeptide in a host cell (for example a mammalian host cell), b) treating the host cell with a glycosidase inhibitor (for example a mannosidase inhibitor, such as kifunensine), and c) purifying a NAGLU polypeptide (e.g. using chromatographic methods, such as column chromatography). In certain embodiments, the NAGLU polypeptide is secreted from the mammalian cells and may be purified from the culture medium. Purified or isolated NAGLU polypeptides may comprise the amino acid sequence set forth in SEQ ID NO: 3 and further, the amino acid sequence may comprises one or more amino acid substitutions, deletions, and/or additions as set forth in Table 4 compared to wild-type human NAGLU amino acid sequence. The invention also provides NAGLU polypeptides with altered glycosylation patterns, one of such is NAGLU-kif, which is purified or isolated NAGLU polypeptide expressed in a host cell that was treated with kifunensine.

Further aspects of the invention relate to crystalline forms of NAGLU polypeptide, such as those having a crystal that is characterized with space group $P6_3$ and has unit cell parameters of a=b=205.66 Å, c=78.69 Å or a=b=207.5 Å, c=79.6 Å, or a=b=205.13 Å, c=78.44 Å and bond angles of $\alpha=\beta=90°$, $\gamma=120°$. These crystals may diffract x-rays for the determination of structure coordinates to a resolution of between approximately 2.4 Å and approximately 3.5 Å and can have different sizes, such as, for example, crystals of a size of approximately 100×20×20 micron or crystals of a size of approximately 150×50×50 micron, or other sizes. Further, the invention provides methods for obtaining a crystal. These methods may involve the afore-mentioned production and purification methods and further involve concentrating a solution of purified NAGLU polypeptide to a polypeptide concentration at which the NAGLU polypeptide precipitates and forms crystals. The NAGLU polypeptide concentration in solution at which the NAGLU polypeptide precipitates and forms crystals may be about 0.5 mg/ml, about 1 mg/ml, about 1.5 mg/ml, or about 2 mg/ml. Aspects of the invention further provide methods for cryoprotecting crystals.

The invention further provides a vector comprising the nucleic acid sequence of NAGLU as set forth in SEQ ID NO: 5 and host cells that comprise a NAGLU expression vector.

All references cited herein, including patents, published patent applications, and publications, are incorporated by reference in their entirety.

DEFINITIONS

Accessory binding site: The term "accessory binding site" comprises any binding site other than the active site. An "allosteric binding site" is an accessory binding site which facilitates a change in the conformation and/or activity of the enzyme upon being bound by an allosteric effector. Accessory binding sites may be identified by solving substrate/product bound crystal structures and comparing the obtained structures with the structure of the apo enzyme described herein.

Active site: The active site of an enzyme refers to the catalytic site of the enzyme (i.e., where the reaction catalyzed by the enzyme occurs). The structure and chemical properties of the active site allow the recognition and binding of a binding compound or substrate. The active site typically includes residues responsible for the binding specificity (e.g., charge, hydrophobicity, and/or steric hindrance) and catalytic residues of the enzyme. The term "active site," as used herein, comprises, for example, the following sites in NAGLU: the site where degradation of heparan sulfate occurs (e.g., heparin sulfate), particularly binding sites for N-acetylglucosamine (NAG). In certain embodiments, the active site may be defined as consisting of three regions: the entrance to the active site, the substrate binding site, and the catalytic core. The entrance to the NAGLU active site is at the cleft between domains II and III. Some of the residues found to be at the entrance are $H_{270}$, $Q_{355}$, $H_{356}$, $Q_{359}$, $R_{510}$, and $R_{519}$. Further past the entrance to the active site of NAGLU is the substrate binding site. The core of the NAGLU active site is defined by residues $N_{134}$, $C_{136}$, $Y_{140}$, $W_{201}$, $M_{204}$, $W_{268}$, $N_{315}$, $E_{316}$, $W_{35}2$, $L_{383}$, $L_{407}$, $F_{410}$, $E_{446}$, $H_{512}$, $W_{649}$, $I_{655}$, and $Y_{658}$. These residues are located within 5 Å of the product molecule (N-acetylglucosamine) as it was modeled in the active site. $H_{512}$ may occur in multiple conformations. The three-dimensional structure of the active site of human NAGLU is provided by the atomic coordinates listed in Table 3 and atomic coordinates for the active site are provided in Table 5.

Amino acid residues in peptides shall herein after be abbreviated as follows: phenylalanine is Phe or F; leucine is Leu or L; isoleucine is Ile or I; methionine is Met or M; Valine is Val or V; serine is Ser or S; proline is Pro or P; Threonine is Thr or T; Alanine is Ala or A; Tyrosine is Tyr or Y; histidine is His or H; glutamine is Gln or Q; asparagine is Asn or N; lysine is Lys or K; aspartic acid is Asp or D; glutamic Acid is Glu or E; cysteine is Cys or C; tryptophan is Trp or W; arginine is Arg or R; and glycine is Gly or G. For further description of amino acids, see *Proteins: Structure and Molecular Properties* by Creighton T. E. (1983) W. H. Freeman & Co., New York, incorporated herein by reference.

The term "altered glycosylation pattern" or "altered glycan pattern" refers to a glycan pattern on a protein which is different from that of a native protein. A polypeptide exhibits an altered glycan pattern when one or more monosaccharide units that are part of the glycan structure on this polypeptide differ from that of a native protein. For example, the native polypeptide may exhibit a complex glycan (e.g., having branched glycans with terminal galactosyl and/or sialyl residues). A polypeptide having an altered glycan pattern may be a polypeptide exhibiting hybrid glycans, high mannose glycans, or no discernable glycan structure. It should be appreciated that the converse also applies, e.g. the native protein is non-glycosylated, while the protein having an altered glycosylation pattern is glycosylated.

Atomic coordinates: The term "atomic coordinates" refers to mathematical coordinates derived from mathematical equations related to the patterns obtained on diffraction of a monochromatic beam of X-rays by the atoms (scattering centers) of a protein molecule in crystal form. The diffraction data are used to calculate an electron density map of the repeating unit of the crystal. The electron density map is then used to establish the positions of the individual atoms within the unit cell of the crystal. The coordinates can also be obtained by means of computational analysis.

Binding compound: As used herein, a "binding compound" refers to a compound which reversibly or irreversibly binds to NAGLU. In certain embodiments, the binding compound binds in an active site of NAGLU. A binding compound may be an inhibitor of NAGLU (i.e., eliciting inhibition or reduction in enzymatic activity), an activator of NAGLU (i.e., eliciting an increase in enzymatic activity), a stabilizer (i.e., may elicit a change in stability of NAGLU). Inhibitor compounds can, for example, be substrate analogs (e.g., heparin sulfate analogs derived from heparan sulfate analog libraries produced chemicoenzymatically or semi-synthetically from heparin (Yates et al., *J. Med. Chem.,* 2004, 47(1):277-280) or synthetic heparan sulfate analogs (Ikedaa et al., *Carbohydrate Res.,* 2008, 343(40:587-595)). A stabilizer compound can be, for example, a reversible inhibitor. In certain embodiments, the binding compound binds to a site of a mutated NAGLU that has an amino acid sequence that is different from that of wild-type NAGLU. Such changes may result in an altered stability of the mutated NAGLU or an altered intracellular localization. The binding compound, such as a chemical chaperone, may elicit stabilization of mutated NAGLU by stabilizing the conformation of the enzyme. As a consequence, in certain embodiments, such stabilized mutated NAGLU may not undergo rapid degradation, may have higher enzymatic activity, or may be localized in the correct intracellular compartment as compared to the non-stabilized form.

Biological chaperone. As used herein, the term "biological chaperone" refers to a chaperone that comprises or consists of a biomolecule, for example, a protein or a nucleic acid. In some embodiments, a biological chaperone is a protein that stabilizes, assists in the folding or unfolding and/or the assembly or disassembly of another molecule or macromolecular structure, for example, of a protein or nucleic acid, or a molecule or molecule complex comprising a protein or a nucleic acid. In some embodiments, a biological chaperone protects a molecule, for example, a protein or nucleic acid molecule, from undesired association or binding until a desired binding/association partner is available or a certain folding state has been achieved. Typically, a biological chaperone is not included in the mature structure, for example, the folded protein, that it stabilizes, or that it assists in the assembly, disassembly, folding, or unfolding of. Biological chaperones are well known to those of skill in the art and include, but are not limited to, proteins, polypeptides, antibodies (e.g., human antibodies, mouse antibodies, camelid antibodies, shark antibodies (e.g., IgNARs) or fragments thereof), and alternative protein scaffolds, for example, scaffolds with dual binding domains, fibronectin type III domains, or designed ankyrin repeat modules. Additional biological chaperones are well known to those of skill in the art, and the invention is not limited in this respect. For a description of some non-limiting examples of biological chaperones, see, e.g., Shohei Koide, *Engineering of recombinant crystallization chaperones, Curr. Opin. Struct. Biol.* 2009 August; 19(4):499-57, the entire contents of which are incorporated herein by reference.

Chemical chaperone: The term "chemical chaperone" as used herein refers to non-proteinacious chaperones, such as small molecules that function as chaperones, for example, to protect a nascent polypeptide chain from undesirable associations in the cellular environment until proper folding is completed (e.g., stabilizing the transition state of protein folding or a high-energy folding intermediate thereby increasing the rate of folding), to stabilize an already folded polypeptide by binding to it and/or to protect the folded polypeptide against stress, such as thermal denaturation and proteolytic degradation. Chemical chaperones can be non-specific, such as, for example, glycerol and trehalose, which can bind to and stabilize a large number of proteins through non-site specific binding. Specific chemical chaperones are designed specifically bind to a desired target polypeptide. Chemical chaperones may associate and stabilize the target polypeptide through a variety of chemical interactions, such as electrostatic, van der Waals, and hydrogen bonding (Ringe, D. (2009) *Journal of Biology* 8:80).

By "choosing" is meant picking a chemical or biological compound from a chemical or biological library or commercially available source.

By "design" or "designing" is meant to provide a novel molecular structure of, for example, a compound, such as a small molecule, a polypeptide, amino acid, nucleic acid or fragments thereof that has desired properties or characteristics.

The term "glycan" refers to a class of carbohydrates consisting of a number of monosaccharides joined by glycosidic bonds that may be attached to a glucoconjugate, such as a glycoprotein, a glycolipid, or a proteoglycan. Glycans may be unbranched or branched and may comprise one, two, or more kinds of monosaccharides.

By "identify" or "identifying" is meant to determine a condition, compound, polypeptide, amino acid, nucleic acid and/or variations or fragments of such, that corresponds to or exhibits a desired characteristic or property.

The term "modulate," as used herein, means to increase or decrease NAGLU enzymatic activity and/or stability.

NAGLU ($\alpha$-N-acetylglucosaminidase): As used herein "NAGLU" refers to $\alpha$-N-acetylglucosaminidase and/or fragments thereof, for example, human native (naturally occurring) $\alpha$-N-acetylglucosaminidase and/or fragments thereof, wild-type $\alpha$-N-acetylglucosaminidase (SEQ ID NO.: 1) and/or fragments thereof, and any structural modifications thereof. Structural modifications include any additions, deletions, and/or substitutions to the native NAGLU amino acid sequence, of bound glycans, such as N-glycans, and/or of coordinating solvates, hydrates, or non-covalently bound ligands/substrates (e.g., heparan sulfate). Such structurally modified NAGLU are referred herein also as "NAGLU variant" or "NAGLU variants." As used herein, a "variant" of NAGLU is a polypeptide which contains one or more modifications to the primary amino acid sequence of a naturally occurring NAGLU polypeptide. Structurally modified NAGLU or variant NAGLU include NAGLU that comprise one or more amino acid additions, deletions, and/or substitutions that are associated with mucopolysaccharidosis III B (MPS III-B). Such structurally modified NAGLU are referred herein also as "NAGLU mutant(s)" or "mutant NAGLU." In certain embodiments, variant or mutant NAGLU may have altered function relative to the polypeptide of the unmodified (naturally occurring) or wild-type amino acid sequence. Other structurally modified NAGLUs include members of the family 89 glycoside hydrolases ($\alpha$-N-acetylglucosaminidases), such as NAGLU homologs or orthologs from the same or different species. Known NAGLU homologs or orthologs are summarized in Table 10 and can also be found in CAZy (www.cazy.org/GH89_all.html). Forty-eight NAGLU homologs and orthologs have been reported: 30 bacterial and 18 eukaryotes. Such NAGLU family members and NAGLU orthologs are, for example, bacterial $\alpha$-N-acetylglucosaminidases. In one embodiment, the bacterial $\alpha$-N-acetylglucosaminidase is CpGH89 of *Clostridium perfringens* (SEQ ID NO: 2). In certain embodiments, NAGLU refers to eukaryotic NAGLU, including plant (e.g., *Arabidopsis thaliana*, Nicotiana tabacum, Oryza sativa, Zea mays), insect (e.g., *Drosophila melanogaster*), and mammalian (e.g., *Homo sapiens, Mus musculus, Bos taurus*). In certain embodiments, NAGLU refers to mammalian NAGLU and/or a mammalian NAGLU fragment. In certain embodiments, NAGLU refers to human NAGLU and/or a human NAGLU fragment. In certain embodiments, NAGLU variants include polypeptides that exhibit alterations in posttranscriptional and/or posttranslational processing. In certain embodiments, such posttranscriptional or posttranslational processing includes glycosylation. In certain embodiments, NAGLU variants exhibit an altered glycosylation pattern, for example N-glycosylation (asparagine-linked glycosylation). In specific embodiments, the N-glycosylation is altered by the presence of mannosyl residues (high-mannose type N-glycan). In certain embodiments, N-glycosylation is altered by the presence of mannosyl residues (high-mannose type N-glycan) and by the essential absence of complex glycans, such as glucosylated, sialylated, and/or bisected N-glycans. In some embodiments, a NAGLU variant that exhibits an alteration in glycosylation, such as the presence of high-mannose type N-glycan and by the essential absence of complex N-glycan, is NAGLU-kif (SEQ ID NO: 3).

By "screen" or "screening" is meant to test in silico, in vitro, or in vivo for a compound with a particular characteristic or desired property. These characteristics or desired properties may be chemical, biological, or physical in nature or a combination there of. For example, in screening for NAGLU binding compounds the desired characteristics may include, but are not limited to, high affinity intracellular binding to NAGLU, low affinity intracellular binding to NAGLU, high specificity for binding to one or multiple binding sites on NAGLU, low specificity for binding to one or multiple binding sites on NAGLU, high degree of restoration of NAGLU activity, high bioavailability of the compound, efficient cellular uptake of the compound, high solubility of the compound in pharmacological carriers, low pharmacological toxicity of the compound, etc. Screening may be performed in vitro or in vivo using compound libraries, such as small molecule libraries, DNA libraries, or crystallization buffer matrices. Screening in silico may be performed using predefined or randomized screening parameters and data sets, for example of known test compounds and/or test conditions.

By "select" or "selecting" is meant to provide a pre-existing molecular structure and to chose, for example, from a group of pre-existing compounds, such as small molecules, polypeptides or nucleic acids one or more members that have or exhibit a desired property or characteristic.

Small molecule: The term "small molecule" as used herein is meant to describe a low molecular weight organic compound which is not a polymer. A small molecule may bind with high or low affinity to a biopolymer such as protein, nucleic acid, or polysaccharide and may in addition alter the activity or function of the biopolymer. The molecular weight of the small organic compound may generally be smaller than about 1500 Da. Small molecules may be smaller than about 1000 Da, smaller than about 800 Da, or smaller than about 500 Da. Small molecules may rapidly diffuse across cell membranes and may have oral bioavailability. These compounds can be natural or synthetic.

Space group: The term "space group" refers to the arrangement of symmetry elements in a crystal.

By "substrate" is meant a compound that acted upon by NAGLU, such as. e.g., heparan sulfate, which is degraded by NAGLU via hydrolysis of terminal N-acetyl-D-glucosamine residues in N-acetyl-alpha-D-glucosaminides.

By the term "synthesizing" is meant making a chemical structure from precursors by chemical processes. Synthesizing implies making at least one compound, but is not limited to one compound. In certain aspects, synthesizing implies making more than one compound, such as a series of compounds synthesized in an effort to study structure-activity relationships (SAR) using standard chemistry methods, and/or a series of structurally similar compounds made using standard combinatorial techniques.

Unit cell: The term "unit cell" refers to the basic parallelipiped shaped block. The entire volume of a crystal may be constructed by regular assembly of such blocks.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 2 depicts a sequence alignment of cpGH89 (PDB ID: 2VCC, SEQ ID NO: 2), human NAGLU (SEQ ID NO: 1) and the consensus sequence (SEQ ID NO: 6). The sequence alignment was generated using the web-based Multalin program (multalin.toulouse.inra.fr/multalin/multalin.html). Human NAGLU sequence includes a 23 amino acid signal peptide. cpGH89 has an additional N-terminal carbohydrate binding domain.

FIG. 10 depicts N-glycans (green sticks) and amino acids that are sites of severe mutations of MPS III-B (red sticks).

FIG. 11 depicts amino acids that are sites of active site mutations Y140C, W268R, F410S, and W649C. Also depicted are the product, N-acetylglucosamine (NAG) that was modeled into the active site and catalytic residues E316 and E446.

FIG. 12 depicts amino acids that are sites of mutations relative to asparagines $N_{503}$, $N_{526}$, and $N_{532}$.

FIG. 13 depicts the site of amino acids mutation R234C.

FIG. 14 depicts the site of amino acids mutation Y455C.

FIG. 15 depicts the site of amino acids mutation E153K.

FIG. 16 depicts the clusters of mutations found in NAGLU: glycosylation site, active site, domain interface, N-terminal domain. Red sticks: severe mutations, yellow sticks: attenuated mutations, blue sticks: N.R, ("not reported": Yogalingam et al. (2001) *Hum. Mutat.* 18:264-281), green sticks: N-glycan sites (Asn residues).

FIG. 17 depicts the site of amino acids mutations in the domain interface: H100R, E153K, W156C, E452K, Y455C, and R482W.

SEQUENCE IDENTIFICATION NUMBERS

Figure 1:
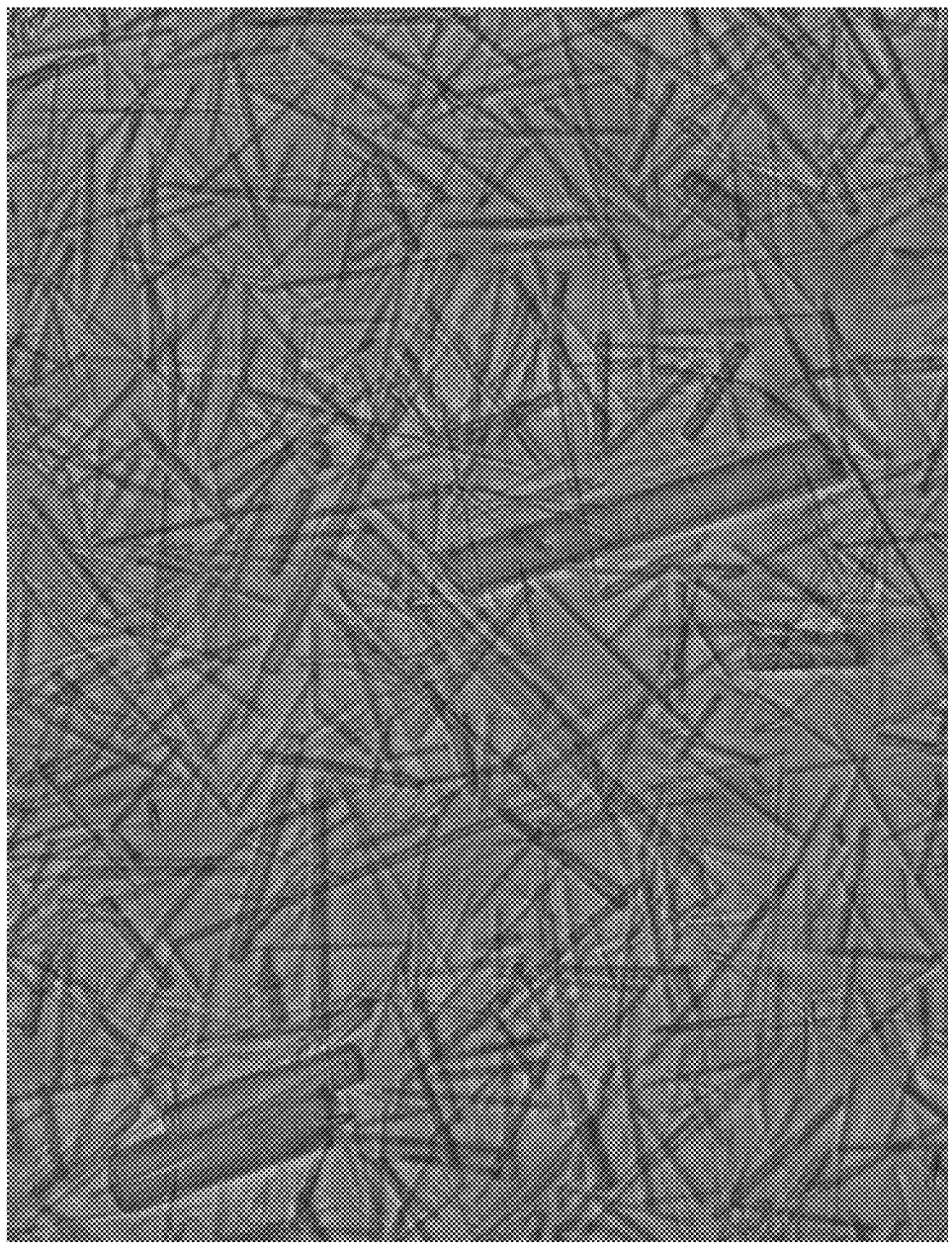
FIG. 1 depicts a photograph of crystals of NAGLU-kif.

SEQ ID NO: 1: Wild-type human NAGLU amino acid sequence.

SEQ ID NO: 2: CpGH89 amino acid sequence of *Clostridium perfringens*.

SEQ ID NO: 3: Human NAGLU amino acid sequence 24-743.

SEQ ID NO. 4: Nucleic acid encoding human NAGLU of SEQ ID NO: 3.

SEQ ID NO. 5: Nucleic acid sequence of NAGLU expression vector pXD671.

SEQ ID NO. 6: Consensus sequence of the CpGH89 amino acid sequence of *Clostridium perfringens* and wild-type human NAGLU amino acid sequence.

DETAILED DESCRIPTION OF CERTAIN EMBODIMENTS OF THE INVENTION

Substantial genetic information describing mutations in the naglu gene that give rise to mucopolysaccharidosis III B (MPS III-B) has been obtained and some biochemical characterization of these mutant NAGLU enzymes have been performed (Schmidtchen et al. (1998) *Am J Hum Genet* 62:64-6; Yogalingam G, et al., (2000) *Biochim Biophys Acta* 1502:415-425). However, progress has been hindered because no structural information for human NAGLU or another mammalian NAGLU is available that can be used to correlate this genetic information to the enzyme's structure and function. CpGH89, an ortholog of human NAGLU from *C. perfringens* (that has about 30% overall amino acid sequence identity to NAGLU) has recently been crystallized and the three dimensional structure of this enzyme was determined (Ficko-Blean et al. (2008) *Proc Natl Acad Sci USA*, 105:6560-5). CpGH89 is a multi-modular protein of 2,095 amino acids. Only residues 26-916 were crystallized. The N-terminal domain (residues 26-155) forms a β-sandwich fold and shares sequence identity to the family 32 carbohydrate-binding modules. The catalytic region is comprised of a small mixed α/β domain (residues 170-280), a decorated (α/β)8 core (residues 280-620), and an all α-helical domain (residues 621-916). Crystallization of human NAGLU or another mammalian NAGLU has previously not been achieved, and no atomic structural information for the human or other mammalian NAGLU has been available before now. This was largely due to the difficulty of generating enough pure homogeneous protein for structural studies. Some aspects of this invention are based on the recognition that the difficulty in obtaining crystals of sufficient quality for X-ray diffraction studies was due to the heterogeneous complex glycosylation of the protein.

The present invention provides an x-ray crystal structure of human NAGLU obtained by crystallizing protein with a substantially homogeneous glycosylation pattern. The present invention also provides purification and crystallization methods for human NAGLU and variants thereof. Homogeneous protein and subsequently crystals of the protein were obtained by inhibiting the processing of glycans by mannosidase-I during expression, leading to altered glycosylation patterns on NAGLU of high mannose neutral glycans. Under certain conditions (e.g., 20 mM Tris, pH 7.5, 100 mM NaCl at approximately 1 mg/mL protein concentration; or 0.01 M nickel chloride, 0.1 M Tris, pH 8.5, 1.0 M lithium sulfate) crystals of NAGLU protein suitable for x-ray diffraction were formed. Crystallization conditions were found that allowed for formation of crystals of sufficient size and quality that enabled gathering x-ray diffraction data for generating atomic coordinates of human NAGLU.

The present invention also provides detailed three-dimensional structural information provided from single crystal X-ray crystallography of human NAGLU with a modified glycosylation pattern. Such structural information will aid the analysis of detailed substrate recognition and catalysis of NAGLU as well as the modeling of the more than 100 identified mutations that have been identified in the naglu gene many of which are implicated in mucopolysaccharidosis III B (MPS III-B). Such structural information is also useful to identify NAGLU polypeptide binding compounds. Suitable binding compounds may be able to bind to the NAGLU polypeptide, to stabilize the NAGLU polypeptide and/or to modulate the enzymatic activity of the NAGLU polypeptide. NAGLU enzyme stabilization in vivo or in vitro may be useful to treat MPS III-B. For example in MPS III-B treatment involving administration of a binding compound to a subject suffering from MPS III-B the administered NAGLU binding compound may enter cells with low or non-existent NAGLU enzymatic activity to stabilize the endogenous NAGLU enzyme in the intracellular environment, thereby increasing or restoring (at least partially) NAGLU enzyme activity. As another example, in MPS III-B treatment involving administration of the purified NAGLU enzyme (enzyme replacement therapy) to a subject suffering from MPS III-B the NAGLU binding compound may be added to the isolated NAGLU in vitro (e.g. in a pharmaceutically acceptable solution) to stabilize the isolated enzyme and to prevent protein aggregation prior to administration. Useful NAGLU binding compounds may, for example, be computationally identified using the atomic coordinates set forth in Table 3 to display the atomic coordinates as a three-dimensional structure of the NAGLU polypeptide. Three-dimensional structures of NAGLU variants, such as NAGLU mutants comprising amino acid substitution, deletion or duplication that are associated with or lead to mucopolysaccharidosis III B (MPS III-B), such as provided in Table 4, may also be modeled using the three-dimensional structure based on the atomic coordinates provided herein as a template. NAGLU binding compounds may be identified that have binding affinity to the active site of NAGLU or to a site outside of the active site of NAGLU (exosites). Exosites that are suitable for NAGLU stabilization may comprise a mutation (e.g. substitution, deletion or duplication) that is associated with or leads to mucopolysaccharidosis III B (MPS III-B). Binding compounds may be designed in silico based on the three dimensional structural information provided by the atomic coordinates described herein. NAGLU binding compounds may also be useful for other applications, such as scientific research, e.g. as stabilizing agents in crystallography.

Cloning of NAGLU

In one aspect, the invention provides methods for cloning a naglu gene and methods for altering the nucleic acid sequence of the wild-type naglu gene. In certain embodiments, naglu genes encoding variant NAGLU polypeptides comprising one or more mutations that are associated with or causative of mucopolysaccharidosis III B (MPS III-B) are provided. In certain embodiments, naglu gene expression vectors for recombinantly producing NAGLU are also provided.

Nucleic acids for the production of recombinant proteins may be i) amplified in vitro by, for example, polymerase chain reaction (PCR); ii) recombinantly produced by cloning; iii) purified (e.g., from a sample or tissue), and isolated, for example by gel separation; or iv) synthesized by, for example, chemical synthesis.

In certain embodiments, nucleic acids comprising a naglu gene or a portion thereof are provided. In certain embodiments, the nucleic acid comprises the sequence as set forth in SEQ ID NO: 1, SEQ ID NO: 3 or a portion thereof. In certain embodiments, a nucleic acid comprising a naglu gene variant is provided. In certain embodiments, the naglu gene variant comprises one or more nucleotide substitutions, additions, deletions, or duplications. In certain embodiments, a nucleic acid is provided that comprises a naglu gene variant associated with or causative of mucopolysaccharidosis III B (MPS III-B).

Modifications and mutations which create a NAGLU polypeptide variant can be made within the nucleic acid sequence which encodes the NAGLU polypeptide. Modifications and mutations include deletions, point mutations, truncations, nucleic acid changes that lead to amino acid substitutions, and nucleic acid changes that lead to the addition of amino acids. NAGLU modifications that are introduced in vitro may resemble modifications that are naturally occurring in and are found in patients with MPS III-B. Other modifications may include for example, addition of a linker molecule, addition of a tag, addition of a detectable moiety, and addition of a fatty acid. Modifications also embrace fusion proteins comprising all or part of the amino acid sequence of NAGLU. The detailed three-dimensional structural information provided herein enable one of skill in the art to predict the effect on protein conformation of a change in protein sequence, and one can thus "design" a variant NAGLU polypeptide according to known methods.

Nucleic acid modifications can be made to generate variants that are silent with respect to the amino acid sequence of the encoded polypeptide, but which provide preferred codons for translation in a particular host. The preferred codons for translation of a nucleic acid in specific non-mammalian expression systems, such as prokaryotic systems, are well known in the art (e.g. Tats et al. (2008) *BMC Genomics*, 9:e463; Buchan et al. (2006) *Nucleic Acids Res*, 34:1015-1027; Moura et al. (2007) *PLoS ONE*, 2(9): e847). Still other modifications can be made to the non-coding sequences of the naglu gene to enhance or control the expression of the gene encoding NAGLU polypeptide.

Conservative amino acid substitutions are amino acid substitution in which the substituted amino acid residue is of similar charge as the replaced residue and/or is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered conservative substitutions even if the residues are in different groups (e.g., replacement of phenylalanine with the smaller isoleucine). Methods for making amino acid substitutions, additions, or deletions are well known in the art, e.g. polymerase chain reaction (PCR)-directed methods (*Molecular Biology: Current Innovations and Future Trends*. by Griffin A. M. and Griffin H. G. (1995) *Horizon Scientific Press*, Norfolk, U.K; Modern Genetic Analysis. by Griffith A. J., Second Edition, (2002) *H. Freeman and Company*, New York, N.Y.).

Non-conservative substitutions, such as mutations found in the naglu gene of patients having MPS III-B, may also be introduced. Using the detailed three-dimensional structural information provided herein the effect of non-conservative substitutions on the structure of NAGLU can be predicted. One skilled in the art will be able to predict the effect of a substitution by using the detailed three-dimensional structural information provided herein, as well as using routine biological screening assays. For a detailed description of protein chemistry and structure, see *Principles of Protein Structure by Schulz*, G. E. et al. (1979) Springer-Verlag, New York, and *Proteins: Structure and Molecular Principles* by Creighton, T. E. (1984) W. H. Freeman & Co., San Francisco.

Another aspect of the invention provides NAGLU that is recombinantly produced. NAGLU may be recombinantly produced using a vector including a coding sequence operably associated with one or more regulatory sequences. A coding sequence and regulatory sequences are "operably associated with" when they are covalently linked to place the expression or transcription of the coding sequence under the control of the regulatory sequence. A promoter region is operably associated with to a coding sequence if the promoter region is capable of modulating transcription of the coding sequence.

The nature of the regulatory sequences needed for gene expression may vary between species or cell types, but may generally include 5' non-transcribed and 5' non-translated sequences involved with initiation of transcription and translation respectively, such as, for example, TATA box, capping sequence, CAAT sequence. 5' non-transcribed regulatory sequences may include a promoter region which includes a promoter sequence for transcriptional control of the operably associated gene. Promoters may be constitutive or inducible. Regulatory sequences may also include enhancer sequences or upstream activator sequences.

A DNA sequence operably associated with a regulatory sequence may be inserted by restriction and ligation into a vector, e.g., for transport between different genetic environments or for expression in a host cell. Vectors are typically composed of DNA or RNA. Vectors include, but are not limited to, plasmids, viral vectors, cosmids, artificial chromosomes, and phagemids. A cloning vector is one which is able to replicate in a host cell, and which is further characterized by one or more endonuclease restriction sites at which the vector may be cut and into which a desired nucleic acid sequence (e.g., an open reading frame) may be inserted. Vectors may contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, alkaline phosphatase or luciferase), and genes which visibly affect the phenotype of transformed or transfected cells, hosts, colonies or plaques.

For prokaryotic systems, plasmid vectors that contain replication sites and control sequences derived from a species compatible with the host may be used. Preferably, the vector has the capacity to autonomously replicate in the host cell. Useful prokaryotic hosts include bacteria such as *E. coli*. To express NAGLU in a prokaryotic cell, it is desirable to operably join the nucleic acid sequence of NAGLU (e.g. cDNA) to a functional prokaryotic promoter. Such promoter may be either constitutive or regulatable (e.g. by induction or de-repression). Because prokaryotic cells may not produce glycosylated NAGLU, expression of NAGLU in eukaryotic hosts may be useful when glycosylation is desired. Eukaryotic hosts include, for example, yeast, fungi, insect cells, and mammalian cells. In addition, plant cells are also available as hosts, and control sequences compatible with plant cells are known in the art.

A wide variety of transcriptional and translational regulatory sequences may be employed, depending upon the nature of the host. The transcriptional and translational regulatory signals may be derived from viral sources, such as adenovirus, bovine papilloma virus and simian virus.

Mammalian promoters, such as, for example, actin, collagen, and myosin may be employed. Transcriptional initiation regulatory signals may be selected which allow for repression or activation, so that expression of the gene sequences can be modulated, for example by regulatory signals, such as repression/initiation through changes in temperature or by addition of a chemical or biological modulating molecule.

Vector can be employed which are capable of integrating a desired gene sequences into the host cell chromosome. Cells which have stably integrated the introduced nucleic acid into their chromosomes can be selected by also introducing one or more markers which allow for selection of host cells which contain the expression vector. The selectable marker gene sequence can either be directly linked to the gene sequences to be expressed, or introduced into the same cell by co-transfection. Additional elements, such as splice signals, transcription promoters, enhancers, and termination signals may also be needed for optimal synthesis of NAGLU mRNA.

Once a desired vector or desired nucleic acid sequence has been prepared, the vector or nucleic acid sequence is introduced into an appropriate host cell by any of a variety of suitable means, for example, transformation, transfection, conjugation, protoplast fusion, electroporation, calcium phosphate-precipitation, or direct microinjection. After the introduction of the vector, recipient cells are grown in a selective medium, which selects for the growth of vector-containing cells. Expression of the cloned gene sequence results in the production of recombinant NAGLU. For example, the naglu open reading frame can be amplified by PCR, with a 5' NheI site and a 3' PacI restriction enzyme site, from a human adrenal gland cDNA library (Clontech #637211). This PCR fragment can be ligated into the shuttle vector, pCRBlunt II TOPO. The nucleic acid sequence of the insert may be verified by sequencing and by restriction digest and DNA gel analysis. The naglu insert is then ligated into the pXD671 vector using NheI/PacI sites. The nucleic acid sequence of the final insert may optionally be verified by sequencing.

Overexpression of NAGLU

In certain embodiments, the invention provides methods for recombinantly producing wild-type NAGLU as well as mutated NAGLU and provides expression systems, such as cell lines for recombinantly producing NAGLU. In certain embodiments, the invention provides methods for altering the glycosylation of NAGLU and methods of expressing NAGLU having an altered glycosylation pattern in expression systems. In certain embodiments, glycan processing inhibitors are provided that can alter the glycosylation on NAGLU.

Recombinant NAGLU can be expressed in various expression host systems. In certain embodiments, the expression host system is a mammalian cell line. Recombinant proteins that are expressed in mammalian cell host systems can be posttranslationally modified. Posttranslational modifications of proteins in mammalian cells include glycosylation, such as N-glycosylation and phosphorylation, such as phosphorylation at Ser, Thr, Tyr or His residues. Other examples of protein expression host systems include other eukaryotic systems, yeast, plant-derived cell lines, insect-derived cell lines, and also prokaryotic systems, such as bacteria (e.g., E. coli). It would be understood by one of ordinary skill that proteins expressed in prokaryotic systems do not comprise N-glycans. In certain embodiments, cell lines are used that secrete the recombinant protein. In certain embodiments, mammalian cell lines are used to produce recombinant NAGLU that secrete the recombinant protein, such as, for example, CHO-K1 cells (Weber et al. (2001) *Prot. Exp. and Purif.* 21:251-259). Non-limiting examples of mammalian cells that may be used in accordance with the present invention include BALB/c mouse myeloma line (NSW, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68, 1982); MRC 5 cells; FS4 cells; and a human hepatoma line (Hep G2).

In certain embodiments, recombinant NAGLU that is expressed in a mammalian cell line that is phosphorylated at one or more phosphorylation sites, e.g. phosphorylation at Ser, Thr, Tyr or His residues. For example, His307 of NAGLU may be modified by phosphorylation.

In certain embodiments, recombinant NAGLU that is expressed in a mammalian cell line has an altered glycosylation pattern. In certain embodiments, recombinant NAGLU that is expressed in a mammalian cell line has altered N-glycosylation. To obtain recombinant NAGLU with altered N-glycosylation the cell line expressing recombinant NAGLU may be treated (contacted) with an agent that modulates or alters glycosylation. In certain embodiments, such agent may be an inhibitor of an enzyme involved in glycan processing pathways. In certain embodiments, such inhibitor may inhibit the activity of one or more glycosyltransferases or glycosidases. Glycosyltransferases and glycosidases involved in mammalian N-glycan processing pathways are, for example, α-1,2-mannosidase (IA, IB, IC), mannosidase II, β-1,2 N-acetylglucosaminyltransferase I (GnTI), β-1,2 GnTII, GnTIII, β-1,4 GnTIV, β-1,4 GnTVI, β-1,4 galactosyltransferase, α-2,3-sialyltransferase, and α-2,6-sialyltransferase. In certain embodiments, N-glycosylation of recombinant NAGLU may be altered by contacting the cells expressing recombinant NAGLU with a glycosidase inhibitor. In certain embodiments, the glycosidase inhibitor is a mannosidase I inhibitor. It should further be appreciated that glycosidase inhibitors other than mannosidase I inhibitors may be used. Glycosidases are involved in the processing of the oligosaccharide chains and quality control mechanisms in the endoplasmic reticulum (ER) of the N-linked glycoproteins. Inhibition of these glycosidases can modulate cellular quality control, polypeptide maturation, transport, and secretion of glycoproteins. Over one hundred glycosidase inhibitors have been isolated from plants and micro-organisms and are known in the art (Asano N. *Glycobiology*, (2003). In certain embodiments, other inhibitors of glycan processing can be used. In certain embodiments, the inhibitor of glycan processing is kifunensine (KIF), deoxymannojirimycin (DMJ) or castanospermine (CST). In one embodiment, the mannosidase I inhibitor is kifunensine. Other examples of inhibitors of lysosomal glycosidases are 2-acetamido-1,2-dideoxynojirimycin, 6-acetamido-6-deoxycastanosperrnine, 1-thio-beta-D-N-acetylglucosamine, colombin, dermatan sulfate, N-acetylglucosamine, p-chloromercuribenzoate, N-acetylglucosaminolactone, and substrate analogs (Winchester and Fleet, *Glycobiology* (1992) 2(3):199-210; Asano, *Cellular and Molecular Life Sciences* (2009) 66(9): 1479-1492; references incorporated herein in their entirety). Substrates of lysosomal glycosidases are, for example, 4-methylumbelliferyl-N-acetyl-α-D-glucosaminide, p-nitrophenyl-N-acetyl-alpha-D-glucosaminide, o-nitrophenyl-N-acetyl-alpha-D-glucosaminide, phenyl-N-acetyl-alpha-D-glucosaminide, UDP-N-acetyl-alpha-D-glucosamine, uridine-5'-diphospho-N-acetyl-alpha-D-glucosaminide, chitobiose, chitotetraose, chitotriose, and compounds with hydrolysable terminal non-reducing N-acetyl-a-D-glucosaminides. In certain embodiments, inhibitors of glycan processing are used to produce glycoproteins that exhibit high-mannose type N-glycans that are not further processed to complex glycans. These altered glycan patterns can, in certain embodiments, affect the physical characteristics of the glycoprotein, such as, for example, its solubility, and/or its biochemical characteristics, such as, for example, its rate of secretion from a cell expressing the glycoprotein. In certain embodiments, recombinant NAGLU is expressed in mammalian cells that are treated (contacted) with an inhibitor of glycan processing. In one embodiment, the inhibitor is a mannosidase I inhibitor. In one embodiment, the mannosidase I inhibitor is kifunensine. In one embodiment the recombinant NAGLU is purified from the cells expressing NAGLU and/or the medium in which the NAGLU-expressing cells are grown, after the cells have been contacted with an inhibitor of glycan processing. In some embodiments, the NAGLU which is expressed by the cells has an altered glycosylation pattern. In one embodiment, the inhibitor of glycan processing is kifunensin and the NAGLU that results has an altered glycan pattern and is referred to herein as "Naglu-kif." In certain embodiments, the NAGLU that has an altered glycan pattern exhibits glycans of the high-mannose type. In certain embodiments, the NAGLU that has an altered glycan pattern exhibits glycans of the high-mannose type and complex glycans are essentially absent. In certain embodiments, the NAGLU that has an altered glycan pattern exclusively exhibits glycans of the high-mannose type.

It should be appreciated that if the recombinant NAGLU is purified, or partially purified, additional alterations to the glycan structures may be made. For example, mannose residues present on NAGLU may be removed (cleaved off) by appropriate enzymes, such as recombinant mannosidases or Endoglycosidase H. Endoglycosidase H (Endo-β-N-acetylglucosaminidase H) is highly specific and cleaves asparagine (N)-linked mannose rich oligosaccharides, but not highly processed complex oligosaccharides from glycoproteins. Endoglycosidase H activity completely removes high-mannose glycan by cleaving the bond between two N-acetylglucosamine (GlcNAc) subunits directly proximal to the asparagine residue, leaving only one GlcNAc residue N-linked to the asparagine. This GlcNAc residue can be the basis for the in vitro synthesis of other glycan structures, using, for example, one or more recombinant glycosyltransferases.

Purification of NAGLU

In another aspect, the invention provides methods for purifying NAGLU. In certain embodiments, methods for purifying recombinantly produced NAGLU as described herein are provided. In certain embodiments, recombinantly produced NAGLU has the amino acid sequence of wild-type NAGLU. In certain embodiments, recombinantly produced NAGLU comprises the amino acid sequence set forth in SEQ ID NO: 1 or SEQ ID NO: 3, or a fragment thereof. In certain embodiments, recombinantly produced NAGLU comprises an amino acid sequence that has at least 60%, 65%, 70%, 75%, 80%, 85%, 90%, 95%, or 99% amino acid sequence homology or identity with the amino acid sequences set forth in SEQ ID NO: 1 and SEQ ID NO: 3, or a fragment thereof. In certain embodiments, the recombinantly produced NAGLU is a NAGLU variant as described herein, such as for example a mucopolysaccharidosis III B (MPS III-B)-associated mutant NAGLU variant comprising one or more of the mutations set forth in Table 4 or the variant is a members of the family 89 glycoside hydrolases (α-N-acetylglucosaminidases) having significant amino acid sequence homology, such as having at least 60%, 65%, 70%, 75%, 80%, 85%, 90%, 95%, or 99% sequence homology with the amino acid sequence set forth in SEQ ID NO: 1 or SEQ ID NO: 3.

In certain embodiments, the invention provides methods for purifying NAGLU having an altered glycosylation pattern. In certain embodiments, purified NAGLU is provided having an altered glycosylation pattern. In certain embodiments, the purified NAGLU provided having an altered glycosylation pattern is NAGLU-kif. In certain embodiments, purified NAGLU is provided that is phosphorylated at one or more phosphorylation sites, e.g. phosphorylation at Ser, Thr, Tyr or His residues. Purified NAGLU may comprise a histindine residue that represents a phosphohistidine. For example, His307 of NAGLU may be modified by phosphorylation.

In certain embodiments, native (non-recombinant) NAGLU purified from a number of mammalian tissues, such as placental tissue (von Figura et al. (1984) *Am. J. Hum. Genet.* 36:93-100; Di Natale et al. (1985) *Enzyme* 33:75-83; Salvatore et al. (1982) *Biol. Cell* 45:212; Salvatore et al. (1984) *Bull. Mol. Biol. Med.* 9:111-121; Sasaki et al. (1991) *J Biochem.* 110:842-46; Weber et al. (1996) *Hum. Mol. Genet.* 5:771-7; Zhao et al. (1996) *Proc Natl Acad Sci USA* 93:6101-5) is provided. NAGLU purified from mammalian tissue may be of a wild-type amino acid sequence or a mutant amino acid sequence. Isolation procedures of NAGLU, for example from tissue, and recombinant expression of NAGLU may provide NAGLU polypeptide of sufficient quantity and quality to permit its identification, characterization, and/or use, for example, for protein crystallization, biochemical studies, therapeutic use, etc. The isolated polypeptide can be selectively produced by expression cloning and purified by techniques known in the art (e.g., chromatography, precipitation, electrophoresis). Such purification methods are well known in the art (*Biochemistry* by Zubay G., 2nd Edition (1988) Macmillan Publishing Co., New York, N.Y., USA; *Protein Purification Handbook* by Amersham Pharmacia Biotech, Edition AB (1999) Amersham Pharmacia Biotech Inc. New Jersey, USA, incorporated herein by reference). In certain embodiments, NAGLU is expressed recombinantly in an animal cell line, an insect cell line or in yeast. In certain embodiments, NAGLU is expressed recombinantly in a mammalian cell line. The mammalian cell line can be a human cell line. In certain embodiments, NAGLU is expressed recombinantly in a mammalian cell line that is treated with an inhibitor of glycosylation. For example, NAGLU can be expressed in HT1080 cells that are treated with kifunensine, a known mannosidase I inhibitor. In certain embodiments, recombinantly expressed NAGLU is secreted into the cell medium.

Described herein are purification methods that provide purified recombinantly produced NAGLU having an altered glycosylation pattern. In certain embodiments, the methods of purification employ chromatography to isolate the desired protein. For example, in certain embodiments, secreted NAGLU from HT1080 cells can be purified from culture media by hydrophobic butyl column followed by anion exchange Q column.

Biochemical Characterization of Recombinant NAGLU

Recombinant NAGLU may be characterized using techniques that are well known in the art. For example, recombinant human NAGLU (rhNAGLU) can be characterized by enzyme kinetic assays, glycodigestion by EndoH and PNGaseF, isoelectric focusing, reverse phase HPLC, and differential scanning calorimetry. Other biochemical assays may also be used. For example, NAGLU activity may be measured using the NAGLU-specific substrate 4-methylumbelliferyl-N-acetyl-α-D-glucosaminide.

Crystallization Screening of NAGLU and Cryo-Optimization

In another aspect the invention provides methods for crystallizing NAGLU. In certain embodiments, methods for crystallizing NAGLU involve crystallizing purified recombinant NAGLU as described herein. In certain embodiments, purified recombinant NAGLU comprising the amino acid sequence set forth in SEQ ID NO: 3 or a fragment thereof is crystallized by the methods provided herein. In certain embodiments, the purified recombinant NAGLU that is crystallized comprises an amino acid sequence that has at least 60%, 65%, 70%, 75%, 80%, 85%, 90%, 95%, or 99% amino acid sequence homology or identity with the amino acid sequences set forth in SEQ ID NO: 1 and SEQ ID NO: 3, or a fragment thereof. In certain embodiments, the purified recombinant NAGLU that is crystallized is a NAGLU variant as described herein, such as for example a mucopolysaccharidosis III B (MPS III-B)-associated mutant NAGLU variant comprising one or more of the mutations set forth in Table 4 or the variant is a members of the family 89 glycoside hydrolases (α-N-acetylglucosaminidases) having significant amino acid sequence homology, such as having at least 60%, 65%, 70%, 75%, 80%, 85%, 90%, 95%, or 99% sequence homology with the amino acid sequence set forth in SEQ ID NO: 1 or SEQ ID NO: 3. In certain embodiments, purified recombinant NAGLU comprising the amino acid sequence set forth in SEQ ID NO: 3 having an altered glycan pattern is crystallized by the methods provided herein. In certain embodiments, the recombinant NAGLU having an altered glycan pattern and crystallized by the methods described herein is NAGLU-kif. For example, NAGLU-kif can be obtained by inhibiting mannosidase I activity in cells that express recombinant NAGLU. Cells expressing recombinant NAGLU may be contacted with the mannosidase I inhibitor kifunensine. Inhibition of mannosidase I activity during NAGLU expression results in NAGLU protein exhibiting high mannose neutral glycans.

One of ordinary skill in the art will appreciate that a wide variety of crystallization conditions may be employed to provide crystals of NAGLU, therefore, a wide variety of crystallization conditions are envisioned and encompassed by the present invention. Every protein crystallizes under a unique set of conditions, such as, for example, supersaturating the solution containing the protein; and/or adding precipitating or crystallizing agents, salts, metals, and/or buffers to the solution containing the protein.

Any crystallization technique known to those skilled in the art may be employed to obtain the crystals of the present invention, including, but not limited to, batch crystallization, vapor diffusion (e.g., either by sitting drop or hanging drop), and micro dialysis. Seeding in some instances may be required to obtain x-ray quality crystals. Standard micro and/or macro seeding of crystals may therefore be used. In certain embodiments, the crystals of the present invention are grown using the hanging-drop vapor-diffusion method.

The crystals of NAGLU may be grown at any temperature suitable for crystallization. For example, the crystals may be grown at temperatures ranging from approximately 0° C. to approximately 30° C. In certain embodiments, the crystals of the present invention are grown at a temperature of between approximately 0° C. to approximately 10° C. In certain embodiments, the crystals of the present invention are grown at a temperature of between approximately 0° C. to approximately 5° C. In certain embodiments, the crystals of the present invention are grown at a temperature of between approximately 5° C. to approximately 10° C. In certain embodiments, the crystals of the present invention are grown at a temperature of between approximately 10° C. to approximately 15° C. In certain embodiments, the crystals of the present invention are grown at a temperature of between approximately 15° C. to approximately 20° C. In certain embodiments, the crystals of the present invention are grown at a temperature of between approximately 20° C. to approximately 25° C. In certain embodiments, the crystals of the present invention are grown at a temperature of between approximately 25° C. to approximately 30° C. In certain embodiments, the crystals of the present invention are grown at a temperature of approximately 0° C. In certain embodiments, the crystals of the present invention are grown at a temperature of approximately 1° C. In certain embodiments, the crystals of the present invention are grown at a temperature of approximately 2° C. In certain embodiments, the crystals of the present invention are grown at a temperature of approximately 3° C. In certain embodiments, the crystals of the present invention are grown at a temperature of approximately 4° C. In certain embodiments, the crystals of the present invention are grown at a temperature of approximately 5° C. In certain embodiments, the crystals of the present invention are grown at a temperature of approximately 6° C. In certain embodiments, the crystals of the present invention are grown at room temperature.

Crystals of the present invention are typically grown from a crystallization solution comprising one or more precipitants. In certain embodiments the precipitants may be selected from polymers, polyethers, alcohols, salts, and/or polyols. In certain embodiments, these precipitants are selected from the group consisting of monomethyl ether (MME); polyethylene glycol PEG-400; PEG-1000; PEG-2000; PEG-3000; PEG-8000; PEG 20,000; (($NH_4$)$_2SO_4$); 2-propanol; 1,4-butanediol; K/Na tartrate; ethanol; NaCl; sodium citrate; $NaH_2PO_4$/$K_2HPO_4$; ethylene glycol; dioxane; 2-methyl-2,4-pentanediol (MPD); polyethyleneimine; tert-butanol; and 1,6-hexanediol.

In certain embodiments, the crystallization conditions may further comprise one or more salts. Thus, in certain embodiments the crystallization conditions further comprises one or more salts selected from the group consisting of $MgCl_2$, $Zn(OAc)_2$, $Li_2SO_4$, $Ca(OAc)_2$, NaCl; ($NH_4$)$_2SO_4$, $CdCl_2$, $CoCl_2$, $MgSO_4$, and $NiCl_2$. In certain embodiments, the crystallization conditions further comprises one or more buffers selected from the group consisting of 2-(cyclohexylamino)ethanesulfonic acid (CHES); 2-(N-morpholino)ethanesulfonic acid (MES); N-cyclohexyl-3-aminopropanesulfonic acid (CAPS); N-cyclohexyl-2-hydroxyl3-aminopropanesulfonic acid (CASPO); 4-(2-hydroxyethyl)

piperazine-1-ethanesulfonic acid (HEPES); 3-(N-morpholino)propanesulfonic acid (MOPS); 2-amino-2-(hydroxymethyl)-1,3-propanediol (Tris); piperazine-N,N'-bis(2-ethanesulfonic acid) (PIPES); N-(2-Acetamido)-2-aminoethanesulfonic acid (ACES); N,N-Bis(2-hydroxyethyl)-2-aminoethanesulfonic acid (BES); N-Tris(hydroxymethyl)methyl-2-aminoethanesulfonic acid (TES); N-(2-acetamido)iminodiacetic acid (ADA); tris(2-carboxylethyl)phosphine (TCEP); acetamidoglycine; cholamine chloride; glycinamide; bicine; N-(2-Hydroxy-1,1-bis(hydroxymethyl)ethyl)glycine (tricine); imidazole; sodium citrate; sodium acetate; cacodylate; Na/K phosphate, and buffers as described in Good et al. (1966) *Biochemistry* 5:467-477, the entirety of which is incorporated herein by reference. For example, precipitants that may be used to crystallize NAGLU include, but are not limited to, lithium sulfate; PEG-400; PEG-550 MME; PEG-2000; PEG-6000; PEG-8000; PEG 20,000; and/or 2-methyl-2,4-pentanediol (MPD) (see Table 1).

In certain embodiments, the pH of the crystallization solution is between about a pH of approximately 4 to pH of approximately 9. In certain embodiments, the pH of the crystallization solution is between about a pH of approximately 6.5 to a pH of approximately 9. In certain embodiments, the pH of the crystallization solution is approximately 7.5. In certain embodiments, the pH of the crystallization solution is near the isoelectric point of the protein.

In a specific embodiment, Naglu-kif at a concentration of about 1 mg/ml is screened for crystallization conditions using the sitting drop vapor diffusion method employing a random matrix crystallization screening kit. Such kits are commercially available, for example, Qiagen NeXtal Classic Suite crystal screen kit, Qiagen catalog#130701. In a specific embodiment, Naglu-kif is crystallized under conditions such as summarized in Table 1. In a further specific embodiment, Naglu-kif is crystallized in condition #58 (0.01 M nickel chloride, 0.1 M Tris, pH 8.5, 1.0 M lithium sulfate) as summarized in Table 1.

In certain embodiments, NAGLU-kif crystals which have a high solvent content may be dehydrated by equilibrating against a buffer containing polyethylene glycol (PEG) in a sitting drop vapor diffusion tray.

In certain embodiments, the crystals are screened for optimal cryo-conditions to freeze the crystals at the temperature of liquid nitrogen, for example, to attenuate the radiation damage to crystals that occurs during data collection. In certain embodiments, screening for optimal cryo-conditions can be carried out in crystallization buffers containing 20-35% v/v of polyols, such as glycerol, ethylene glycol or 2-methyl-2,4-pentanediol (MPD), or 35-70% w/v of sugars, such as sucrose or xylitol. Crystals may be soaked in the cryo-buffer for about 5-15 minutes. In a specific embodiment, cryo-protection of NAGLU crystal grown in condition#58 (0.01 M nickel chloride, 0.1 M Tris, pH 8.5, 1.0 M lithium sulfate, Table 1) is achieved by soaking the crystals in a cryo-buffer containing 25% glycerol. Crystals protected with 25% glycerol containing cryo-buffer diffracted to 3.2 Å. In other embodiment cryo-protection of NAGLU crystals grown in Q buffer is achieved by soaking the crystals in a cryo-buffer containing glycerol and xylitol (20 mM Tris pH7.5, 100 mM NaCl, 15% glycerol and 20% xylitol). Crystals protected with glycerol/xylitol containing cryo-buffer diffracted to 2.9 Å or 2.4 Å. In 2.4 Å structure, the active site pocket may be occupied by one molecule of xylitol and two molecules of glycerol.

NAGLU crystals may also include a binding compound bound to the NAGLU polypeptide. The complex of the polypeptide and binding compound may be formed before, after, or during crystallization. In certain embodiments, the crystals of the present invention and the crystallization conditions further comprise a binding compound. Thus, in certain embodiments, the crystallization solution of the above method further comprises a binding compound in order to provide a NAGLU-binding compound complex. In certain embodiments, the NAGLU crystal provided by the above method is soaked in a solution of a binding compound to provide a NAGLU-binding compound complex. In certain embodiments, the binding compound is bound in the active site of NAGLU. In certain embodiments, the binding compound is a glycosidase inhibitor, such as an inhibitor of a lysosomal glycosidase. Examples of N-acetylglucosaminidase inhibitors include, but are not limited to, 2-acetamido-1,2-dideoxynojirimycin (2AcDNJ) (Horsch et al. (1991) *Euro J Biochem* 197:815-818), O-(2-acetamido-2-deoxy-D-glucopyranosylidene)amino-N-phenylcarbamate (PUG-NAc) (Beer et al. (1990) *Helv Chim Acta* 73:1918-1922), and 6-acetamido-6-deoxycastanospermine (6AcCAS) (Liu et al. (1991) *Tetrahedron Lett* 32:719-720; Zhao and Neufeld (2000) *Protein Expr. Purif.* 19:202-211), 1-thio-beta-D-N-acetylglucosamine, Colombin, dermatan sulfate, N-acetylglucosamine, p-chloromercuribenzoate, and N-acetylglucosaminolactone. In some embodiments, the inhibitor is a reversible inhibitor. In other embodiments, the binding compound is bound outside the active site at one or more exosites. In some embodiments, the binding compound, whether bound in the active site or at one or more exosites, aids in stabilizing the protein for crystallization and/or x-ray diffraction.

Crystals of NAGLU

In another aspect, the present invention provides crystals of NAGLU. In certain embodiments, the crystals are of NAGLU, or any structural modifications thereof. In certain embodiments, the crystals are of native NAGLU. In certain embodiments, the crystals are of NAGLU comprising the amino acid sequence set forth in SEQ ID NO: 3. In certain embodiments, the crystals are of NAGLU having an altered glycosylation pattern. In certain embodiments, the crystals are of NAGLU comprising the amino acid sequence set forth in SEQ ID NO: 3 having an altered glycosylation pattern. In certain embodiments, the crystals are of NAGLU-kif.

A crystal of the present invention may take a variety of forms, all of which are contemplated by the present invention. In certain embodiments, the crystal may have a size of about 100×20×20 micron, about 150×50×50 micron, about 200×50×50 micron, or about 300×50×50 micron. In certain embodiments, the crystals have the optical appearance as illustrated in FIG. 1 and/or the crystals may grow as hexagonal rods. Crystals may have a high solvent content. In certain embodiments, dehydration of the crystals may be used to improve the diffraction resolution of the crystal.

Crystal Structure of NAGLU

In another aspect, the present invention provides three-dimensional structural information for human NAGLU or for variants, such as variants that comprise one or more amino acid substitutions, deletions or duplications, for example those found in mutant NAGLU polypeptides associated with MPS III-B. Other variants include homologs or orthologs of the members of the family 89 glycoside hydrolases (α-N-acetylglucosaminidases). In some embodiments, the invention provides methods for constructing models of these variants using the three-dimensional structural information for human NAGLU as a template. The method may include adjusting the backbone dihedral angles and the side chains of each amino acid that is modeled until a low energy conformation is obtained.

In certain embodiments, X-ray diffraction data collection can be performed in an X-ray crystallography facility. One, two, three, or more diffraction data sets may be collected from one or more NAGLU crystals. In certain embodiments, the crystals of the present invention diffract to a resolution limit of at least approximately 8 angstrom (Å). In certain embodiments, the crystals diffract to a resolution limit of at least approximately 6 Å. In certain embodiments, the crystals diffract to a resolution limit of at least approximately 4 Å. In certain embodiments, the crystals diffract to a resolution limit of at least approximately 2.5 Å. In certain embodiments, the crystal diffracts x-rays for a determination of structural coordinates to a maximum resolution of about 3.9 Å, of about 3.2 Å, or of about 2.9 Å. The crystals may diffract to a maximum resolution of about 2.5 Å to about 3.5 Å, of about 2.0 Å to about 3.0 Å, of about 2.5 Å to about 3.0 Å, or of about 3.0 Å to about 3.5 Å.

Diffraction data can be collected using a variable oscillation angles, number of frames and exposure times that all depend on the equipment used and on the quality of the crystal(s) used to collect the data. One of ordinary skill would know how to optimize these parameters (*Principles of protein X-ray crystallography* by J. Drenth. 2nd ed. (1999) Springer-Verlag, Heidelberg, Germany; *Structure Determination by X-ray Crystallography* by M. Ladd and R. Palmer. 4th ed. (2003) Kluwer Academic/Plenum Publishers, New York, N.Y.). In certain embodiments, diffraction data can be collected with 1° oscillation. Other oscillation may be used, e.g. oscillations of less than or greater than 1°. For example, diffraction data can be collected with 0.1°, 0.3°, 0.5°, 1°, 1.5°, 2°, 3°, 4°, 5° or 10° oscillation, or any oscillation angle in between these angles. In certain embodiments, 120 frames are collected. More or fewer than 120 frames may be collected. For example, 10, 20, 50, 100, 200, 300, 400, 500, 1000, or 5000 frames may be collected, or any number of frames in between these numbers. In certain embodiments, the exposure is 5 minutes per frame. Other frame exposure times may also be used, such as, for example 5 seconds, 10 seconds, 20 seconds, 30 seconds, 40 seconds, 50 seconds, 60 seconds, 120 seconds, 180 seconds, 3 minutes, 4 minutes, 10 minutes, 20 minutes, 30 minutes per frame or any exposure time in between these times. Data merging and scaling can be done, for example, using HKL2000 software suite (HKL Research, Inc., Charlottesville, Va.). Structure determination, model building, and refinement can be performed, for example, using software such as Molrep, coot and Refmac that are part of CCP4 software suite. MolRep is a program for automated molecular replacement (e.g., MolRep, version 10.2.35). *Coot Graphical Interface* by Paul Emsley (wwv-v.ysbl.york.ac.uk/~emsley) for model building includes an interface to refmac5 (Gnu Public License; refinac5, e.g. version 5.5.0072 or version 5.5.0109). A macromolecular refinement program by Garib Murshudov et al. is integrated into the CCP4 program suite (www.ccp4.ac.uk, CCP4, version 6.1.3). Structural analyses may be performed using molecular viewer software PYMOL (pymol.org). In certain embodiments, models of NAGLU may be obtained by molecular replacement method using the program Molrep and the structural information available for CpGH89 as search model. For example, initial phases may be obtained removing from the coordinates of CpGH89 all of the side chains resulting in a poly-alanine model. Such models may be used for further model building and refinement, for example using programs such as coot and Refmac.

The term "molecular replacement" refers to a method that involves generating a preliminary model of the three-dimensional structure of NAGLU or a NAGLU complexed with a binding compound whose structure coordinates are not known by orienting and positioning a NAGLU structure whose atomic coordinates are known (Table 3). Phases are calculated from this model and combined with the observed amplitudes of the unknown crystal structure to give an approximate structure. This structure is then subject to any of several forms of refinement to provide a final, accurate structure. Any program known to the skilled artisan may be employed to determine the structure by molecular replacement. Suitable molecular replacement programs include, but are not limited to, *AMORE* (1994) (*the CCP4 suite: Acta Crystallogr. D.*, 50:760-763; Navaza (1994) *Acta Cryst.*, A50:157-163) and CNS (1998) (*Acta Crystallogr. D.*, 54:905-921).

In certain embodiments, the atomic coordinates of crystalline NAGLU are provided. In one embodiment, wherein the crystal diffracts at a resolution of 2.9 Å the model may be refined to a final R factor of 18.7% and $R_{free}$ of 22.9%. In one embodiment, wherein the crystal diffracts at a resolution of 2.4 Å the model may be refined to a final R factor of 17.46% and $R_{free}$ of 19.81%. In certain embodiments, atomic coordinates of crystalline NAGLU-kif are provided and the parameters are set forth Table 3 and Table 2. In one embodiment, crystalline NAGLU at 2.9 Å has a space group of $P6_3$ and has unit cell parameters of a=b=205.66 Å, c=78.69 Å or a=b=207.5 Å, c=79.6 Å, and bond angles of α=β=90°, γ=120°. In another embodiment, crystalline NAGLU at 2.4 Å has a space group of $P6_3$ and has the unit cell parameters of a=b=205.13 Å, c=78.44 Å, α=β=90° and γ=120°.

Figure 3:
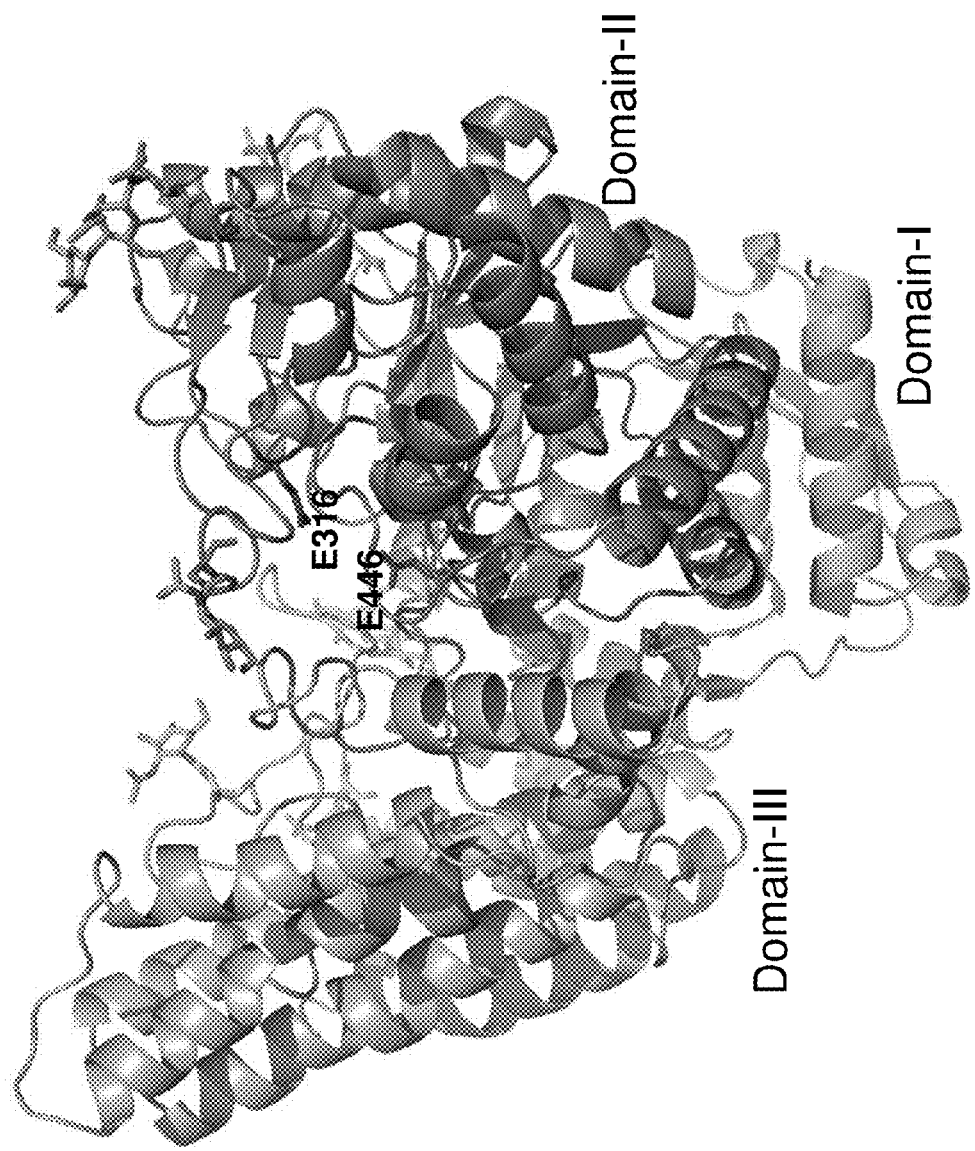
FIG. 3 depicts a stick-and-ribbon representation of the crystal structure of NAGLU. Three domains are colored in cyan (Domain I), blue (Domain II), and dark salmon (Domain III). Glycans are shown as green sticks. Catalytic residues E316 and E446 are shown as red sticks.
Figure 4:
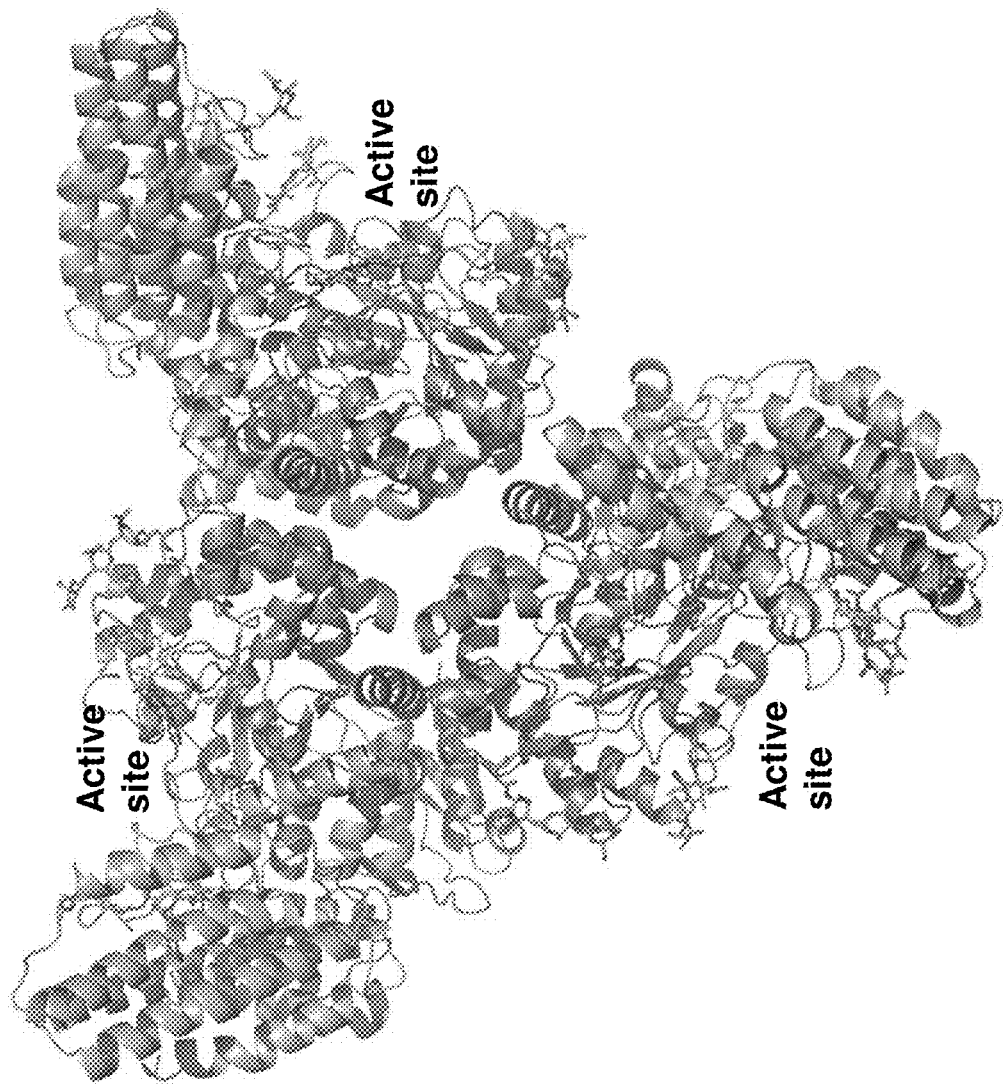
FIG. 4 depicts a stick-and-ribbon representation of the trimeric structure of NAGLU. Three domains are colored in cyan (Domain I), blue (Domain II), and dark salmon (Domain III). Glycans are shown as green sticks. Catalytic residues E316 and E446 are shown as red sticks. Active sites of the three molecules are marked.

Crystalline NAGLU has three domains (I, II, III). Domain I is a small α/β domain (amino acids 24-126). Domain-II is a $(α/β)_8$ barrel domain (amino acids 127-467) containing the catalytic residues. In certain embodiments, NAGLU exhibits a crystallographic symmetry of a trimeric arrangement formed by the interaction of domains II, as illustrated in FIG. 4. Domain III is an all α-helical bundle domain (amino acids 468-743). The three domain structure is illustrated in FIG. 3; amino acid residue are numbered according to SEQ ID NO:3, amino acids 24-743).

The entrance to the NAGLU active site is at the cleft between domains II and III. Some of the residues found to be at the entrance are $H_{270}$, $Q_{355}$, $H_{356}$, $Q_{359}$, R510, and R519. The catalytic site comprises catalytic residues $E_{316}$ and $E_{446}$ of SEQ ID NO: 3 spaced about 6 Å apart. In certain embodiments, the active site is further defined by one or more of the following residues: $N_{134}$, $C_{136}$, $Y_{140}$, $W_{201}$, $M_{204}$, $W_{268}$, $N_{315}$, $W_{352}$, $L_{383}$, $L_{407}$, $F_{410}$, $H_{512}$, $W_{649}$, $I_{655}$, and $Y_{658}$. These residues are located within 5 Å of the product molecule (N-acetylglucosamine) as it was modeled in the active site. $H_{512}$ may occur in multiple conformations. The three-dimensional structure of the active site of human NAGLU is provided by the atomic coordinates listed in Table 3 and atomic coordinates for the active site are provided in Table 5. Some of the active site residues that are also sites of mutations that are associated with Sanfilippo syndrome type B (mucopolysaccharidosis III B (MPS III-B)) are illustrated in FIG. 11.

In one embodiment, the model created based on the structural information obtained contains positional information for amino acid 24-743 of NAGLU. Amino acids 1-23 are part of a signal peptide. In certain embodiments, the purified recombinant NAGLU protein has this signal peptide cleaved ($NAGLU_{24-743}$). In certain embodiments, models may be used to display the position of one or more N-linked glycans. In certain embodiments, positional information of up to six glycans within the NAGLU structure are provided. In a certain embodiment, the positions of the six glycans are N261, N272, N435, N503, N526 and N532. NAGLU-kif glycosylation may be analyzed. For example, analysis of glycosylation pattern by High Performance Anion Exchange with Pulsed Amperometric Detection (HPAE-PAD) may indicate that NAGLU-kif has high mannose neutral glycans and lacks sialylated or phosphorylated glycans. In 2.9 Å structure, the electron density obtained for the glycans attached to asparagine residues suggests at least one N-acetylglucosamine molecule each on N272, N526, and N532, two N-acetylglucosamine molecules each on N435 and N503, and two N-acetylglucosamine molecules and one mannose residue on N261.

It should be understood that while Table 3 provides atomic coordinates for crystalline NAGLU, the present invention also contemplates structural modifications thereof, for example, mucopolysaccharidosis III B (MPS III-B)-associated mutant NAGLU enzymes as described herein, as well as other members of the family 89 glycoside hydrolases (α-N-acetylglucosaminidases), as having significant structural homology (e.g., significant structural overlap), particularly in the areas recognized as active, and thus providing the same or similar structural information as provided herewith. Significant structural homology refers to at least one of the following criteria: (i) at least 60%, 65%, 70%, 75%, 80%, 85%, 90%, 95%, or 99% structural homology with crystalline NAGLU; or (ii) at least 60%, 65%, 70%, 75%, 80%, 85%, 90%, 95%, or 99% structural homology with a recognized active binding site of crystalline NAGLU. In certain embodiments, significant structural homology may also refer to at least 60%, 65%, 70%, 75%, 80%, 85%, 90%, 95%, or 99% structural homology with the primary amino acid sequence of NAGLU. Furthermore, the primary amino acid sequence of NAGLU may be a sequence included as a segment in a larger amino acid sequence, or may be a fragment thereof. In some embodiments, a fragment of a full-length, wild-type NAGLU protein is provided or used in an inventive method or system provided herein. In some embodiments, a NAGLU fragment comprises a NAGLU sequence of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50-75, 75-100, 100-150, 150-200, 200-250, 250-500, or more than 500 amino acids. In some embodiments, a fragment of NAGLU does not comprise a full-length NAGLU sequence, for example, a full-length human NAGLU sequence. In some embodiments, a fragment of NAGLU comprises all or at least part of the protein responsible for the enzymatic activity of full-length NAGLU. In some embodiments, fragments include fragments that contain all or part of domains II and/or III, which contain the active site; fragments containing the catalytic residues ($E_{316}$, $E_{446}$) that are located in domain II; fragments containing residues from domain III that form the active site; and fragments containing domain I, which stabilizes domains II and III. The present invention contemplates any and all such variations and modifications of NAGLU.

Uses of NAGLU Structural Information

In another aspect the invention provides methods and/or uses of NAGLU structural information, for example methods for the design of functional fragments of NAGLU for use in gene replacement or enzyme replacement therapy, and methods for designing, identifying, and/or screening binding compounds to NAGLU that may be useful in treating mucopolysaccharidosis III B (MPS III-B). In certain embodiments, methods for designing functional fragments of fusion proteins of NAGLU are provided using the three dimensional structure information provided herein. In certain embodiments, functional NAGLU fragments or fusion proteins are provided that may be altered to affect in vivo delivery or to provide functionality that restores some or all of NAGLU activity in cells that have low NAGLU activity or completely lack NAGLU activity. In certain embodiments, NAGLU fusion proteins are provided that have been altered to cross the blood-brain barrier to increase in vivo delivery to the brain. In certain embodiments, methods are provided for the production of NAGLU polypeptides having an altered glycosylation pattern. In certain embodiments, methods are provided for designing NAGLU polypeptides having one or more altered glycosylation sites, such as asparagines, using the three-dimensional structural information provided herein. In certain embodiments, methods for providing in silico models of mutated NAGLU are provided. In certain embodiments, such methods comprise modeling one or more of the mutations associated with mucopolysaccharidosis III B (MPS III-B) into a model based on the three-dimensional structural information of NAGLU provided herein. In certain embodiments, methods for designing, identifying, and/or screening binding compounds to NAGLU (e.g. wild-type and/or mutated NAGLU) are provided. These binding compounds may be useful in the treatment of mucopolysaccharidosis III B (MPS III-B). Since Sanfilippo syndrome type B (mucopolysaccharidosis III B (MPS III-B)) is thought to be caused by reduced or diminished NAGLU enzymatic activity NAGLU binding compounds that might be particularly useful in the treatment of MPS III-B are compounds that increase (or restore at least some) NAGLU enzymatic activity. In certain embodiments, the binding compound may provide NAGLU enzyme stabilization, e.g. during protein folding. The compound may also affect aspects of intracellular trafficking of NAGLU or aspects of enzymatic function, such as substrate recognition and/or NAGLU catalytic activity. In certain embodiments, methods are provided for the in silico design, identification, and/or screening of NAGLU binding compounds using the three-dimensional structural information provided herein. In certain embodiments, methods are provided that can be used to identify inhibitors, reversible inhibitors, activators and/or stabilizers of NAGLU activity. In certain embodiments, methods are provided that can be used to identify binding compounds that modulate NAGLU stability. In certain embodiments, methods are provided that can be used to identify binding compounds that modulate NAGLU stability, NAGLU activity, and or NAGLU intracellular trafficking. In certain embodiments, methods are provided that can be used to test potential binding compounds for their ability to bind to, to modulate NAGLU stability, to modulate NAGLU activity, and or to modulate NAGLU intracellular trafficking. In certain embodiments, these methods include in silico, in vitro, and in vivo methods. In certain embodiments, methods are provided, solving the structure of NAGLU homologs or orthologs using the three dimensional structural information provided herein. In certain embodiments, methods are provided, solving the (partial) structure of proteins comprising structurally or functionally homologous domains using the three-dimensional structural information for NAGLU provided herein.

Naglu Gene Replacement Therapy and NAGLU Enzyme Replacement Therapy

Although several therapeutic approaches have been applied to the murine model of the disease, no effective therapy is available for human patients. NAGLU is of interest as a potential candidate for gene replacement therapy. For Sanfilippo syndrome type B, a knock-out mouse model has been generated (Li et al. (1999) *Proc Natl Acad Sci USA*, 96:14505-10) and a dog model has also been established (Ellinwood et al. (2003) *J Inherit. Metab. Dis.* 26:489-504). Mouse model studies in the Sanfilippo syndrome type B knock-out mouse model showed that autologous stem cell transplant after ex-vivo gene transfer with retroviral vectors (Zheng et al. (2004) *Mol. Genet. Metab* 82:286-95 and lentiviral vectors (Di Natale et al. (2005) *Biochem. J.* 388:639-46) provides therapeutic effects. Further, recombinant adeno-associated vectors (AAV) have been directly administered into the brain of the model mice alleviating intracerebral lesions (Cressant et al. (2004) *J. Neurosci* 24:10229-39 and Fu et al. (2002) *Mol. Ther.* 5:42-49).

The three-dimensional structural information provided herein will aid in the identification of sites in the NAGLU enzyme that may be altered, deleted, or fused to another polypeptide that confers additional functionality. For example, biologically active NAGLU fragments can be designed using the three-dimensional structural information provided herein. Useful NAGLU fragments include, but are not limited to, fragments containing all or part of domains II and/or III, which contain the active site; fragments containing the catalytic residues ($E_{316}$, $E_{446}$) that are located in domain II; fragments containing residues from domain III that form the active site; fragments containing domain I, which stabilizes domains II and III; or fragments containing parts of all three domains I, II, and III. In another example, the NAGLU enzyme that may be altered so that more effective delivery vectors and/or delivery systems can be generated. The three-dimensional structural information provided herein will be useful to aid the design of NAGLU variants at the level of the nucleic acid sequence. Functional fragments of naglu cDNA (as determined based on the three-dimensional structural information provided herein) may be cloned into retroviral vectors, lentiviral vectors, or recombinant adeno-associated vectors that have been used for autologous stem cell transplant after ex vivo gene transfer or direct in vivo gene delivery. Functional fragments may have the ability to restore some or all of the activity of NAGLU in cells that harbor a mutated form of NAGLU. Functional fragments may be smaller than full-length protein and thus may be easier to deliver in vivo. Functional fragments may also be fused to other functional fragments not derived from naglu cDNA that may exhibit additional functionality, for example, aiding in vivo delivery, supplying additional enzymatic functions or comprising signaling sequences that govern intracellular protein maturation and protein sorting. In certain embodiments, various fusion tags fused to the C-terminus may be useful for, e.g., lysosomal delivery. In other embodiments, the N-terminus of NAGLU is in close proximity to the trimer interface, and N-terminal fusions may or may not be used for, e.g., lysosomal delivery. N- or C-terminal fusions may be designed based on the three-dimensional structure provided herein.

Native NAGLU has been purified to homogeneity from several tissues and has also been produced recombinantly (Weber et al., (2001) *Prot. Exp. and Purif.* 21:251-259). NAGLU fusion proteins (fusions between NAGLU and the ligand domains of the LDL receptor ligands ApoB and ApoE) have been proposed (Dr. Ellinwood, Iowa SU, Ames, Iowa). Such fusions are thought to be able to cross the blood brain barrier and may be useful for either gene therapy or intravenous enzyme replacement therapy. The three-dimensional structural information provided herein will be useful to aid the design of NAGLU variants that may only comprise portions of the enzyme, e.g., the active site. Such recombinant variants, which may be smaller that the wild-type protein may then be fused for example to peptide sequences (e.g. tissue specific) or peptide sequences that aid cellular uptake. These peptide sequences may be derived from mammalian polypeptides or can be of non-mammalian origin, such as viral peptide sequenced. For example, fusion partners such as ApoE, TAT, and IGFII fused at C-terminus of NAGLU may be used. It should be appreciated that the full-length NAGLU may also be altered (fused) in such ways. Fusions of the full-length or variant NAGLU polypeptide may also include the fusion to non-peptide sequences, such as, for example, small molecules (e.g., fatty acids) PEG and glycans or other moieties that aid in vivo delivery and/or stability.

The three-dimensional structural information provided herein will aid in the identification, characterization and/or design of specific NAGLU binding compounds, as described herein. These compounds may have the ability to stabilize NAGLU polypeptides. NAGLU binding compounds as described herein may be used to stabilize isolated or recombinantly produced wild-type NAGLU, which may be relatively unstable, both during purification/manufacture and in storage to improve its use in enzyme replacement therapy. It is known in the art that injected human proteins can cause an immune responses induced by misfolded proteins in the preparation (Maas et al. (2007) *J. Biol. Chem.* 282:2229-2236). NAGLU binding compounds as identified using the atomic coordinates provided herein may be included in the manufacture and storage of NAGLU to reduce unwanted NAGLU protein precipitation or to preserve a high degree of enzymatic activity by maintaining the protein properly folded during purification, synthesis and/of storage. NAGLU may be contacted with the NAGLU binding compound prior to enzyme replacement therapy (i.e., prior to administering the NAGLU enzyme to the subject). NAGLU binding compounds may also be combined with the isolated (purified) NAGLU enzyme during treatment, which may improve in vivo stability (bioavailability) of the administered enzyme, and may reduce the need for frequent dosing.

Alteration of NAGLU Glycosylation and Intracellular Trafficking

It is well known in the art that glycosylation of glycoproteins can be of functional importance and can influence subcellular localization (Marcus et al. (2000), *J. Biol. Chem.*, 275:1987-92). The addition and trimming of oligosaccharide side chains during post-translational modification play an important role in determining the fate of secretory, membrane, and lysosomal glycoproteins. It has been suggested that trimming of oligosaccharide side chains also plays a role in the degradation of misfolded glycoproteins as a part of the quality control mechanism of the endoplasmic reticulum (ER). Asparagine-linked (N-linked) oligosaccharide side chains play an important role in intracellular transport of glycoproteins, for example, mannose-6-phosphate modification is a key determinant of sorting to the lysosome (Kornfeld et al. (1989) *Annu. Rev. Cell Biol.* 5:483-525). Transport of many secretory and membrane glycoproteins from the ER to the appropriate destination depends on the interaction of the innermost glucose residue of the oligosaccharide side chains with resident ER molecular chaperones, such as calnexin and calreticulin (Helenius et al. (1997) *Trends Cell Biol.* 7:193-200, Zapun et al. (1997) *Cell* 88:29-38). It has been suggested that trimming of the N-glycan by glucosidases I and II and interaction with calnexin and calreticulin facilitate the proper folding and translocation of wild type glycoproteins. Trimming of glucose residues by glucosidases and of mannose residues by ER mannosidases is thought to be involved in the degradation of misfolded, unassembled, or mutant glycoproteins (Liu et al. (1997) *J. Biol. Chem.* 272:7946-7951; Liu et al. (1999) *J. Biol. Chem.* 274:5861-5867; Jakob et al. (1998) *J. Cell Biol.* 142:1223-1233; Kearse et al. (1994) *EMBO J.* 13:3678-3686; Moore et al. (1993) *J. Biol. Chem.* 268:3809-3813; Yang et al. (1998) *J. Exp. Med.* 187:835-846; Vierhoeven et al. (1999) *Biochem. J.* 337:133-140). NAGLU has six sites of N-glycosylation (N261, N272, N435, N503, N526, and N532) and with the aid of the three-dimensional structural information provided herein the asparagine residues may be altered, replaced, or deleted according to the three-dimensional structural information provided herein to modulate NAGLU enzymatic function and/or to alter subcellular localization.

NAGLU Folding, Stability and Therapies Involving Chemical Chaperones

The lumen of the ER provides a highly specialized compartment for the folding and oligomeric assembly of secretory proteins, plasma membrane proteins, and proteins destined for the various organelles of the vacuolar system. Their conformational maturation is a complex process determined by the primary amino acid sequence, by post- and co-translational modifications, by the intralumenal milieu, and by a variety of chaperones and folding enzymes (Gething and Sambrook (1992) *Nature;* 355:33-45; Helenius et al. (1992) *Trends Cell Biol;* 8:227-31). The ER possesses efficient quality control mechanisms to ensure that transport is limited to properly folded and assembled proteins (Hurtley and Helenius (1989) *Annu Rev Cell Biol.* 5:277-307). It has been shown that some human genetic diseases are due to mutations in proteins that influence their folding and lead to retaining of mutant proteins in the ER and successive degradation (Bychkova and Ptitsyn (1995) *FEBS Lett.* 359: 6-8; Welch and Brown (1996) *Cell Stress Chaperones* 1:109-15). Genetically inherited diseases are often characterized by specific point mutations or deletions which give rise to proteins that fail to fold properly. In some cases, the mutations result in the protein exhibiting only a partial loss of its normal activity. The mucopolysaccharidosis III B (MPS III-B) phenotype is associated with a large number of missense, nonsense, and deletion mutations, with the missense mutations being the most frequent. These mutations are thought to influence the protein by reducing its stability and resulting in less functional enzyme reaching the lysosome.

Since instability of mutated NAGLU may result in the MPS III-B phenotype, one approach to treating diseases that stem from decreased protein stability involves the use of small molecules (Amaral (2006) *J Inherited Metabol Dis* 29:477-487). Compounds called "chemical chaperones" have been described that bind to the newly synthesized polypeptide and increase its stability.

Chemical chaperones as described herein are particularly useful for stabilizing NAGLU polypeptides that comprise one or more mutations that make the polypeptide less stable than the native (wild-type form). Such NAGLU mutants may be degraded more rapidly, thereby lowering their steady-state levels below what is required to maintain the enzymatic function and thus the health of the cell. Such NAGLU mutants may also aggregate when they unfold and such aggregates may themselves be toxic to the cell. There are many severe human diseases that arise from either mutations that destabilize an essential protein or the age-dependent build-up of toxic misfolded forms of normal proteins (Loo et al. (2007) *Expert Rev Mol Med* 9:1-18). Chemical chaperones may be used to stabilize the native fold of the protein, preventing aggregation and restoring (or at least partially restoring) proper steady-state levels. There is a particular need for chaperone activity in compartments where proteins are subjected to unusual environmental stress, such as the mitochondrion, where large amounts of reactive oxygen species are present, the lysozome, which has a low pH and a high content of degradative enzymes, and the endoplasmic reticulum (ER), where many unstable mutant proteins may misfold during synthesis. It is well known in the art that the binding of an inhibitor to an enzyme stabilizes the enzyme against thermal denaturation, in some cases by 10° C. or more (Sanchez-Ruiz J M (2007) *Biophys Chem* 126:43-49). Inhibitor binding is also often used in crystallography since liganded proteins tend to crystallize more readily than their unliganded counterparts because their structures are more stable. In certain embodiments, the chemical chaperone is an enzyme inhibitor or active-site-directed ligand. A preferred inhibitor or active-site-directed ligand is a reversible inhibitor. A reversible inhibitor may allow the presence of an equilibrium amount of free enzyme (Fan J Q (2008) *Biol Chem* 389:1-11), which is available for substrate binding, which in turn may also stabilize the protein, to inhibitor bound enzyme. It should be appreciated that the affinity of the inhibitor to the binding site is important, since high affinity binding may lead the inhibitor to be effectively irreversible, while low binding affinity may make the chaperone activity ineffective. In certain embodiments, inhibitors with a $K_i$ (equilibrium disassociation constant) close to the $K_m$ (Michaelis-Menten constant) of the substrate or exhibiting a $K_i$ that is higher may be particularly useful. It should be appreciated that a dose of a chemical chaperone that inhibits the target polypeptide that is high enough to significantly reduce the enzymatic activity should be avoided. Dosing regimens may be used that employ administering the dose in particular time intervals interrupted by periods of non-administration rather than dosing continuously. Controlled release may also be needed in some cases. In some cases mutated proteins may be so unstable that they cannot be effectively chaperoned by inhibitors because the concentration required to achieve beneficial stabilization would lead to loss of activity. In such cases, binding compounds that bind to the polypeptide outside of the active site (also known as "exosites") may be employed. For example, high affinity specific binding anywhere on the surface of a polypeptide may confer stabilization as a result of the increased number of interactions. To identify suitable sites that are available to bind small molecule chaperones (e.g., sites that are not tightly bound to water molecules that prevent access to many sites of the protein surface (Ringe D. (1995) *Curr. Opin. Struct. Biol.* 5:825-829), these sites can be mapped crystallographically (Mattos et al. (2006) *J. Mol. Biol.* 357:1471-1482) and computationally (Landon et al. 2009 *J. Comput. Aided Mol. Des.* 23:491-500) for example using the atomic coordinates provided herein. Suitable exosites may be identified in silico and libraries of small organic compounds can be tested for compounds that bind to the exosite. The predicted binders may be screened for thermal stabilization of the enzyme using, e.g., in a fluorescence-based assay. A successful binding may increase thermal stabilization by one or several degrees (e.g., 1° C., 2° C., 3° C., 4° C., 5° C., 6° C., 7° C., 8° C., 9° C., 10° C., or more).

Mutant proteins (partially or fully folded) that are stabilized by chemical chaperones can be transported out of the endoplasmic reticulum more efficiently and may avoid intracellular degradation (Amaral (2006) *J. Inherited Metabol. Dis.* 29:477-487; Lieberman et al. (2007) *Nat Chem Biol* 3:101-107; Steet et al. (2006) *Proc Natl Acad Sci USA* 103:13813-13818; Tropak et al. (2004) *J Biol Chem* 279: 13478-13487; Sawkar et al. (2002) *Proc Natl Acad Sci USA* 99:15428-15433; Fan J Q, et al. (1999) *Nat Med* 5:112-115; Asano et al. (2001) *Med Chem* 1:145-154). Mutant lysosomal enzymes that are unstable, including NAGLU mutants, may be retained in the endoplasmic reticulum by cellular quality control mechanisms and fail to traffic to lysosomes leading to their aggregation and or degradation (Ellgaard et al. (1999) *Science* 286:1882-1888; Yogalingam et al. (2000) *Biochim Biophys Acta* 1502:415-425; Lieberman et al. (2007) *Nat Chem Biol* 3:101-107; Steet et al. (2006) *Proc Natl Acad Sci USA* 103:13813-13818; Tropak et al. (2004) *J Biol Chem* 279:13478-13487; Sawkar et al. (2002) *Proc Natl Acad Sci USA* 99:15428-15433; Fan et al. (1999) *Nat Med* 5:112-115; Asano et al. (2001) *Med Chem* 1:145-154). Analogous to what has been suggested for genetic disorders, such as Fabry disease and cystic fibrosis, the use of compounds that can elicit the proper folding and trafficking of mutant proteins might prove to be an effective strategy for the treatment of genetic disorders such as mucopolysaccharidosis III B (MPS III-B). A functional compound that can elicit the correct folding of a mutant protein may serve as a specific chemical chaperone for the mutant protein to promote the successful escape from the ER quality control mechanisms (Fan et al. (1999) *Nat Med.* 5:112-5). A chemical chaperone therapy such as it was shown in Fabry disease may also be applicable to other type of lysosomal storage diseases. Inhibitors of lysosomal glycosidases may be used as chemical chaperones to bind to and stabilize mutant NAGLU, aiding or facilitating NAGLU maturation and trafficking of NAGLU to lysosomes. Such inhibitors can be reversible inhibitors. Once in the lysosome, some NAGLU mutant enzymes may have sufficient catalytic activity to support normal cellular functioning. Mucopolysaccharidosis III B (MPS treatment may be aided by chemical chaperones acting on mutant NAGLU. It should be appreciated that chemical chaperones or other binding compounds may bind to NAGLU outside the active site. In certain embodiments, chemical chaperones are provided that bind to sites that are outside of the binding site. Such sites may be anywhere on the NAGLU polypeptide and may be located, for example, directly at or immediately adjacent to NAGLU mutations associated with MPS III-B. Other suitable binding locations for chemical chaperones or other compounds may be further removed from the site(s) of mutation. The distance to the site of mutation may be determined either by the number of intervening amino acids between the one or more altered or mutated residues and the one or more residues of the binding site according to the primary structure, or may be determined as physical distance according to the three-dimensional (tertiary) structure.

The three-dimensional structural information provided herein will aid in the identification and development of novel compounds which may possess chaperone activity that may lead for example to a stabilization of the mutated NAGLU enzyme, which may prevent rapid turnover (degradation), may prevent aggregation, may increase the enzymatic activity of the NAGLU enzyme and/or may determine the sub-cellular localization of the NAGLU enzyme. With the help of the three-dimensional structural information provided herein efficient chemical chaperones that specifically target NAGLU to treat MPS III-B may be identified, designed and developed.

Combination of Approaches to Treat Mucopolysaccharidosis III B (MPS III-B)

Methods to treat MPS III-B may involve naglu gene replacement, NAGLU enzyme replacement strategies, interference with NAGLU glycosylation, and/or the use of chemical chaperones as well as combinations of these approaches, and these approaches may be used alone or in combination with additional intervention strategies. For example, gensteine, an inhibitor of glycosaminoglycan (GAG) synthesis, that is able to cross the blood-brain-barrier has been investigated in vitro on MSP III-B derived fibroblasts and has been shown to inhibit GAG synthesis in these cells (Malinowska et al. (2009) *Mol Genet Metab.* 98:235-42). Such approaches may help to minimize GAG accumulation as a consequence of reduced or missing enzymatic activity of NAGLU mutants.

Design, Identification, and Screening of Potential NAGLU Binding Compounds

It is one object of the present invention to use the atomic coordinates of NAGLU (Table 3) to design, identify, and screen potential binding compounds that bind to NAGLU or a related member of the family 89 glycoside hydrolases (α-N-acetylglucosaminidases) and alter NAGLU's physical, chemical, and/or physiological properties. Novel compounds obtained from this screen may further be identified as being able to restore (partially or fully) aspects of GAG degradation in vitro for example in assays involving in cell lines expressing mutated NAGLU or in biochemical assays, for example, using buffered enzyme/substrate systems. In another embodiment, novel compounds obtained from this screen may be identified as being able to treat mucopolysaccharidosis III B (MPS III-B) in human subjects.

The atomic coordinates of NAGLU (Table 3) can also be used to computationally screen for small molecule compounds that bind to NAGLU and/or a NAGLU family member in order to select, design, and develop potential binding compounds of NAGLU and/or a NAGLU family member. It should be understood that a potential binding compound according to this invention may bind to an active site or any other site which is not identified as an active site. In certain embodiments, the potential binding compound according to this invention may bind specifically to one or more sites on the NAGLU polypeptide (be it nascent, partially or fully folded) where mutations have occurred. In certain embodiments, the potential binding compounds according to this invention function as chemical chaperones. It should be appreciated that binding compound other than chemical chaperones or small molecular weight compounds could be used. For example, certain polypeptides may be used to stabilize the NAGLU polypeptide. Such polypeptides may have chaperone or co-chaperone activity and may comprise fragments of cellular chaperones or co-chaperones or the polypeptides may comprise full-length cellular chaperones. Cellular chaperones and co-chaperones may include eukaryotic or prokaryotic chaperones and co-chaperones, such as mammalian chaperones and co-chaperones and bacterial chaperones and co-chaperones, respectively. Other chaperones and co-chaperones, e.g., from yeast or insects may also be useful. Useful chaperone activity may be provided by polypeptides comprising amino acid sequences based on fragments or protein domains of Hsp60 (GroEL/GroES complex in *E. coli*), Hsp70 (DnaK in *E. coli*), Hsp90 (HtpG in *E. coli*), Hsp100 (Clp family in *E. coli*), and others such as BiP, GRP94, or GRP 170.

In certain embodiments, the potential binding compound is a potential inhibitor or activator compound. In certain embodiments, the potential binding compound is a potential NAGLU (mutant NAGLU) inhibitor or activator compound. In certain embodiments, the potential inhibitor or activator compound is a competitive, uncompetitive or non-competitive inhibitor or activator compound. In certain embodiments, the potential inhibitor is a reversible inhibitor. Those of skill in the art may identify potential inhibitors or activators as competitive, uncompetitive or non-competitive or reversible inhibitors or activators by computer fitting enzyme kinetic data using standard equations according to, for example, Enzyme Kinetics by Segel (1975) J. Wiley & Sons, incorporated herein by reference, or by employing assays which measure the ability of a potential inhibitor or activator to modulate NAGLU (mutant NAGLU) enzymatic activity (e.g., hydrolysis of terminal N-acetyl-D-glucosamine residues in N-acetyl-alpha-D-glucosaminides). Examples of N-acetylglucosaminidase inhibitors are: 2-acetamido-1,2-dideoxynojirimycin (2AcDNJ) (Horsch et al. (1991) *Euro. J. Biochem.* 197:815-818), O-(2-acetamido-2-deoxy-D-glucopyranosylidene)amino-N-phenylcarbamate (PUGNAc) (Beer et al. (1990) *Helv Chim Acta* 73:1918-1922), and 6-acetamido-6-deoxycastanospermine (6Ac-CAS) (Liu et al. (1991) *Tetrahedron Lett* 32:719-720). Reversible inhibitors may be particularly useful. Inhibitor or activator compounds may bind to the active site or may associate with sites outside of the active site (exosites). Inhibitor or activator compounds whether bound to the active site or bound to exosites may help to stabilize the NAGLU (mutant NAGLU) polypeptide.

It should be appreciated that enhancers of NAGLU enzymatic activity may also be used. Enhancers of NAGLU enzymatic activity may not need to be NAGLU binding compounds, but may be compounds that have effects on molecules other than NAGLU. Enhancers may, for example, increase cellular trafficking of NAGLU by changing the intracellular milieu, the permeability and/or composition of cell organelles or transporters.

In one embodiment, the present invention provides a method for the design and identification of a potential binding compound for NAGLU and/or a NAGLU family member, comprising the steps of: (a) using a three-dimensional structure of NAGLU as defined by the atomic coordinates provided in Table 3; (b) employing the three-dimensional structure to design and/or select the potential binding compound; and (c) synthesizing and/or choosing the potential binding compound.

Suitable computer programs which may be used in the design and selection of potential binding compounds (e.g., by selecting suitable chemical fragments) include, but are not limited to, GRID (Goodford (1985) *J. Med. Chem.* 28:849 857); MCSS (Miranker, A. and M. Karplus, (1991) *Proteins: Structure. Function and Genetics,* 11:29-34); AUTODOCK (Goodsell, D. S, and A. J. Olsen (1990) *Proteins: Structure. Function, and Genetics* 8:195 202); and DOCK (Kuntz, I. D. et al. (1982) *J Mol. Biol.* 161:269-288), the entirety of each of which is incorporated herein by reference.

Suitable computer programs which may be used in connecting the individual chemical entities or fragments include, but are not limited to, CAVEAT (Bartlett, (1989) *Molecular Recognition in Chemical and Biological Problems,* Special Pub., Royal Chem. Soc. 78:182-196); and 3*D Database systems such as MACCS*-3*D* by MDL Information Systems, San Leandro, Calif.), HOOK (Molecular Simulations, Burlington, Mass.) and as reviewed in Martin, Y. C., (1992) *J. Med. Chem.* 35:2145 2154), the entirety of each of which is hereby incorporated herein by reference.

In addition to the method of building or identifying a potential binding compound in a step-wise fashion (e.g., one fragment or chemical entity at a time as described above), potential binding compounds may be designed as a whole or "de novo" using either an empty active site or, optionally, including some portion(s) of a known inhibitor(s), activator(s) or stabilizer(s). Suitable computer programs include, but are not limited to, LUDI (Bohm, (1992) *J. Comp. Aid. Molec. Design* 6:61-78); LEGEND (Nishibata, Y. and A. Itai, (1991) *Tetrahedron* 47:8985); and LEAP-FROG (Tripos Associates, St. Louis, Mo.). Other molecular modeling techniques may also be employed in accordance with this invention; see, for example, Cohen, N. C. et al. (1990) *J. Med. Chem.* 33: 883-894, and Navia (1992) *Current Opinions in Structural Biology* 2:202-210, the entirety of each of which is hereby incorporated herein by reference.

Once a potential binding compound has been designed, selected, identified, synthesized, or chosen by the methods described herein, the affinity with which that compound binds to NAGLU and/or a NAGLU family member may be tested and optimized by computational evaluation. A compound designed, or selected, or synthesized, or chosen as potential binding compound or may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the potential binding compound and the site at which it is bound to NAGLU and/or a NAGLU family member, in certain embodiments, make a neutral or favorable contribution to the enthalpy of binding. Suitable computer software which may be used to evaluate compound deformation energy and electrostatic interactions, includes, but is not limited to, *Gaussian* 92*, revision C* by M. J. Frisch, Gaussian, Inc., (1992) Pittsburgh, Pa.; AMBER, version 4.0 by P. A. Kollman, (1994) University of California at San Francisco; *QUANTA/CHARMM* by Molecular Simulations, Inc., (1994) Burlington, Mass.; and *Insight II/Discover* by Biosym Technologies Inc., (1994) San Diego, Calif. These programs may be implemented, for example, using a Silicon Graphics workstation, IRIS 4D/35 or IBM RISC/6000 workstation model 550. Hardware systems, such as an IBM thinkpad with LINUX operating system or a DELL latitude D630 with WINDOWS operating system, may be used. Other hardware systems and software packages will be known to those skilled in the art of which the speed and capacity are continually modified.

In certain embodiments, binding compounds may be specifically designed and/or selected and/or synthesized and/or chosen by the above methods to induce non-complementary (e.g., electrostatic) interactions, such as repulsive charge-charge, dipole-dipole and charge-dipole interactions. In certain embodiments, the sum of all electrostatic interactions between the potential binding compound and the site at which it is bound to NAGLU and/or a NAGLU family member make a contribution to the enthalpy of binding that is not neutral.

In certain embodiments, the above method comprises using a suitable computer program in designing and/or selecting a potential binding compound.

Additionally, in certain embodiments, the above method comprises using a suitable computer program in conjunction with synthesizing and/or choosing the potential binding compound.

Furthermore, in certain embodiments, the above method further comprises the steps of using a suitable assay, as described herein, to characterize the potential binding compound's influence on NAGLU activity, stability, folding, and/or intracellular localization. In certain embodiments, the above method further comprises: (d) contacting the potential binding compound with mutated NAGLU and/or a related mutated NAGLU family member in the presence of a substrate; and (e) determining the amount of substrate conversion of the mutated from compared to a wild-type (non-mutated) NAGLU to determine the effect of the potential binding compound on NAGLU enzymatic activity.

Alternatively, in certain embodiments, the above method further comprises the steps of: (d) contacting the potential binding compound with a cell that expresses mutated NAGLU; and (e) determining the effect of the binding compound on NAGLU activity in the cell. In certain embodiments, step (e) may comprise determining the effect of the binding compound on intracellular localization of NAGLU. In certain embodiments, step (e) may comprise determining the effect of the binding compound on intracellular concentration of NAGLU (e.g., determining the rate of turnover/degradation of NAGLU in the cell).

It is another object of the invention to provide methods for solving the structures of other proteins which belong to NAGLU or NAGLU family member that comprise one or more mutations (as referenced in Table 4), such as missense, nonsense, and/or deletion mutations that may be associated with MPS III-B, that may have been identified in the naglu gene without being associated with MPS III-B, and/or that are thought to reduce NAGLU stability and resulting in less functional enzyme reaching the lysosome. Structures of crystallized proteins comprising such alterations in the primary amino acid sequence as well as NAGLU orthologs or homologs of other organisms sharing some sequence homology and/or identity to the primary amino acid sequence of NAGLU may be solved by molecular replacement with NAGLU structural information provided by the present invention (Table 3).

In certain embodiments, the present invention provides a method for solving the structure of NAGLU, mutated NAGLU or a NAGLU family member comprising the steps of: (a) collecting X-ray diffraction data of a NAGLU crystal complexed to a binding compound (such as a chaperone), a NAGLU mutant crystal or a NAGLU-family member crystal; (b) using the atomic coordinates of NAGLU according to Table 3 to perform molecular replacement with the X-ray diffraction data of the NAGLU crystal complexed to a binding compound, a NAGLU mutant crystal or a NAGLU-family member crystal; and (c) determining the structure of NAGLU crystal complexed to a binding compound, a NAGLU mutant crystal, or a NAGLU-family member crystal.

Additionally, the present invention provides a method of evaluating the binding properties of a potential binding compound comprising the steps of: (a) soaking a potential binding compound with crystalline NAGLU, crystalline NAGLU mutant or a crystalline NAGLU family member to provide a crystalline NAGLU complexed to a binding compound, a crystalline NAGLU mutant complexed to a binding compound or a crystalline NAGLU-family member complexed to a binding compound; (b) determining the three-dimensional structure of the crystalline NAGLU complexed to the binding compound, the crystalline NAGLU mutant complexed to the binding compound or the crystalline NAGLU-family member complexed to the binding compound by molecular replacement using the three-dimensional structure of NAGLU as defined by atomic coordinates according to Table 3; and (c) analyzing the three-dimensional structure of the crystalline NAGLU complexed to the binding compound, the crystalline NAGLU mutant complexed to the binding compound or the crystalline NAGLU-family member complexed to the binding compound to the unbound potential binding compound to evaluate the binding characteristics of the potential binding compound. To evaluate binding properties of binding compounds, assays may be used, such as, calorimetric techniques (e.g. isothermal titration calometry, differential scanning calometry), or Biacore™ can be used for initial screening. Other assays are known in the art. For further optimization, co-crystallization may be useful to determine the structure of NAGLU-binding compound complexes.

It is yet another object of the invention to provide methods for solving the structures or partially solving the structure of other proteins which comprise protein domains of similar function, other homology domains, or proteins that comprise amino acid sequences of high homology or identity. Such protein structures may be solved using some or all of the structural information provided in Table 3). In some embodiments, molecular replacement methods may be employed to solve such structures using the structural information provided by the present invention (Table 3).

EXAMPLES

The present invention will be more specifically illustrated by the following examples. However, it should be understood that the present invention is not limited by these examples in any manner.

Example 1

Crystallization and Structure Determination of NAGLU

Described herein is the crystallization and determination of structure of α-N-acetylglucosaminidase (NAGLU) at a resolution of 2.9 Å and 2.4 Å by X-ray crystallography.

1.1. Experimental Design

NAGLU was expressed in HT1080 cells that were cultured at 37° C. to 2-3 million cells per mL. The temperature was decreased to 33° C. and the culture was treated with 2.5 mg/L of kifunensine (a mannosidase I inhibitor). Conditioned media containing secreted NAGLU was harvested 48 hours after starting kifunensine treatment. The resulting protein is abbreviated as Naglu-kif. Secreted protein was purified from culture media by hydrophobic butyl column followed by anion exchange Q column (as described in Example 3).

While purifying NAGLU-kif, a fine precipitate appeared at the final concentrating step. At this stage the protein was in Q column buffer which is 20 mM Tris pH=7.5 and approximately 100 mM NaCl. The precipitation started appearing at the bottom of the concentrator when protein concentration was over 1 mg/mL. Concentrating process was stopped at that point, the protein was taken out of concentrator and stored at 4° C. Next day morning more crystalline precipitation was observed and when checked under optical microscope these precipitates were found to be needle shaped crystals of 50-100 micron size in the longest dimension (FIG. 1). These crystals were dissolving slowly when incubated at room temperature, which indicated that the protein was at the solubility limit and crystallizes out upon lowering the temperature to 4° C.

A crystal of 100×20×20 micron size was tested in X-ray diffractometer at Beth Israel Deaconess Medical Center (BIDMC) X-ray Crystallography Facility at room temperature. This crystal diffracted to a maximum resolution of 3.5 Å upon long exposure of 30 min per frame on an in-house rotating anode X-ray beam. Unit cell parameters could be calculated from this diffraction image. Naglu-kif crystal belongs to hexagonal space group with dimensions a=b=207.5 Å, c=79.6 Å, α=β=90° and γ=120°. Longer exposure on x-ray beam at room temperature damaged the crystals which prevented the collection of a complete dataset and structure determination. However, from the diffraction pattern and unit cell parameters it was confirmed that the crystals are actually made of NAGLU protein and had a calculated solvent content of about 80%.

Crystallization screening and optimization were carried out at BIDMC X-ray Crystallography facility, in order to grow crystals of sufficient quality and size that would facilitate collection of a complete diffraction data set. Optimization of cryo-conditions to freeze the crystals at liquid-$N_2$ temperature was also carried out to collect diffraction data at liquid $N_2$ temperature that would attenuate the radiation damage of crystals.

X-ray diffraction data collection and processing were done at BIDMC X-ray Diffraction Facility (2.9 Å data collection) and Brookhaven National Laboratory (3.2 Å and 2.4 Å data collection). Structure determination, model building and refinement were done using software such as Molrep, coot and Refmac that were part of CCP4 software suite. MolRep is a program for automated molecular replacement (MolRep, version 10.2.35). Coot Graphical Interface by Paul Emsley (www.ysbl.york.ac.uk/~emsley) for model building includes an interface to refmac5 and is freely available (Gnu Public License). Refmac5 (version 5.5.0072 and 5.5.019). Macromolecular refinement program by Garth Murshudov et al. is integrated into the CCP4 program suite (www.ccp4.ac.uk) (CCP4 version 6.1.3). Structural analyses were done using molecular viewer software PYMOL (www.pymol.org). Initial processing (indexing/integration/scaling) was performed using HKL2000 (HKL Research, Inc., Charlottesville, Va.).

1.2 Research Methods 1.2.1 Crystallization Screening and Cryo Optimization

Initial crystals of Naglu-kif were obtained serendipitously during protein purification when Q column fractions were concentrated on Vivaspin20 concentrators with 10 kDa molecular weight cut-off. These initial crystals were not of high enough quality and size that they could be used for complete diffraction data collection.

In order to generate crystals of sufficient quality two different approaches were undertaken. 1) Naglu-kif was screened for new crystallization conditions using random matrix crystallization screening kit. 2) NAGLU-kif crystals that appeared in Q column buffer (20 mM Tris pH=7.5 and 100 mM NaCl) were dehydrated by equilibrating against the same buffer containing 30% PEG 8000 in a sitting drop vapor diffusion tray to improve the diffraction limit.

Naglu-kif (1 mg/mL in PBS) was first dialyzed to 20 mM Tris pH=7.5 and 100 mM NaCl in dialysis buttons. The dialyzed protein was used to screen for new crystallization conditions using Qiagen NeXtal Classic Suite crystal screen kit (Qiagen catalog#130701; QIAGEN Inc., Valencia Calif.) and sitting drop vapor diffusion method. Crystal hits were seen in many different conditions and are summarized in Table 1. Crystals from condition #58 (0.01 M nickel chloride, 0.1 M Tris, pH 8.5, 1.0 M lithium sulfate) were thick and were used to collect a 3.2 Å diffraction data-set at synchrotron beam.

TABLE 1

Composition of crystallization buffers from Qiagen NeXtal Classic Suite that gave crystal hits.

| Condition No. | Salt | Buffer | Precipitant-1 | Precipitant-2 | Notes |
| --- | --- | --- | --- | --- | --- |
| 58 | 0.01M Nickel chloride | 0.1M TRIS pH 8.5 | 1.0M Lithium sulfate | | thick needle crystals |
| 63 | | 0.1M TRIS. HCl pH 8.5 | 8% (w/v) PEG 8000 | | thin needle crystals |
| 64 | | 0.1M HEPES pH 7.5 | 10% (w/v) PEG 8000 | | thin needle crystals |
| 66 | 0.2M Zinc acetate | 0.1M Sodium cacodylate pH 6.5 | 18% (w/v) PEG 8000 | | tiny dot cystals |
| 73 | 2.0M Ammonium sulfate | 0.1M HEPES sodium salt pH 7.5 | 2% (v/v) PEG 400 | | precipitate/thin needles |
| 78 | 0.1M Sodium chloride | 0.1M BICINE pH 9.0 | 20% (w/v) PEG 550 MME | | very thin needle crystals |
| 79 | 0.01M Zinc sulfate | 0.1M MES pH 6.5 | 25% (w/v) PEG 550 MME | | tiny dot crystals |
| 82 | 0.01M Nickel chloride | 0.1M TRIS pH 8.5 | 20% (w/v) PEG 2000 MME | | thin needle crystals |
| 93 | | 0.1M HEPES pH 7.5 | 10% (w/v) PEG 6000 | 5% (v/v) MPD | thin needle crystals |
| 96 | | 0.1M MES pH 6.5 | 12% (w/v) PEG 20000 | | thin needle crystals |

Since the NAGLU crystals had high solvent content, dehydrating the crystals was tried to improve the diffraction limit. For dehydration, the crystals that appeared in Q column buffer, were equilibrated against the same buffer containing 30% PEG 8000 in a sitting drop vapor diffusion tray. In a typical experiment, 20 μl of suspension containing needle crystals in 20 mM Tris pH=7.5 and 100 mM NaCl was equilibrated for 2 days against one mL of 20 mM Tris pH=7.5, 100 mM NaCl and 30% w/v PEG8000 in a sitting drop vapor diffusion tray at room temperature. The resulted crystals were about 150×50×50 micron in size and were used for screening cryo-condition.

For cryo-protection, crystallization buffers containing 20-35% v/v of polyols, such as glycerol, ethylene glycol or MPD or 35-70% w/v of sugars, such as sucrose or xylitol were tried. Crystals were soaked in the cryo-buffer for 5-15 minutes and visually checked for crystal integrity. Cryo-protected crystal were frozen in a liquid $N_2$ stream on an in-house X-ray diffractometer and tested for diffraction quality. Crystals grown in condition #58 (0.01 M nickel chloride, 0.1 M Tris, pH 8.5, 1.0 M lithium sulfate, Table 1) were cryo-protected with crystallization buffer containing 25% glycerol and frozen in liquid nitrogen before collecting data at the synchrotron beam. Best cryo-protection for crystals grown in Q column buffer was achieved when a cryo-containing glycerol and xylitol (20 mM Tris pH=7.5, 100 mM NaCl, 15% glycerol, and 20% xylitol) buffer was used, which gave a diffraction resolution of 2.9 Å at the in-house x-ray diffractometer and 2.4 Å at synchrotron beam.

1.2.2 Diffraction Data Collection and Structure Determination

X-ray diffraction data collection and initial processing were done at Beth Israel Deaconess Medical Center (BIDMC) x-ray crystallography facility. Three diffraction data sets were collected for NAGLU crystals, first a 3.2 Å data set at synchrotron beam, then a 2.9 Å data set at in-house X-ray diffractometer and finally a 2.4 Å data set at synchrotron beam. The 3.2 Å data was collected for a crystal grown in condition #58 (0.01 M nickel chloride, 0.1 M Tris, pH 8.5, 1.0 M lithium sulfate, Table 1) and cryo-protected with 25% glycerol. For 2.9 Å data set, a cryo-protected crystal was mounted on Rigaku RUH3R in-house X-ray diffractometer (Rigaku Americas Corporation, The Woodlands, Tex.) equipped with R-AXIS-IV image plate. Diffraction data were collected with 1° oscillation and 120 frames were collected at 5 min exposure per frame. Data merging and scaling were done using HKL2000 (HKL Research, Inc., Charlottesville, Va.). Initial model of NAGLU was obtained by molecular replacement method using the program Molrep and CpGH89 structure (PDB ID: 2VCC) as search model. All the side chains were removed from the coordinates of CpGH89 and the resulting poly-alanine model was used to get the initial phases. Further model building and refinement were done using coot and Refmac respectively. For the 2.9 Å data-set, the model was refined to a final R factor of 18.7% and $R_{free}$ of 22.9%. For the 2.4 Å data-set, the model was refined to a final R factor of 17.46% and $R_{free}$ of 19.81%.

Example 2

2.1 Crystallization and Cryo Protection

Initial crystals of Naglu-kif were obtained when purified protein was concentrated above 1 mg/mL. These crystals were confirmed to be made of NAGLU protein by testing the crystals in X-ray diffraction at room temperature. These crystals were too small to collect a complete data set and were diffracting to only ~3.5 Å after 30 min exposure per frame. Radiation damage of protein crystal occurred due to long exposure on X-ray beam at room temperature that resulted in poor diffraction resolution in subsequent frames. Moreover the higher solvent content (about 80%) in the crystals caused damage to the crystal due to shock when transferred into cryo-buffer. These issues warranted further optimization of crystallization and cryo-protection in order to get a complete diffraction data set.

Naglu-kif R3 was dialyzed overnight against 20 mM Tris pH=7.5 and 100 mM NaCl and concentrated to 1.2 mg/mL. Crystallization screening was done for Naglu-kif using random matrix crystallization screening kits from Qiagen (NeXtal Classic Suite) by sitting drop vapor diffusion method. Since the protein was in near saturation, crystal hits were seen in many different conditions in the pH range of 6.5 to 9.0 that included PEG conditions as well as a salt condition (Table 1).

Crystals grown in crystallization buffer containing PEG did not diffract well in in-house X-ray diffractometer at room temperature. A lithium sulfate condition (condition #58, 0.01 M nickel chloride, 0.1 M Tris, pH 8.5, 1.0 M lithium sulfate) was giving bigger crystals of up to 200-300×50×50 micron. One of these crystals, cryo-protected in crystallization buffer containing 25% glycerol, diffracted to 3.2 Å at synchrotron beam (Brookhaven National Laboratory, Upton, N.Y.). Lower resolution of such a large crystal was mainly due to crystal damage upon freezing in the cryo-protectant. Nonetheless this 3.2 Å data set was sufficient to solve the structure of NAGLU using the molecular replacement method. Analysis of this 3.2 Å structural model confirmed that there is one molecule in the asymmetric unit of NAGLU crystals and thus the crystals are made of 79% solvent and only ~20% of protein mass. Such a large solvent content caused the crystal to damage easily when transferred to cryo-buffer that resulted in poor diffraction resolution. In order to improve the resolution of the structure beyond 3.2 Å, additional screening of cryo-conditions was carried out.

NAGLU crystals grown in 20 mM Tris pH=7.5 and 100 mM NaCl buffer were of medium size, in the order of 150×50×50 micron. These crystals were used to screen for better cryo-conditions as sufficient number these crystals were available and these crystals were dehydrated by equilibrating against buffer containing 30% PEG 8000. Moreover, medium sized crystals are known to tolerate the shock well when transferred into cryo-buffer.

In the first round of cryo-screening, crystals were soaked for 5 min in crystallization buffer 20 mM Tris pH=7.5, 100 mM NaCl containing 20, 25 or 30% v/v of glycerol, ethylene glycol or 2-Methyl-2,4-pentanediol. Crystals were visually inspected for the integrity before freezing and checked for diffraction after freezing in liquid nitrogen stream on a rotating anode X-ray diffractometer. At 20% cryo-protectant there were ice rings on the diffraction image and at 25 and 30% diffraction spots were split, an indication of crystal damage as well as diffraction resolutions were low.

For the second round of screening, sucrose or xylitol was used as cryo-protectant. When added to 35% w/v to the crystallization buffer ice ring was seen in the diffraction image. Ice rings disappeared when the sugar was increased to 70% w/v in the crystallization buffer, however loss of diffraction resolution was noticed when compared to the diffraction limit obtained for a similar crystal at room temperature.

When the crystals were soaked in a cryo-buffer containing 15% glycerol and 20% xylitol in 20 mM Tris pH=7.5 and 100 mM NaCl and dehydrated for 15 min at room temperature the resulted crystals diffracted better than 3 Å with well defined spherical diffraction spots. In one experiment 2-4 crystals were transferred into a well containing 200 µl of cryo-buffer (20 mM Tris pH=7.5, 100 mM NaCl, 15% glycerol and 20% xylitol) and soaked for 15 min. The well containing crystals in the cryo-buffer, was left open facilitating dehydration as well as annealing of the crystals.

Cryo-protected crystals were frozen in liquid nitrogen stream on a rotating anode X-ray diffractometer. Some of these crystals were frozen in liquid nitrogen for data collection at synchrotron beam.

Diffraction data were collected at in-house X-ray diffractometer with 1° oscillation and 5 minute exposure per frame. A total of 120 frames were collected in the phi region predicted by HKL2000 strategy simulation for better completeness. The 2.4 Å data was collected at synchrotron beam with 1° oscillation and 3 second exposure and a total of 165 frames were collected. Data was indexed to a hexagonal P6$_3$ space group, merged and scaled in HKL2000 software suite.

2.2 Structure Determination

The processed hkl file from HKL2000 was imported into the CCP4 software suite and 5% of the data was set aside for R$_{free}$ calculation. Initial phase information was obtained by Molecular replacement (MR) method using the program "Molrep" and the structure of CpGH89 (PDB ID: 2VCC) as search model.

Figure 2:
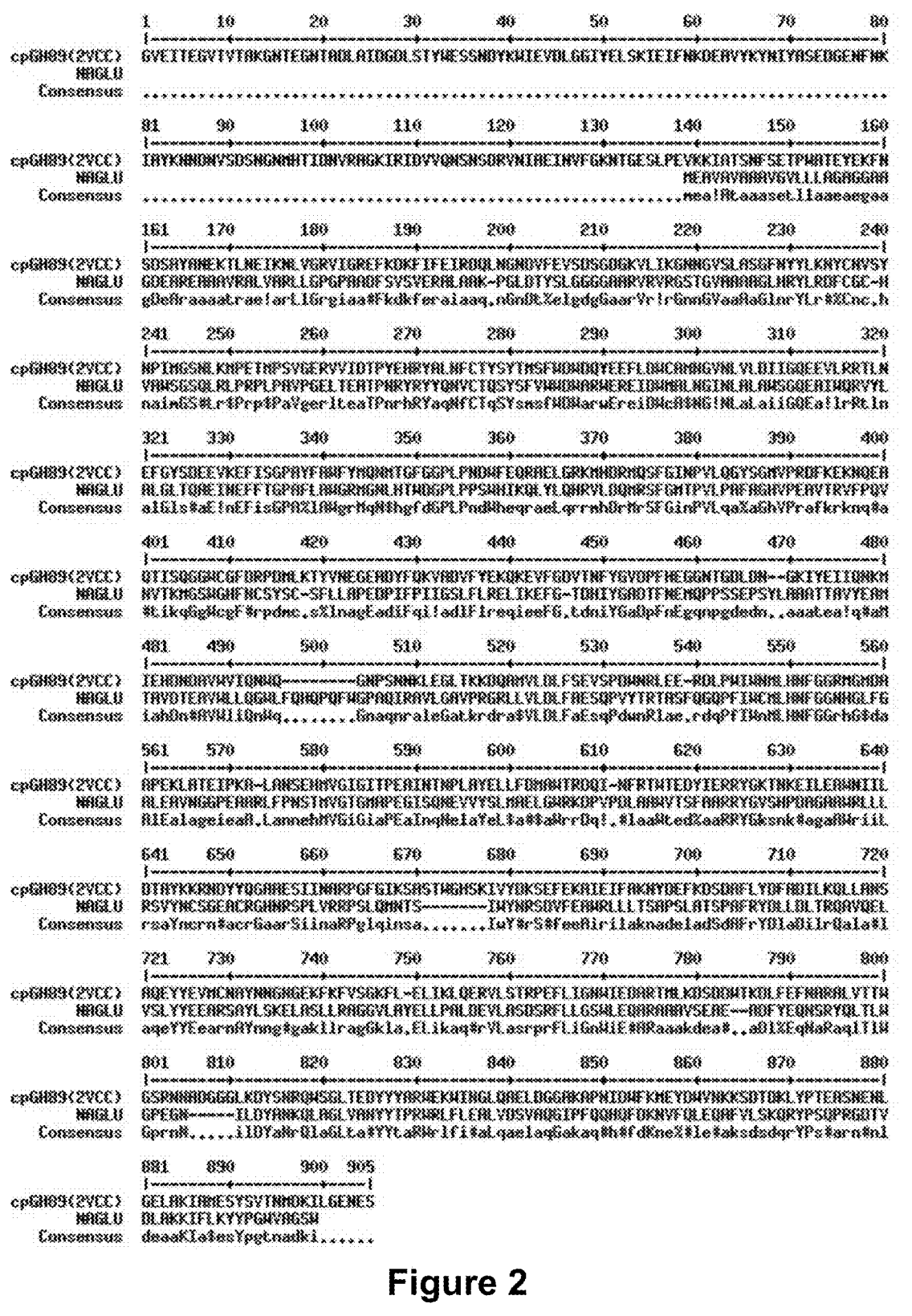

Structure of CpGH89, a bacterial homolog of NAGLU has been reported recently (Ficko-Blean et al. *Proc Natl Acad Sci USA*, 2008, 105:6560-5). It has a sequence identity of about 30% (FIG. 2) and belongs to the same class of enzyme as NAGLU. CpGH89 has an extra carbohydrate binding domain (CBD) of about 130 amino acids at the N-terminus. The CBD of CpGH89 as well as all the side chains were removed and only the poly-alanine model of CpGH89 was used in Molrep to find the initial MR phases for NAGLU.

A clear solution was obtained from rotational and translational search in Molrep. The resulted electron density map was continuous and most of the side chains could be build on this map. All the model building was done using graphical model building software "coot". Loop regions were removed from this initial model and side chains were modeled wherever the electron densities were clear. Refinement was done for the resulting partial model using Refmac in CCP4, which improved the electron density map. Model building in coot and refinement using Refmac were repeated iteratively until a complete model was built on the electron density map. The final model of NAGLU obtained from the 2.9 Å crystal structure contained all the amino acids, from amino acid 24-743, including six glycans at positions N261, N272, N435, N503, N526 and N532. In 2.9 Å structure, the electron density obtained for the glycans attached to asparagine residues suggests at least one N-acetylglucosamine molecule each on N272, N526 and N532, two N-acetylglucosamine molecules each on N435 and N503, and two N-acetylglucosamine molecules and one mannose residue on N261. In 2.4 Å structure, the electron density obtained for the glycans attached to asparagine residues suggests at least one N-acetylglucosamine molecule attached to N261, N503, N526 and N532, and at least two N-acetylglucosamine molecules on N272 and N435. The final model at 2.9 Å has a R and R$_{free}$ of 18.7 and 22.9%, respectively, and at 2.4 Å has a R and R$_{free}$ of 17.46% and 19.81%, respectively, and other structural parameters are summarized in Table 2.

TABLE 2

Structure data of Naglu-kif

| Space Group | P6$_3$ | P6$_3$ |
|---|---|---|
| Cell dimensions | a = b = 205.66 Å; c = 78.69 Å; α = β = 90°; γ = 120° | a = b = 205.13 Å; c = 78.44 Å; α = β = 90°; γ = 120° |
| Resolution (Å) | 47.4-2.9 | 42.92-2.4 |
| No. of Reflections | 40230 | 69635 |
| Completeness (%) | 99.84 | 99.27 |
| Refinement: | | |
| R-Factor (%) | 18.7 | 17.46 |
| R$_{free}$ (%) | 22.9 | 19.81 |
| No. of non-hydrogen atoms | 5965 | 6170 |
| Mean B Value (Å$^2$) | 36.8 | 41.5 |

2.3 Summary

Others have hypothesized in the literature that NAGLU was difficult to crystallize mainly because of difficulty in generating a large enough quantity of pure and homogeneous protein as well as inherent difficulty in generating crystals for proteins with heterogeneous complex glycosylation. Naglu-kif could readily be crystallized due to its higher purity, limited solubility and thus an increased tendency to crystallize at a concentration above about 1 mg/mL. Recombinant human NAGLU (rhNAGLU) expressed in HT1080 cells, which has trimmed glycans due to the presence of mannosidase-I in the HT1080 cells expressing naglu, has higher solubility and could be concentrated to up to 28 mg/mL. When rhNAGLU was concentrated above about 28 mg/mL, some crystalline precipitation was observed indicating that even rhNAGLU could be crystallized when concentrated close to its solubility limit.

Initial crystals of Naglu-kif gave low diffraction resolution on X-ray beam due to small size and high solvent content in the crystals. Dehydrated and cryo-protected crystals could successfully be used to get a complete diffraction set to a resolution of 2.9 Å in a rotating anode diffractometer and to a resolution of 2.4 Å in a synchrotron beam.

NAGLU crystal structure has been solved for the first time at a resolution of 2.4 Å. The crystals belong to the hexagonal P6$_3$ space group with one molecule in the asymmetric unit (FIG. 3). There are three domains in NAGLU and the catalytic site lays in domain II which is a (α/β)$_8$ barrel domain. Catalytic residues E316 and E446 are about 6 Å apart indicating that the acid/base catalysis follows a retaining double displacement mechanism similar to other members of the family 89 glycoside hydrolases (α-N-acetylglucosaminidases). When crystallographic symmetry parameters are applied to the molecule, a trimeric arrangement of NAGLU could been seen which is formed by the interaction of domain II (FIG. 4). This trimeric form is known to exist in solution from other experimental data including analytical ultra centrifugation, dynamic light scattering, and size exclusion chromatography. The crystal structure obtained allows for analyses and mapping of Sanfilippo syndrome type B (mucopolysaccharidosis III B (MPS III-B)) mutations in the NAGLU structure.

Example 3

Expression and Purification of NAGLU-Kif

Described in this Example is the expression in HT1080 cells and purification of NAGLU-kif, a recombinant human α-N-acetylglucosaminidase, cultured in a medium containing kifunensine, a potent inhibitor of alpha-mannosidase I.

3.1. Experimental Design

Naglu clone SP3-10D was scaled up for protein purification in shake flasks using CD-GLD-02 media. A 5 L working volume was seeded at 730,000 viable cells/mL and perfused at 5 L/day for a total of 4 days at 37° C. in growth phase. A transition phase of 24 hours was used to allow incorporation of the CD-GLD-02 media supplemented with 2 mg/L kifunensine at 33° C. Kifunensine is a potent inhibitor of alpha-mannosidase I. alpha-Mannosidase I catalyzes the removal of terminal, non-reducing alpha-D-mannose from high mannose glycan, which precede the formation of complex glycans. Proteins produced in cells treated with Kifunensine exhibit reduced content of complex N-linked oligosaccharides and increased content of $Man_9(GlcNAc)_2$ N-linked oligosaccharides. During the harvest phase a total of 44 L was harvested over 8 days and was stored at 4° C. until next step. A 12× ultrafiltration was performed and a total of 3.66 L concentrated conditioned media (CM) containing Naglu-kif was stored at −20° C. until purification. Naglu-kif was purified over a Butyl-Sepharose column followed by a Q-Sepharose column. Prior to loading on Butyl column, the concentrated CM was thawed and supplemented with NaCl to raise the conductivity. The purified Naglu-kif protein was concentrated and buffer exchanged into storage buffer. After the final dialysis step, the protein was sterile filtered and stored in −80° C.

3.2. Materials

Strain: Naglu_SP3-10D
Media: CD-GLD-02 (Gibco/Invitrogen, Carlsbad, Calif.)
Materials:
Bottle Top Filter 0.22 μm PES, Corning Cat #431098
Bradford Protein Assay Reagent Kit A, Pierce Cat. #2322323200
GE Healthcare AKTA Pilot chromatography station
GE Healthcare Butyl Sepharose 4 Fast Flow resin
GE Healthcare AxiChrom 70×300 Column
GelCode Blue Stain Reagent, Pierce Cat. #24592
Invitrogen 8-16% Tris-Glycine Polyacrylamide Gels, Invitrogen Cat # EC6045.
Molecular Devices SPECTRAmax PLUS 384 Microplate Spectrophotometer
Pall Membrane: 0.5 m² PALL Centrasette II cassette 30K (Chisholm Corp/Pall Cat#OS030F06)
PBS, 10× without Calcium Chloride and Magnesium Chloride, Fisher Cat. # BP 399-1
Pellicon 2"Mini" Filter, Millipore Cat #P2B030 Å 01
Spectra/Por Membrane MWCO: 12-14,000, Spectrum Laboratories Inc. Cat. #132678
Vivaspin 20 Concentrator (MWCO 10,000), Vivascience Inc Cat # VS2012
Butyl Equilibration Buffer: 20 mM Tris, 1 M Sodium Chloride, pH 7.5
Butyl Elution Buffer: 20 mM Tris, pH 7.5
Butyl Sanitization Buffer: 1 M NaOH
Butyl Storage Buffer: 20% ethanol
Q Equilibration Buffer: 20 mM Tris, pH 7.5
Q Elution Buffer: 20 mM Tris, 1M Sodium Chloride, pH 7.5
Q Sanitization Buffer: 1M NaOH
Q Storage Buffer: 20% ethanol
Storage Buffer: 1×PBS (137 mM NaCl, 2.7 mM KCl, and 11.9 mM Phosphate)
Reaction Buffer for Activity Assay: 0.1 M Sodium Acetate, 0.5 mg/ml BSA, pH4.5
Stop Buffer for Activity Assay: 0.2 M Glycine, pH 10.7
6× Sample Buffer: 1.0 mL 0.5 M Tris-HCl, pH 6.8, 0.8 mL Glycerol, 1.6 mL 10% SDS and 0.2 mL 0.5% Bromophenol Blue
Running Buffer: Tris Base, sodium dodecyl sulfate (SDS), glycine
Novex Transfer Buffer: Tris Base, glycine, methanol, SDS
ECl Wash Buffer: 20 mM Tris, 0.15 M NaCl, 0.05% Tween 20

3.3. Research Methods

HT1080 cells expressing human recombinant Naglu, clone Naglu_SP3-10D, were cultured in bioreactor with medium containing 2 mg/L kifunensine. The harvested CM was filtered, concentrated 12-fold to 3.2 L and stored in −20° C. freezer. To purify Naglu-kif, the 3.2 L concentrated CM was left at 4° C. for overnight to thaw, and then placed in a 25° C. water bath to thaw completely. After thawing, the concentrated CM was filtered again using 0.22 μm PES bottle top filter. Then, the concentrated CM was supplemented with 1 M sodium chloride by adding 5 M sodium chloride. 5 M sodium chloride was added slowly with gentle stirring. This adjusted CM, called the Butyl load, was then loaded on a Butyl column. Protein Recovery for each purification step was monitored by a Naglu activity assay and by a Bradford protein assay. All purification procedures were performed using precaution to reduce endotoxin contamination.

3.3.1. Butyl Sepharose 4 FF Column

The maximum binding capacity of the Butyl Sepharose 4 FF was experimentally determined to be 270,000 U of Naglu Activity per 1 mL of resin. To capture all of the Naglu-kif, 300 mL Butyl Sepharose 4 FF resin was packed in a XK50 column and equilibrated with 3 column volumes (CV) of Butyl Equilibration Buffer at 25 mL/min (76 cm/h). During loading, the flow rate was reduced to 15-20 mL/min (46-61 cm/h) to meet the pressure limits of the resin. After loading, column was washed with Butyl Equilibration Buffer until UV absorbance dropped to baseline. During the elution step, the flow rate was maintained at 76 cm/hr. The elution was done by a gradient that was set from 0-100% of Butyl Elution Buffer over 10 CV and followed by 4CV of 100% of Butyl Elution Buffer. Thirty four fractions of 50 mL each were collected during the elution peak. Butyl elution fractions were analyzed using a Bradford assay, a Naglu activity assay, an SDS-PAGE Coomassie-stained gel and a Western Blot. Butyl fractions were pooled according to purity determined by the above analyses. Pooled Butyl fractions were concentrated down to 300 mL using Pellicon 2"Mini" Filter with 10,000M molecular weight cut off (MWCO) and buffer exchanged once with 1 L of Q Equilibration Buffer. Final volume was 500 mL, and it was subsequently loaded on Q-Sepharose HP column.

3.3.2. Q-Sepharose HP Column

The 500 ml sample, Q load, from the previous step was divided to two 250 ml, and loaded on 75 ml of Q Sepharose HP column separately. The following paragraph describes one of the Q Sepharose HP column run. 75 mL Q Sepharose HP resin was packed in a XK26 column, charged with Q Elution Buffer and equilibrated with Q Equilibration Buffer. Loading was done at 10 mL/min (113 cm/h). After loading, the column was washed with Q Equilibration Buffer until the UV absorbance dropped to baseline. The elution gradient was set at 0-100% B over 10CV, where B represents Q Elution Buffer. Seven ½CV (37.5 mL) elution fractions were collected during the elution peak. The elution peak subsided at around 25% B. At this point, the gradient was switched to 100% B and maintained at 100% B. A peak appeared at 100% B, and the fractions collected during this peak were designated as the Strip fractions. The column was re-equilibrated for the second run. Q elution fractions were analyzed using a Bradford assay, a Naglu Activity assay, an SDS-PAGE Coomassie-stained gel and a Western Blot. Q fractions were pooled according to purity determined by the above analyses.

3.3.3. Buffer Exchange and Storage of Naglu

Pooled Q fractions, 150 mL, were concentrated down to 63 mL using six Vivaspin 20 concentrators with 10,000M MWCO. During the concentrating procedure, protein precipitation was observed. The precipitate was removed by centrifugation. To prevent further protein precipitation, 35 mL of filtrate was added back to the un-precipitated concentrated protein. The concentrated protein was dialyzed with three changes of PBS at 2 L each. More protein precipitation was observed during dialysis, and the precipitated protein was removed during sterile filtering. Purified Naglu-kif was sterile-filtered in a biosafety cabinet, aliquoted into siliconized tubes and stored at −80° C. The protein was designated Naglu-kif R3 (Research batch #3).

3.3.4. SDS-PAGE for Gelcode Blue Stain

All protein samples for gel analysis were prepared in micro-centrifuge tubes. The loading volume of the samples varied depending on the well size of the Invitrogen SDS-PAGE gels used. For the molecular weight standard, 4 μL of Precision Plus Marker was loaded. 2 μg of total protein was mixed with ⅙ loading volume of 6× Sample Buffer, ¹/₁₀ loading volume of 1 M DTT and then brought to the final volume with PBS. The mixture was boiled for 5 minutes, spun briefly, and loaded immediately on the gel. SDS-PAGE gels were run at 170-200 volts for 1 hour. Gel staining was done following the manufacturer's instructions for Gelcode Blue Staining Kit.

3.3.5. Bradford Protein Assay

Dilutions of protein samples were made in PBS in a reaction plate. 250 μL Coomassie (Bradford) Protein Reagent was added to 5 μL of the diluted protein samples on the reaction plate. After ten-minute incubation at room temperature, the absorbance at 595 nm was measured. Samples were compared to a standard curve of bovine serum albumin. Bradford protein assay only detects proteins larger than 3,000 Da.

3.3.6. Activity Assay

The specific substrate for Naglu, 4-methylumbelliferyl-N-acetyl-α-D-glucosaminide, had very low solubility in water and required DMSO to be dissolved in solution. A 10 mM stock of substrate was prepared by dissolving 5 mg of 4-methylumbelliferyl-N-acetyl-α-D-glucosaminide in 250 μL of 100% DMSO first. Naglu activity assay reaction buffer was then added to bring the volume up to 1318 μL. This 10 mM Substrate stock was further diluted 10-fold with reaction buffer to make the 1 mM substrate solution. Un-used 10 mM substrate stock was stored in −80° C. for up to one month. Samples and controls were pre-diluted in reaction buffer. 10 μL of each pre-diluted sample/control was applied in duplicate wells on a black clear bottom 96 well plate. 10 μL of reaction buffer was added to two wells of the plate and served as reaction buffer control. 75 μL of 1 mM substrate was added to each well that contained 10 μL of sample/control. The plate was sealed with plate sealer and wrapped with aluminum foil. The plate was placed in 37° C. Jitterbug and incubated with shaking setting at #1 for 1 hour. Prior to the completion of incubation, standards were prepared by diluting the stock (1000 μM) of 4-methlyumbelliferyl sodium salt down to 25 μM, 12.5 μM, 6.25 μM, 3.12 μM, 1.56 μM, 0.78 μM, 0 μM with water. At the completion of incubation, 85 μL of each of the seven standards was loaded on the plate in duplicate. 200 μL of Stop Buffer was added to all of the wells containing sample, control or standard. The plate was measured for fluorescence at 360/460 (Excitation/Emission) using a Molecular Devices SpectraMax Plus M2 plate reader. Using the Softmax program, enzymatic activity of the Naglu-kif was extrapolated from the fluorescence data of the standards and the samples.

3.4. NAGLU Purification and Analysis

Figure 5:
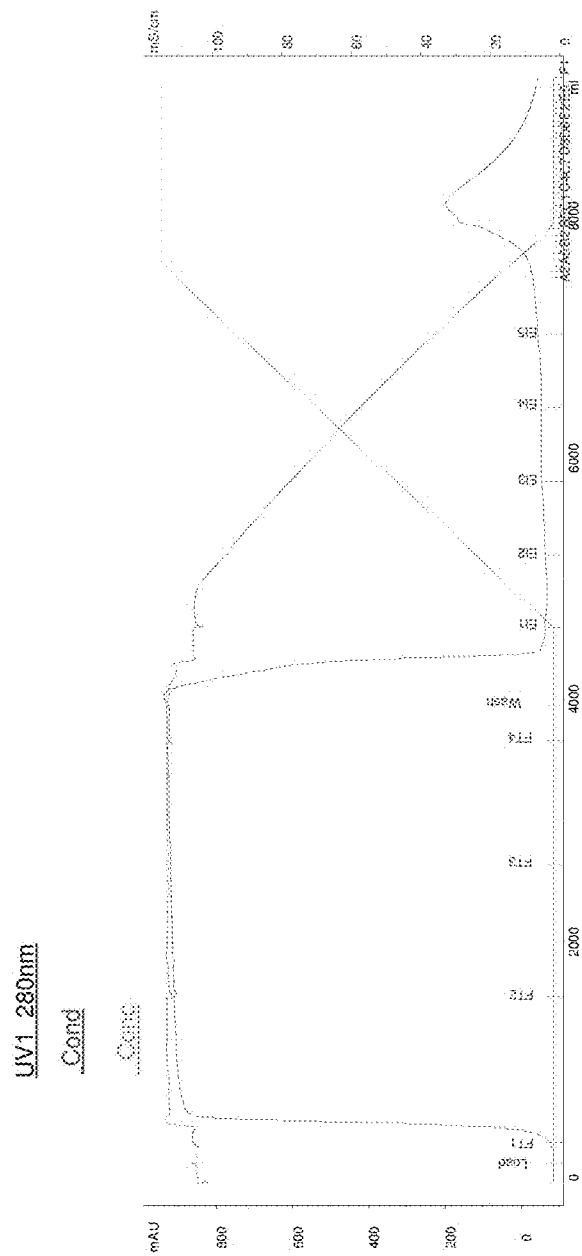
FIG. 5 shows a chromatogram of the Butyl Sepharose 4 FF column used for NAGLU purification from conditioned media.
Figure 6:
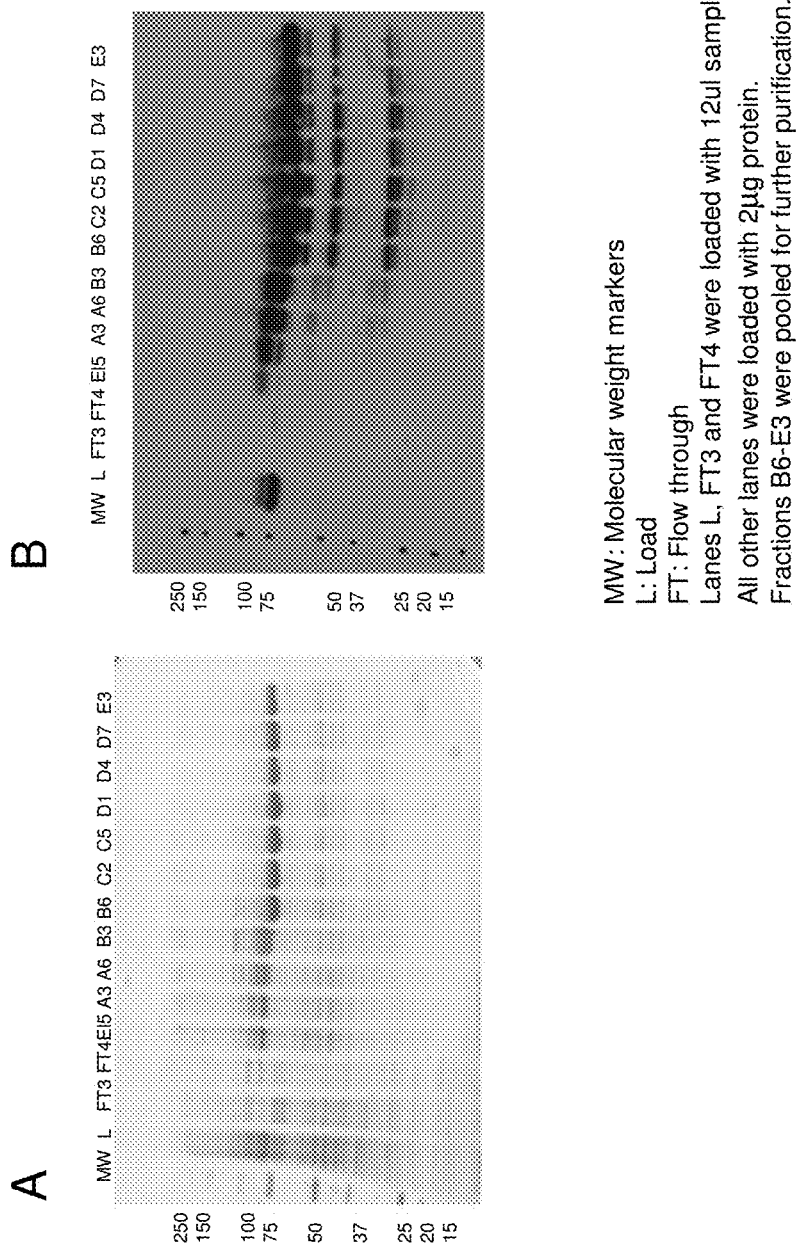
FIG. 6 shows images of SDS-PAGE (A) and Western Blot (B) for the Butyl Sepharose 4 FF column fractions.
Figure 7:
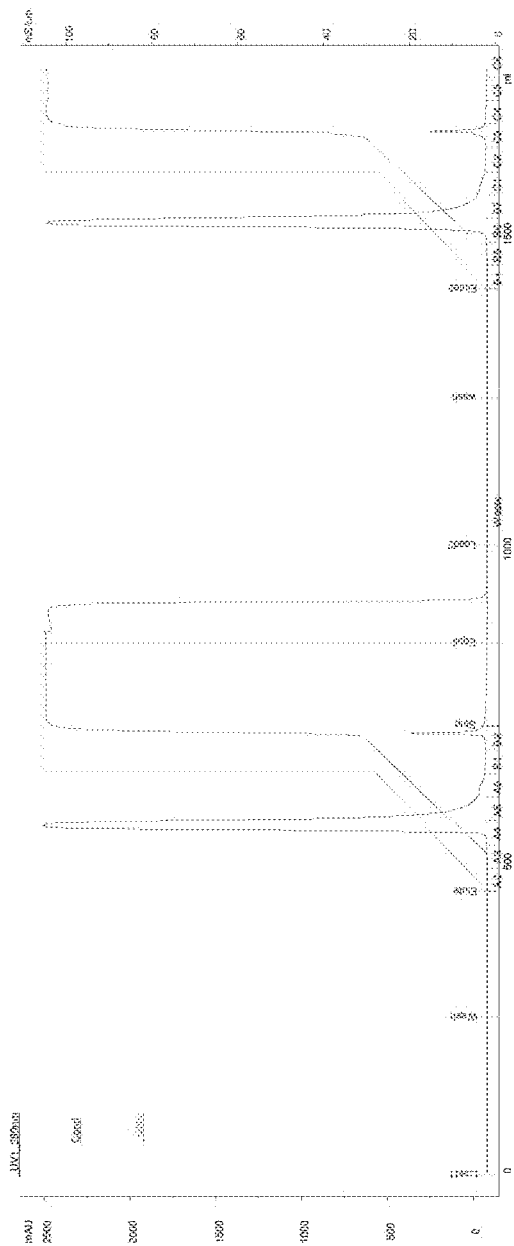
FIG. 7 shows a chromatogram of the Q Sepharose HP column.
Figure 8:
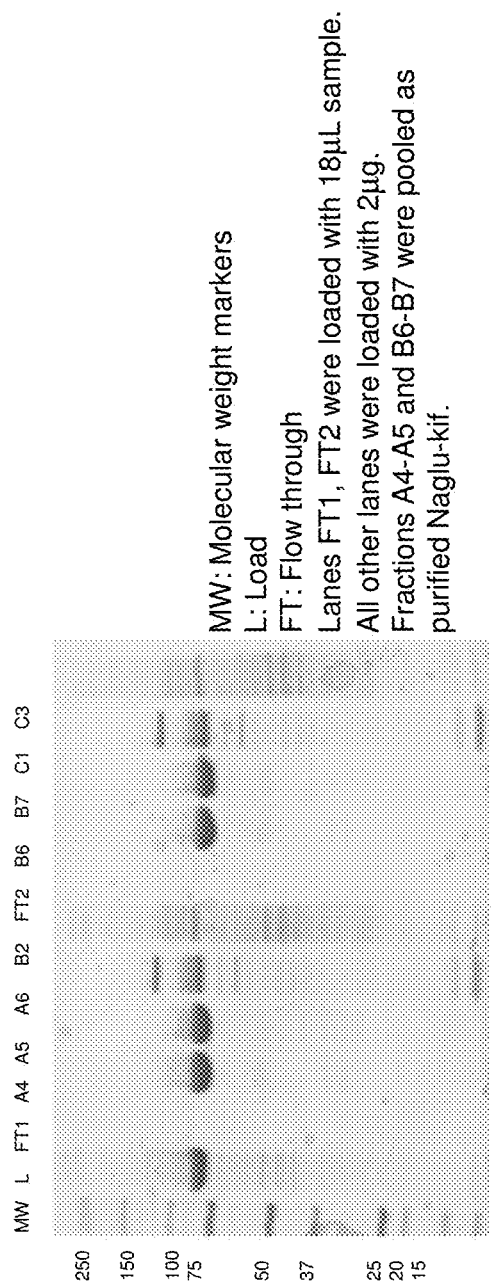
FIG. 8 depicts an image of SDS-PAGE elution profile for the Q Sepharose HP column.

Naglu kif protein was purified in batch from 3.2 L of media produced in the presence of kifunensine. 3.2 L of 12× concentrated conditioned media were thawed overnight at 4° C. followed by brief incubation at 25° C. Thawed media was filtered through 0.22 μm PES bottle top filter. Sodium Chloride Stock Buffer (5 M) was added with gentle stirring to adjust Sodium Chloride concentration. The adjusted conditioned media was loaded on 300 mL XK50 Butyl Sepharose 4 FF Column at 46-61 cm/h. Wash and elution steps were done at 76 cm/h. 34 fractions were collected along the elution peak. FIG. 5 shows the Chromatogram of the Butyl FF column. SDS-PAGE elution profile and Western Blot for the Butyl column run is shown in FIG. 6. Fractions B6-E3 were combined as Butyl pool. It was concentrated to 300 mL and buffer exchanged in Q Equilibration Buffer once, using 1000 mL of the Equilibration Buffer. The final 50 0 mL of buffer exchanged Butyl pool were split into 2 runs over 75 mL Q Sepharose HP Column. The elution gradient for the Q column was set over 10CV from 0-100% B. ½ CV elution fractions were collected during the elution peak. Once the gradient reached 25% it was switched to 100% of Q Elution Buffer and column was stripped with 2CV of Q Elution Buffer. The column was re-equilibrated and repeated with the second half of the Q-load. FIG. 7 shows the chromatogram of the Q HP column. SDS-PAGE elution profile for the Q column run is shown in FIG. 8. The Q pool was concentrated, buffer exchanged into Storage Buffer. Some protein precipitation was observed during concentration and dialysis step. Protein solution was filter sterilized using 0.22 μm PES bottle top filter. The final purified protein, Naglu-kif, was aliquoted for storage at −80° C. 94 mg of purified Naglu-kif was obtained in this run. Total protein recovery for each purification step is summarized in Table 6.

TABLE 6

Summary for Purification of Naglu-kif

| | Volume (mL) | Bradford (mg/mL) | Activity nmol/h | Recovery % |
|---|---|---|---|---|
| Butyl Load | 4000 | n/a | 9.6 10$^7$ | 100 |
| Butyl Pool | 1000 | 0.28 | 6.3 10$^7$ | 65 |
| Q-Load | 475 | 0.51 | 5.5 10$^7$ | 57 |
| Q-Pool | 150 | 1.1 | 5.1 10$^7$ | 53 |
| Naglu kif R3 | 85.4 | 1.1 | 2.8 10$^7$ | 29 |

3.5. Summary

For Naglu kif purification, a two-step process was used. This process included a Butyl Sepharose step and a Q-Sepharose step. After Butyl column protein pool was concentrated and buffer exchanged to the Q-Equilibration Buffer using an ultrafiltration/diafiltration (UF/DF) system. Since protein was eluted from the Butyl column late in a gradient, one cycle of buffer exchange was sufficient to lower conductivity. During concentration of the Q column pool, protein precipitation was observed when the protein concentration reached 2 mg/mL. The precipitate was removed by centrifugation for 10 min at 3,000 g. To prevent further precipitation, protein was diluted with filtrate to 1 mg/mL.

Figure 9:
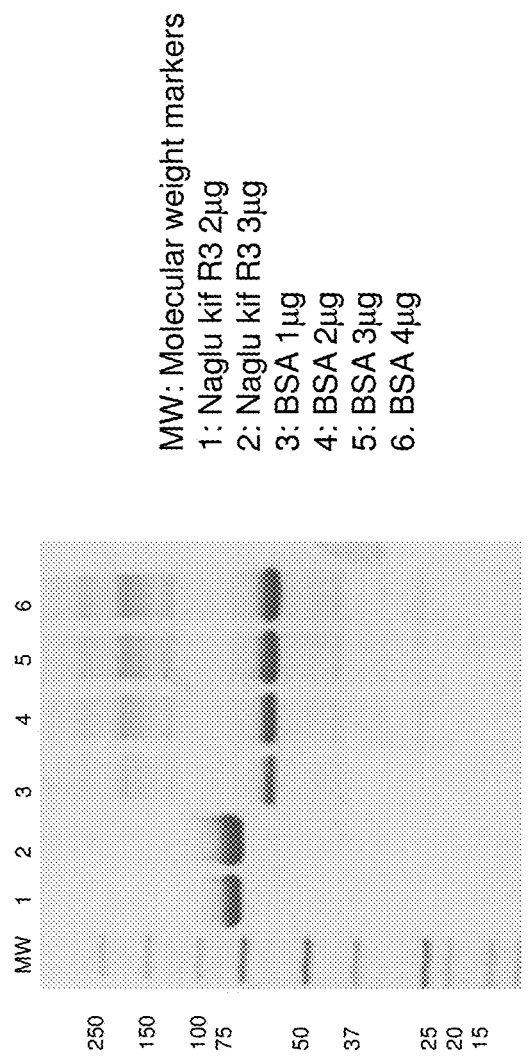
FIG. 9 depicts an image of an SDS-PAGE gel of purified NAGLU-kif.

During dialysis into Storage buffer, additional minor precipitation was observed. The final concentration of Naglu-kif was 1.1 mg/mL by a Bradford Protein Assay and the total amount obtained was 94 mg of final product (FIG. 9).

Example 4

Naglu Mutations Mapped in the 2.9 Å Crystal Structure of NAGLU-Kif 4.1. Overall Structure The final model of NAGLU obtained from the 2.9 Å crystal structure contained all the amino acids, from amino acid 24-743, including six glycans at positions N261, N272, N435, N503, N526 and N532. NAGLU has three domains (I, II, III). Domain I is a small α/β domain (amino acids 24-126). Domain II is a (α/β)$_8$ barrel domain (amino acids 127-467) containing the catalytic residues E316 and E446. In certain embodiments, NAGLU exhibits a crystallographic symmetry of a trimeric arrangement formed by the interaction of domain II, as illustrated in FIG. 4. Domain III is an all α-helical bundle domain (amino acids 468-743). The three domain structure is illustrated in FIG. 3; amino acid residues are numbered according to SEQ ID NO: 3, amino acids 24-743).

4.2. Mapping of Pathogenic Mutations

Many naglu mutations have been identified that affect NAGLU enzymatic activity. For example, Yogalingam et al. (2001) *Hum. Mutat.* 18:264-281 have identified 24 unique mutations (excluding deletion, insertion and premature stop codons/termination mutations), summarized in Table 7:

TABLE 7

Severe mutations in naglu identified by Yogalingam et al.

| | 1$^{st}$ Allele | 2$^{nd}$ Allele |
|---|---|---|
| 1 | L35F | G292R |
| 2 | F48C | F48C |
| 3 | Y140C | R626X |
|   | Y140C | R674C |
| 4 | W156C | Y140C |
| 5 | R234C | R234C |
| 6 | W268R | W268R |
| 7 | G292R | R565W |
| 8 | V334F | V334F |
| 9 | F410S | N.I* |
| 10 | H414R | 503-512 del |
| 11 | Y455C | P521L |
| 12 | V501G | V501G |
| 13 | R520W | N.I |
| 14 | P521L | Y455C |
|    | P521L | P521L |
| 15 | R565W | G292R |
|    | R565P | 1035del2 |
| 16 | L591P | R297X |
| 17 | L617F | N.I |
| 18 | W649C | W649C |
| 19 | G650E | R674C |
| 20 | R674C | Y140C |
|    | R674C | R674H |
|    | R674H | R674 |
| 21 | R676P | R297X |
| 22 | E705K | R297X |

N.I—not identified

FIG. 10 depicts stick-and-ribbon representations of naglu mutations modeled into the structure obtained at 2.9 Å. The green sticks represent glycans and the red sticks represent severe naglu mutations. In total 24 unique mutations (excluding deletion, insertion and premature stop codons/termination mutations) were mapped. Clusters of pathogenic mutations can be identified in the crystal structure (FIG. 16). There are at least five severe mutations near the active site, within 5 Å from the modeled product (N-Acetylglucosamine) in the active site, that include Y140C, W268R, F410S, W649C and G650E (FIG. 11). Another cluster of six severe mutations is seen near a loop (amino acid 502-533) containing three glycosylation sites (N503, N526 and N532). This cluster includes R520W, P521L, R674C or R674H, R676P, E705K and Q706X (FIG. 12). A third cluster of mutation can be identified at the interface of domains I, II and III, which includes H100R, E153K, W156C, E452K, Y455C and R482W (FIGS. 15 and 17). FIG. 16 summarizes the identified clusters of mutations, where green sticks represent glycans; red sticks represent severe naglu mutations; blue sticks represent N.R mutations (not reported—insufficient data, the expression of these mutations and additional cases may be required to assign clinical phenotype to these alleles (Yogalingam et al. *Hum. Mutat.* 2001), summarized in Table 8); and yellow sticks represent attenuated naglu mutations (summarized in Table 9).

TABLE 8

N.R Mutations

| | 1$^{st}$ allele | 2nd allele |
|---|---|---|
| 1 | G79C | G79C |
| 2 | G82D | G82D |
| 3 | Y92H | Y140C |
| 4 | H100R | H100R |
| 5 | P115S | P115S |
| 6 | E153K | E153K |
| 7 | C277F | M1L |
| 8 | L280 | N.I |
| 9 | G292R | G292R |
| 10 | P358L | P358L |
| 11 | E452K | E452K |
| 12 | Y455C | R674H |
| 13 | Y455C | R482W |
| 14 | L561R | L561R |
| 15 | R565Q | term at 132 |
| 16 | R565Q | inframe duplication of aa 72-75 |
| 17 | R643H | R297X |
| 18 | A664V | R203X |
| 19 | R674H | R674H |
| 20 | R674H | Y455C |
| 21 | L682R | Y140C |

TABLE 9

Attenuated mutations

| | 1st allele | 2nd allele |
|---|---|---|
| 1 | F48L | R297X |
| 2 | G69S | R297X |
| 3 | 8aa insert at 233 | S612G |
| 4 | H227P | P521L |
| 5 | H248R | N.I |
| 6 | S534Y | N.I |
| 7 | L560P | N.I |
| 8 | S612G | 233-234 ins24 |
| 9 | R643C | R643C |

In total about 44 unique mutations (excluding cases in which both alleles have insertion, deletion or premature stop/termination codon mutations) were mapped with nine incidences of an amino acid mutated to cystein and with eight occurrences of an arginine mutated either another amino acid or to a stop codon.

Example 5

Crystal Structure of rhNAGLU

Figure 18:
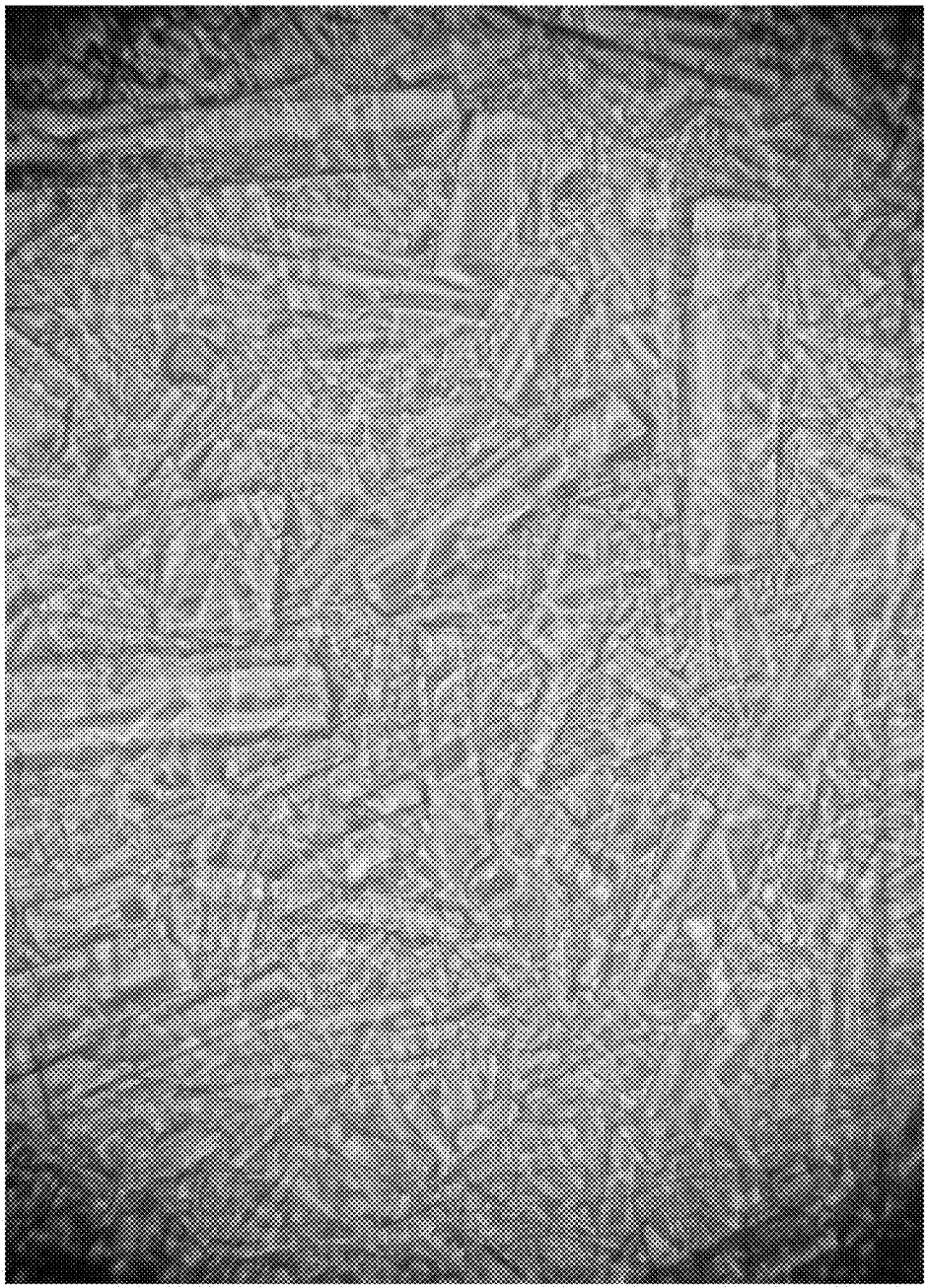
FIG. 18 is a photograph of crystals of recombinant human NAGLU (rhNAGLU).
Figure 19:
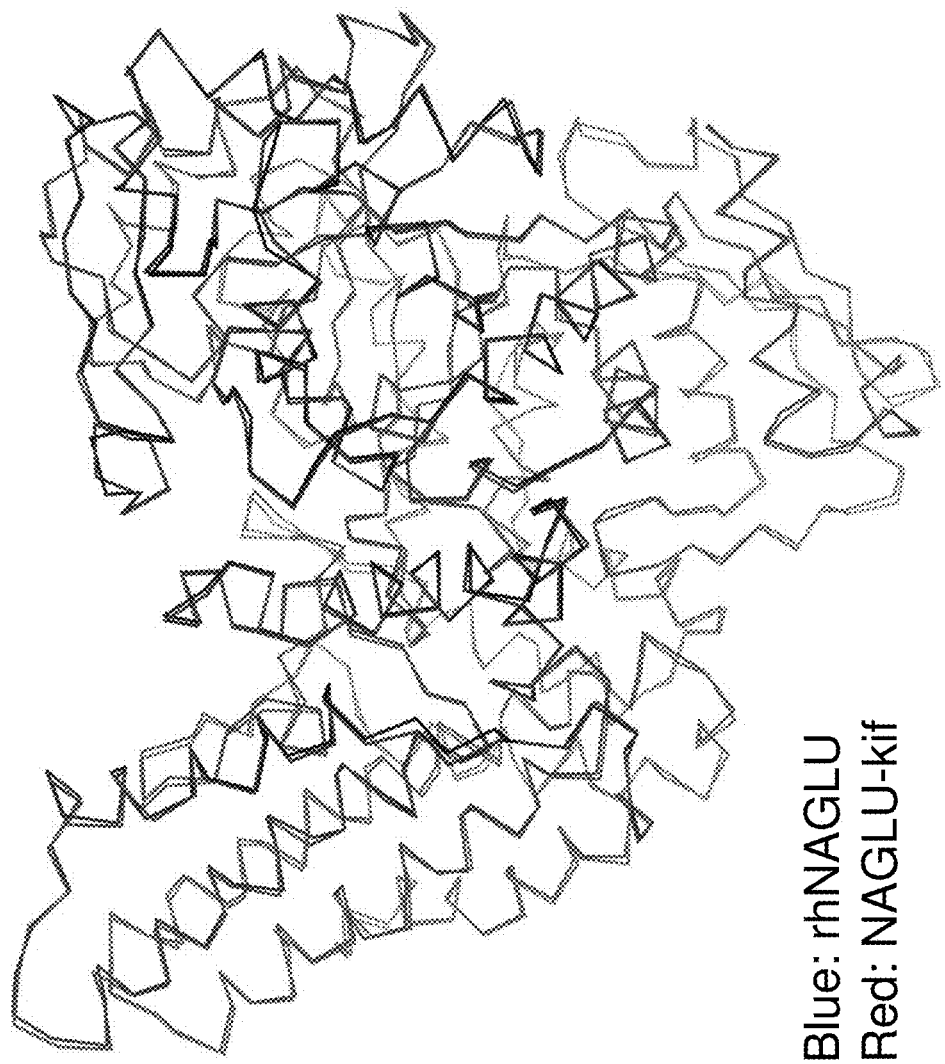
FIG. 19 depicts the structure of rhNAGLU (3.5 Å resolution) superimposed on the structure of NAGLU-kif (2.4 Å resolution). Backbone structures are shown in ribbon representation.

Recombinant human NAGLU (rhNAGLU) in phosphate buffered saline (PBS) was concentrated to 16.5 mg/ml. Concentrated rhNAGLU was stored at 4° C., and crystalline material was observed at the bottom of the vial after about two months (FIG. 18). A suitable single crystal from this crystalline material was transferred into PBS containing 20% glycerol and 20% xylitol as cryoprotectants. The crystal was flash frozen in a liquid nitrogen stream, and diffraction data was collected using a rotating anode X-ray diffractometer. The rhNAGLU crystal diffracted to about 3.2 Å resolution and belongs to the same space group and unit cell dimensions as NAGLU-Kif. A data set of 90 frames was collected with 30 minute exposure per frame and an oscillation of one degree. Diffraction data was processed in P63 space group to a resolution of 3.5 Å and a completeness of 97%. Structure was solved using CCP4 suite using NAGLU-kif structure as molecular replacement model. The structure of rhNAGLU was refined to a final R and $R_{free}$ of 20.2% and 25.6%, respectively, by iterative model building in Coot and refinement in Refmac5. The structures of rhNAGLU and NAGLU-kif are similar and could be superimposed, with a root mean square (RMS) deviation of 0.297 Å for the backbone atoms (FIG. 19).

EQUIVALENTS AND SCOPE

Those skilled in the art will recognize or be able to ascertain using no more than routine experimentation many equivalents to the specific embodiments described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

APPENDIX

Table 3 Naglu Crystal Structure Data at 2.9 Å (Naglu-Kif, Table 3.1), 2.4 Å (Naglu-Kif, Table 3.2), and 3.49 Å (Rh-Naglu, Table 3.3):
Lengthy Table The patent application contains a lengthy table section. A copy of Table 3 was submitted in electronic form to the U.S. Patent and Trade mark Office (USPTO) concurrently with the filing of this application. A copy of Table 3 is available in electronic form from the USPTO website. An electronic copy of the Table 3 is also available from the USPTO upon request and payment of the fee set forth in 37 C.F.R. §1.19(b)(3).

Table 3 was submitted as an ASCII text file named "Table3.txt" (2401 kilobytes) to the USPTO on a compact disc (CD) created on Jul. 22, 2011, and labeled "TABLE 3" concurrently with the filing of this application. The entire contents of the materials on the CD submitted to the USPTO, including the entire contents of the Table3.txt text file, are incorporated herein by reference.

TABLE 4

NAGLU MUTATIONS

| Mutation | Sequence alteration |
| --- | --- |
| c54g | GCC => GCG |
| F48L | TTC => TTA |
| G69S | GGC => AGC |
| H227P | CAC => CCC |
| H248R | CAT => CGT |
| G292R | GGG => AGG |

TABLE 4-continued

NAGLU MUTATIONS

| | |
|---|---|
| R297X/A(8%)/D(23%) | CGA => TGA |
| V334F | GTC => TTC |
| W404X | TGG => TAG |
| F410S | TTT => TCT |
| H414R | CAT => CGT |
| W494X | TGG => TGA |
| P521L/A(6%) | CCG => CTG |
| L560P | CTG => CCG |
| R565P | CGG => CCG |
| R565W/A(6%) | CGG => TGG |
| L617F | TTG => TTC |
| R626X/A (6%) | CGA => TGA |
| R643C/D (19%) | CGC => TGC |
| G650E | GGG => GAG |
| R674C | CGC => TGC |
| R676P | CGG => CCG |
| G737R/A(4%)/D(4%) | GGC => CGC |
| delG59 | GGGGGCG => GGGG_CG |
| del10bp503b | del[GGAGCGGCCA] |
| delTG1035 | GCTGTGTG => GCTG_TG |
| delA1317 | GGTAG => GG_TG |
| delA2100 | CAAAAAT => CAAAA_T |
| del2bp2171 | ACTGTGGA => ACTG_GA |
| ins25bp48 | [GGGGC ... CGACG]duplicated |
| ins7bp48 | [GGGGCCG] duplicated |
| ins5bp209 | [GCGGC] duplicated |
| insAA950 | GATGC => GATAAGCA |

(Weber et al. (1999) *Eur. J. Hum. Gen.* 7: 34-44, reference incorporated herein in its entirety, particularly Tables 3 and 4).

Mutations of NAGLU that were identified in MPS III-B patients in Turkey:

L682R
E153K
g.17703 A > G
T437I
(Serap et al. (2002) *Human Mutation* 19: 184-85).

Mutations of NAGLU that were identified in nine fibroblast cell lines derived from Sanfilippo syndrome type B patients:

503del110
901delAA
652insC
R203X
R297X
R626X
Q706X
Y92H
P115S
Y140C
E153K
P358L
S612G
A664V
R674H
L682R
(Schmidtchen et al. (1998) *Am J Hum Genet* 62: 64-69)

Mutations of NAGLU that were identified in 18 Sanfilippo B families:

R38W
V77G
407-410del4
703delT
A246P
Y335C
1487delT
E639X
(Beesley et al. (2005) *J. Inher. Metab. Dis.* 28: 759-767).

Mutations of NAGLU that were identified in 14 MPS III-B patients:

219-237del19
334-358del25
1335delC
2099delA
1447-1448insT
1932-1933insGCTAC
R297X
R626X
F48C
Y140C
R234C
W268R
P521L
R565W
L591P
E705K
(Beesley et al. (1998) *J. Med. Genet.* 35: 910-914).

Mutations of NAGLU that were identified in seven Japanese patients from six unrelated families with mucopolysaccharidosis III-B (Sanfilippo type B):

V241M
F314L
R482W
R565W
R565P
delTG2171-2172 (exon 6)
(Tanaka et al. (2002) *J Hum Genet* 47: 484-487)

Mutations of NAGLU that were identified in 20 Italian Sanfilippo type B patients:

L35F
204delC
221insGCGCG
G82D, W156C
507delC, IVS3 + 1G-->A
E336X
V501G
R520W
S534Y
W649C
1953insGCCA
2185delAGA
(Tessitore et al. (2000) *Hum Genet* 107: 568-576)

Mutations of NAGLU that were identified in skin fibroblasts of 22 MPS III-B patients (European Human Cell Bank, Rotterdam and University Children's Hospital, Mainz):

| | |
|---|---|
| M1L | ATG=>TTG |
| 274ins4 | dupl 271-274 |
| 338ins24 | dupl 315-338 |
| G79C | GGC => TGC |
| R100H | CAC => CGC |
| Y140C | TAC => TGC |
| F142del | TTC => — |
| pol: IVS2 + 50G => C | G => C |
| R203X | CGA => TGA |
| P243L | CCT => CTT |
| C277F | TGC => TTC |
| L280P | CTT => CCT |
| G292R | GGG => AGG |
| R297X | CGA => TGA |
| 1006delAG | GAG => G— |
| W404X | TGG => TAG |
| E452L | GAA => AAA |
| R482W | CGG => TGG |
| L561R | CTG => CGG |
| R565Q | CGG => CAG |
| R674H | CGC => CAC |

TABLE 4-continued

NAGLU MUTATIONS

| | |
|---|---|
| E705L | GAG => AAG |
| pol: G737R | GGC => CGC |

(Bunge et al. (1999) *J Med Genet* 36: 28-31, reference incorporated herein in its entirety, particularly Table 2).

| | 1st Allele | 2nd Allele |
|---|---|---|
| 1 | L35F | G292R |
| 2 | F48C | F48C |
| 3 | Y140C | R626X |
|   | Y140C | R674C |
| 4 | W156C | Y140C |
| 5 | R234C | R234C |
| 6 | W268R | W268R |
| 7 | G292R | R565W |
| 8 | V334F | V334F |
| 9 | F410S | N.I |
| 10 | H414R | 503-512 |
| 11 | Y455C | P521L |
| 12 | V501G | V501G |
| 13 | R520W | N.I* |
| 14 | P521L | Y455C |
|    | P521L | P521L |
| 15 | R565W | G292R |
|    | R565P | 1035del2 |
| 16 | L591P | R297X |
| 17 | L617F | N.I |
| 18 | W649C | W649C |
| 19 | G650E | R674C |
| 20 | R674C | Y140C |
|    | R674C | R674H |
|    | R674H | R674 |
| 21 | R676P | R297X |
| 22 | E705K | R297X |

Yogalingam et al. (2001) *Hum Mutat* 18: 264-281:
*N.I - not identified

TABLE 5

NAGLU ACTIVE SITE COORDINATES

Table 5.1 at 2.9 Å

N134

| | | | | | | | | | | |
|---|---|---|---|---|---|---|---|---|---|---|
| ATOM | 1632 | N | ASN | A | 134 | 91.279 | -31.010 | 2.042 | 1.00 | 29.38 | N |
| ATOM | 1633 | CA | ASN | A | 134 | 90.106 | -31.221 | 1.213 | 1.00 | 30.21 | C |
| ATOM | 1635 | CB | ASN | A | 134 | 89.635 | -29.874 | 0.605 | 1.00 | 31.44 | C |
| ATOM | 1638 | CG | ASN | A | 134 | 88.254 | -29.944 | -0.102 | 1.00 | 32.75 | C |
| ATOM | 1639 | OD1 | ASN | A | 134 | 88.043 | -30.763 | -1.026 | 1.00 | 35.54 | O |
| ATOM | 1640 | ND2 | ASN | A | 134 | 87.351 | -29.024 | 0.270 | 1.00 | 30.49 | N |
| ATOM | 1643 | C | ASN | A | 134 | 90.594 | -32.172 | 0.149 | 1.00 | 29.54 | C |
| ATOM | 1644 | O | ASN | A | 134 | 91.778 | -32.115 | -0.245 | 1.00 | 30.12 | O |

C136

| | | | | | | | | | | |
|---|---|---|---|---|---|---|---|---|---|---|
| ATOM | 1662 | N | CYS | A | 136 | 90.059 | -31.921 | -2.758 | 1.00 | 29.02 | N |
| ATOM | 1663 | CA | CYS | A | 136 | 90.569 | -31.011 | -3.804 | 1.00 | 29.75 | C |
| ATOM | 1665 | CB | CYS | A | 136 | 89.703 | -29.782 | -3.942 | 1.00 | 30.72 | C |
| ATOM | 1668 | SG | CYS | A | 136 | 88.080 | -30.254 | -4.212 | 1.00 | 36.73 | S |
| ATOM | 1670 | C | CYS | A | 136 | 91.987 | -30.540 | -3.599 | 1.00 | 28.10 | C |
| ATOM | 1671 | O | CYS | A | 136 | 92.670 | -30.287 | -4.572 | 1.00 | 28.48 | O |

Y140

| | | | | | | | | | | |
|---|---|---|---|---|---|---|---|---|---|---|
| ATOM | 1715 | N | TYR | A | 140 | 94.837 | -29.168 | -6.221 | 1.00 | 25.53 | N |
| ATOM | 1716 | CA | TYR | A | 140 | 95.069 | -27.742 | -6.428 | 1.00 | 25.43 | C |
| ATOM | 1718 | CB | TYR | A | 140 | 93.936 | -26.875 | -5.853 | 1.00 | 25.19 | C |
| ATOM | 1721 | CG | TYR | A | 140 | 92.610 | -26.849 | -6.650 | 1.00 | 25.27 | C |
| ATOM | 1722 | CD1 | TYR | A | 140 | 92.594 | -26.665 | -8.005 | 1.00 | 24.48 | C |
| ATOM | 1724 | CE1 | TYR | A | 140 | 91.374 | -26.586 | -8.706 | 1.00 | 25.13 | C |
| ATOM | 1726 | CZ | TYR | A | 140 | 90.197 | -26.685 | -8.066 | 1.00 | 25.21 | C |
| ATOM | 1727 | OH | TYR | A | 140 | 89.092 | -26.631 | -8.819 | 1.00 | 26.19 | O |
| ATOM | 1729 | CE2 | TYR | A | 140 | 90.158 | -26.872 | -6.734 | 1.00 | 24.77 | C |
| ATOM | 1731 | CD2 | TYR | A | 140 | 91.349 | -26.945 | -6.016 | 1.00 | 25.20 | C |
| ATOM | 1733 | C | TYR | A | 140 | 96.394 | -27.338 | -5.844 | 1.00 | 24.50 | C |
| ATOM | 1734 | O | TYR | A | 140 | 96.970 | -26.412 | -6.314 | 1.00 | 25.79 | O |

W201

| | | | | | | | | | | |
|---|---|---|---|---|---|---|---|---|---|---|
| ATOM | 2709 | N | TRP | A | 201 | 88.777 | -34.971 | -9.052 | 1.00 | 29.80 | N |
| ATOM | 2710 | CA | TRP | A | 201 | 87.444 | -35.097 | -9.624 | 1.00 | 30.40 | C |
| ATOM | 2712 | CB | TRP | A | 201 | 87.157 | -33.862 | -10.533 | 1.00 | 30.83 | C |
| ATOM | 2715 | CG | TRP | A | 201 | 87.286 | -32.664 | -9.658 | 1.00 | 29.28 | C |
| ATOM | 2716 | CD1 | TRP | A | 201 | 86.351 | -32.203 | -8.794 | 1.00 | 27.58 | C |
| ATOM | 2718 | NE1 | TRP | A | 201 | 86.848 | -31.178 | -8.049 | 1.00 | 26.88 | N |
| ATOM | 2720 | CE2 | TRP | A | 201 | 88.162 | -30.981 | -8.386 | 1.00 | 27.22 | C |
| ATOM | 2721 | CD2 | TRP | A | 201 | 88.476 | -31.911 | -9.395 | 1.00 | 28.34 | C |
| ATOM | 2722 | CE3 | TRP | A | 201 | 89.768 | -31.920 | -9.922 | 1.00 | 27.20 | C |
| ATOM | 2724 | CZ3 | TRP | A | 201 | 90.685 | -30.983 | -9.444 | 1.00 | 26.68 | C |
| ATOM | 2726 | CH2 | TRP | A | 201 | 90.339 | -30.078 | -8.447 | 1.00 | 25.18 | C |
| ATOM | 2728 | CZ2 | TRP | A | 201 | 89.085 | -30.051 | -7.913 | 1.00 | 25.64 | C |
| ATOM | 2730 | C | TRP | A | 201 | 87.261 | -36.473 | -10.300 | 1.00 | 30.64 | C |
| ATOM | 2731 | O | TRP | A | 201 | 86.143 | -37.021 | -10.375 | 1.00 | 30.58 | O |

TABLE 5-continued

NAGLU ACTIVE SITE COORDINATES

M204

| | | | | | | | | | | | |
|---|---|---|---|---|---|---|---|---|---|---|---|
| ATOM | 2764 | N | MET | A | 204 | 86.231 | −38.750 | −7.479 | 1.00 | 28.53 | N |
| ATOM | 2765 | CA | MET | A | 204 | 84.893 | −38.676 | −6.962 | 1.00 | 29.12 | C |
| ATOM | 2767 | CB | MET | A | 204 | 84.574 | −37.271 | −6.459 | 1.00 | 29.50 | C |
| ATOM | 2770 | CG | MET | A | 204 | 85.260 | −36.947 | −5.162 | 1.00 | 28.11 | C |
| ATOM | 2773 | SD | MET | A | 204 | 84.870 | −35.338 | −4.496 | 1.00 | 27.88 | S |
| ATOM | 2774 | CE | MET | A | 204 | 85.566 | −34.241 | −5.744 | 1.00 | 29.11 | C |
| ATOM | 2778 | C | MET | A | 204 | 83.894 | −39.117 | −8.005 | 1.00 | 30.12 | C |
| ATOM | 2779 | O | MET | A | 204 | 82.684 | −39.147 | −7.728 | 1.00 | 30.66 | O |

W268

| | | | | | | | | | | | |
|---|---|---|---|---|---|---|---|---|---|---|---|
| ATOM | 3780 | N | TRP | A | 268 | 78.869 | −33.544 | −15.364 | 1.00 | 38.62 | N |
| ATOM | 3781 | CA | TRP | A | 268 | 79.345 | −32.657 | −14.299 | 1.00 | 38.58 | C |
| ATOM | 3783 | CB | TRP | A | 268 | 80.105 | −33.474 | −13.253 | 1.00 | 37.55 | C |
| ATOM | 3786 | CG | TRP | A | 268 | 80.839 | −32.688 | −12.165 | 1.00 | 37.23 | C |
| ATOM | 3787 | CD1 | TRP | A | 268 | 80.401 | −32.431 | −10.903 | 1.00 | 36.90 | C |
| ATOM | 3789 | NE1 | TRP | A | 268 | 81.360 | −31.737 | −10.205 | 1.00 | 37.00 | N |
| ATOM | 3791 | CE2 | TRP | A | 268 | 82.436 | −31.524 | −11.019 | 1.00 | 34.25 | C |
| ATOM | 3792 | CD2 | TRP | A | 268 | 82.164 | −32.131 | −12.247 | 1.00 | 36.77 | C |
| ATOM | 3793 | CE3 | TRP | A | 268 | 83.144 | −32.087 | −13.261 | 1.00 | 37.14 | C |
| ATOM | 3795 | CZ3 | TRP | A | 268 | 84.333 | −31.449 | −13.012 | 1.00 | 33.93 | C |
| ATOM | 3797 | CH2 | TRP | A | 268 | 84.554 | −30.855 | −11.772 | 1.00 | 35.09 | C |
| ATOM | 3799 | CZ2 | TRP | A | 268 | 83.610 | −30.882 | −10.767 | 1.00 | 33.39 | C |
| ATOM | 3801 | C | TRP | A | 268 | 80.299 | −31.599 | −14.885 | 1.00 | 39.35 | C |
| ATOM | 3802 | O | TRP | A | 268 | 81.011 | −31.856 | −15.869 | 1.00 | 39.25 | O |

N315

| | | | | | | | | | | | |
|---|---|---|---|---|---|---|---|---|---|---|---|
| ATOM | 4514 | N | ASN | A | 315 | 79.037 | −36.767 | −4.791 | 1.00 | 31.39 | N |
| ATOM | 4515 | CA | ASN | A | 315 | 79.546 | −35.427 | −4.572 | 1.00 | 31.75 | C |
| ATOM | 4517 | CB | ASN | A | 315 | 81.007 | −35.460 | −4.161 | 1.00 | 31.57 | C |
| ATOM | 4520 | CG | ASN | A | 315 | 81.612 | −34.074 | −3.971 | 1.00 | 33.62 | C |
| ATOM | 4521 | OD1 | ASN | A | 315 | 81.772 | −33.618 | −2.822 | 1.00 | 36.98 | O |
| ATOM | 4522 | ND2 | ASN | A | 315 | 82.007 | −33.415 | −5.090 | 1.00 | 35.35 | N |
| ATOM | 4525 | C | ASN | A | 315 | 79.366 | −34.640 | −5.858 | 1.00 | 31.77 | C |
| ATOM | 4526 | O | ASN | A | 315 | 79.868 | −34.999 | −6.929 | 1.00 | 30.07 | O |

E316

| | | | | | | | | | | | |
|---|---|---|---|---|---|---|---|---|---|---|---|
| ATOM | 4528 | N | GLU | A | 316 | 78.599 | −33.574 | −5.709 | 1.00 | 32.86 | N |
| ATOM | 4529 | CA | GLU | A | 316 | 78.208 | −32.737 | −6.803 | 1.00 | 34.10 | C |
| ATOM | 4531 | CB | GLU | A | 316 | 79.422 | −31.854 | −7.287 | 1.00 | 34.09 | C |
| ATOM | 4534 | CG | GLU | A | 316 | 79.808 | −30.713 | −6.278 | 1.00 | 34.70 | C |
| ATOM | 4537 | CD | GLU | A | 316 | 80.808 | −29.605 | −6.784 | 1.00 | 37.65 | C |
| ATOM | 4538 | OE1 | GLU | A | 316 | 81.353 | −29.633 | −7.933 | 1.00 | 37.01 | O |
| ATOM | 4539 | OE2 | GLU | A | 316 | 81.052 | −28.674 | −5.961 | 1.00 | 39.36 | O |
| ATOM | 4540 | C | GLU | A | 316 | 77.498 | −33.536 | −7.938 | 1.00 | 33.61 | C |
| ATOM | 4541 | O | GLU | A | 316 | 77.525 | −33.099 | −9.072 | 1.00 | 33.94 | O |

W352

| | | | | | | | | | | | |
|---|---|---|---|---|---|---|---|---|---|---|---|
| ATOM | 5047 | N | TRP | A | 352 | 79.387 | −32.535 | 2.052 | 1.00 | 33.36 | N |
| ATOM | 5048 | CA | TRP | A | 352 | 79.195 | −31.378 | 1.193 | 1.00 | 34.25 | C |
| ATOM | 5050 | CB | TRP | A | 352 | 80.393 | −31.224 | 0.275 | 1.00 | 33.42 | C |
| ATOM | 5053 | CG | TRP | A | 352 | 80.256 | −30.285 | −0.812 | 1.00 | 33.82 | C |
| ATOM | 5054 | CD1 | TRP | A | 352 | 79.991 | −30.583 | −2.108 | 1.00 | 36.52 | C |
| ATOM | 5056 | NE1 | TRP | A | 352 | 79.970 | −29.422 | −2.870 | 1.00 | 38.03 | N |
| ATOM | 5058 | CE2 | TRP | A | 352 | 80.266 | −28.366 | −2.054 | 1.00 | 34.34 | C |
| ATOM | 5059 | CD2 | TRP | A | 352 | 80.448 | −28.875 | −0.752 | 1.00 | 34.07 | C |
| ATOM | 5060 | CE3 | TRP | A | 352 | 80.764 | −27.996 | 0.266 | 1.00 | 33.41 | C |
| ATOM | 5062 | CZ3 | TRP | A | 352 | 80.882 | −26.669 | −0.046 | 1.00 | 34.77 | C |
| ATOM | 5064 | CH2 | TRP | A | 352 | 80.670 | −26.199 | −1.345 | 1.00 | 32.13 | C |
| ATOM | 5066 | CZ2 | TRP | A | 352 | 80.369 | −27.036 | −2.350 | 1.00 | 32.60 | C |
| ATOM | 5068 | C | TRP | A | 352 | 77.944 | −31.545 | 0.377 | 1.00 | 35.42 | C |
| ATOM | 5069 | O | TRP | A | 352 | 77.162 | −30.573 | 0.220 | 1.00 | 34.97 | O |

L383

| | | | | | | | | | | | |
|---|---|---|---|---|---|---|---|---|---|---|---|
| ATOM | 5560 | N | LEU | A | 383 | 81.514 | −30.059 | 6.041 | 1.00 | 33.60 | N |
| ATOM | 5561 | CA | LEU | A | 383 | 82.698 | −29.558 | 5.387 | 1.00 | 33.14 | C |
| ATOM | 5563 | CB | LEU | A | 383 | 82.849 | −30.198 | 3.997 | 1.00 | 32.22 | C |
| ATOM | 5566 | CG | LEU | A | 383 | 84.271 | −30.210 | 3.432 | 1.00 | 30.41 | C |
| ATOM | 5568 | CD1 | LEU | A | 383 | 84.998 | −31.420 | 3.928 | 1.00 | 26.86 | C |
| ATOM | 5572 | CD2 | LEU | A | 383 | 84.244 | −30.180 | 1.913 | 1.00 | 30.13 | C |
| ATOM | 5576 | C | LEU | A | 383 | 82.739 | −28.003 | 5.319 | 1.00 | 33.89 | C |
| ATOM | 5577 | O | LEU | A | 383 | 83.816 | −27.431 | 5.189 | 1.00 | 34.82 | O |

L407

| | | | | | | | | | | | |
|---|---|---|---|---|---|---|---|---|---|---|---|
| ATOM | 5942 | N | LEU | A | 407 | 85.930 | −24.584 | 5.772 | 1.00 | 32.59 | N |
| ATOM | 5943 | CA | LEU | A | 407 | 86.320 | −24.878 | 4.418 | 1.00 | 31.60 | C |
| ATOM | 5945 | CB | LEU | A | 407 | 85.095 | −25.125 | 3.513 | 1.00 | 31.09 | C |

TABLE 5-continued

NAGLU ACTIVE SITE COORDINATES

| ATOM | 5948 | CG | LEU | A | 407 | 85.469 | −25.860 | 2.231 | 1.00 | 29.59 | C |
|---|---|---|---|---|---|---|---|---|---|---|---|
| ATOM | 5950 | CD1 | LEU | A | 407 | 84.265 | −26.436 | 1.548 | 1.00 | 29.41 | C |
| ATOM | 5954 | CD2 | LEU | A | 407 | 86.242 | −24.914 | 1.314 | 1.00 | 28.81 | C |
| ATOM | 5958 | C | LEU | A | 407 | 87.122 | −23.696 | 3.938 | 1.00 | 32.10 | C |
| ATOM | 5959 | O | LEU | A | 407 | 88.238 | −23.855 | 3.455 | 1.00 | 31.94 | O |

F410

| ATOM | 5993 | N | PHE | A | 410 | 88.113 | −21.546 | −1.766 | 1.00 | 35.50 | N |
|---|---|---|---|---|---|---|---|---|---|---|---|
| ATOM | 5994 | CA | PHE | A | 410 | 87.816 | −22.292 | −2.970 | 1.00 | 35.55 | C |
| ATOM | 5996 | CB | PHE | A | 410 | 86.403 | −21.913 | −3.416 | 1.00 | 36.28 | C |
| ATOM | 5999 | CG | PHE | A | 410 | 85.338 | −22.278 | −2.409 | 1.00 | 37.40 | C |
| ATOM | 6000 | CD1 | PHE | A | 410 | 84.806 | −23.565 | −2.374 | 1.00 | 36.25 | C |
| ATOM | 6002 | CE1 | PHE | A | 410 | 83.842 | −23.900 | −1.462 | 1.00 | 37.66 | C |
| ATOM | 6004 | CZ | PHE | A | 410 | 83.368 | −22.967 | −0.559 | 1.00 | 39.84 | C |
| ATOM | 6006 | CE2 | PHE | A | 410 | 83.862 | −21.673 | −0.583 | 1.00 | 40.78 | C |
| ATOM | 6008 | CD2 | PHE | A | 410 | 84.861 | −21.334 | −1.503 | 1.00 | 40.34 | C |
| ATOM | 6010 | C | PHE | A | 410 | 88.853 | −22.079 | −4.104 | 1.00 | 35.49 | C |
| ATOM | 6011 | O | PHE | A | 410 | 89.318 | −20.970 | −4.342 | 1.00 | 36.22 | O |

E446

| ATOM | 6476 | N | GLU | A | 446 | 90.216 | −25.788 | −0.216 | 1.00 | 29.05 | N |
|---|---|---|---|---|---|---|---|---|---|---|---|
| ATOM | 6477 | CA | GLU | A | 446 | 90.395 | −26.416 | −1.510 | 1.00 | 28.90 | C |
| ATOM | 6479 | CB | GLU | A | 446 | 89.420 | −25.883 | −2.545 | 1.00 | 29.51 | C |
| ATOM | 6482 | CG | GLU | A | 446 | 87.955 | −26.299 | −2.308 | 1.00 | 30.21 | C |
| ATOM | 6485 | CD | GLU | A | 446 | 87.056 | −26.121 | −3.553 | 1.00 | 31.81 | C |
| ATOM | 6486 | OE1 | GLU | A | 446 | 87.399 | −25.275 | −4.446 | 1.00 | 28.17 | O |
| ATOM | 6487 | OE2 | GLU | A | 446 | 86.007 | −26.835 | −3.617 | 1.00 | 34.90 | O |
| ATOM | 6488 | C | GLU | A | 446 | 91.800 | −26.182 | −1.956 | 1.00 | 29.17 | C |
| ATOM | 6489 | O | GLU | A | 446 | 92.387 | −27.080 | −2.552 | 1.00 | 29.77 | O |

H512

| ATOM | 7475 | N | HIS | A | 512 | 85.296 | −17.499 | −2.866 | 1.00 | 47.49 | N |
|---|---|---|---|---|---|---|---|---|---|---|---|
| ATOM | 7476 | CA | HIS | A | 512 | 85.708 | −17.662 | −4.278 | 1.00 | 46.66 | C |
| ATOM | 7478 | CB | HIS | A | 512 | 84.535 | −18.022 | −5.239 | 1.00 | 47.53 | C |
| ATOM | 7481 | CG | HIS | A | 512 | 83.753 | −19.257 | −4.887 | 1.00 | 51.47 | C |
| ATOM | 7482 | ND1 | HIS | A | 512 | 83.875 | −20.448 | −5.581 | 1.00 | 57.00 | N |
| ATOM | 7484 | CE1 | HIS | A | 512 | 83.022 | −21.345 | −5.091 | 1.00 | 58.23 | C |
| ATOM | 7486 | NE2 | HIS | A | 512 | 82.338 | −20.777 | −4.111 | 1.00 | 58.45 | N |
| ATOM | 7488 | CD2 | HIS | A | 512 | 82.764 | −19.465 | −3.979 | 1.00 | 55.68 | C |
| ATOM | 7490 | C | HIS | A | 512 | 86.144 | −16.243 | −4.591 | 1.00 | 45.31 | C |
| ATOM | 7491 | O | HIS | A | 512 | 85.397 | −15.347 | −4.261 | 1.00 | 46.27 | O |

W649

| ATOM | 9656 | N | TRP | A | 649 | 90.312 | −24.706 | −17.118 | 1.00 | 32.44 | N |
|---|---|---|---|---|---|---|---|---|---|---|---|
| ATOM | 9657 | CA | TRP | A | 649 | 89.928 | −25.893 | −16.310 | 1.00 | 32.55 | C |
| ATOM | 9659 | CB | TRP | A | 649 | 88.655 | −25.653 | −15.435 | 1.00 | 32.52 | C |
| ATOM | 9662 | CG | TRP | A | 649 | 88.727 | −26.327 | −14.135 | 1.00 | 31.75 | C |
| ATOM | 9663 | CD1 | TRP | A | 649 | 89.100 | −25.775 | −12.975 | 1.00 | 32.52 | C |
| ATOM | 9665 | NE1 | TRP | A | 649 | 89.090 | −26.714 | −11.972 | 1.00 | 31.61 | N |
| ATOM | 9667 | CE2 | TRP | A | 649 | 88.699 | −27.903 | −12.496 | 1.00 | 28.87 | C |
| ATOM | 9668 | CD2 | TRP | A | 649 | 88.463 | −27.703 | −13.855 | 1.00 | 30.57 | C |
| ATOM | 9669 | CE3 | TRP | A | 649 | 88.078 | −28.778 | −14.631 | 1.00 | 31.46 | C |
| ATOM | 9671 | CZ3 | TRP | A | 649 | 87.916 | −29.981 | −14.037 | 1.00 | 32.96 | C |
| ATOM | 9673 | CH2 | TRP | A | 649 | 88.136 | −30.135 | −12.673 | 1.00 | 33.51 | C |
| ATOM | 9675 | CZ2 | TRP | A | 649 | 88.533 | −29.091 | −11.894 | 1.00 | 30.78 | C |
| ATOM | 9677 | C | TRP | A | 649 | 89.736 | −27.050 | −17.292 | 1.00 | 33.10 | C |
| ATOM | 9678 | O | TRP | A | 649 | 90.521 | −27.957 | −17.339 | 1.00 | 32.58 | O |

I655

| ATOM | 9737 | N | ILE | A | 655 | 85.048 | −24.752 | −16.565 | 1.00 | 32.71 | N |
|---|---|---|---|---|---|---|---|---|---|---|---|
| ATOM | 9738 | CA | ILE | A | 655 | 84.935 | −24.168 | −15.228 | 1.00 | 31.79 | C |
| ATOM | 9740 | CB | ILE | A | 655 | 85.235 | −25.190 | −14.041 | 1.00 | 30.84 | C |
| ATOM | 9742 | CG1 | ILE | A | 655 | 84.742 | −26.620 | −14.396 | 1.00 | 31.73 | C |
| ATOM | 9745 | CD1 | ILE | A | 655 | 84.880 | −27.705 | −13.299 | 1.00 | 28.31 | C |
| ATOM | 9749 | CG2 | ILE | A | 655 | 84.574 | −24.754 | −12.741 | 1.00 | 29.08 | C |
| ATOM | 9753 | C | ILE | A | 655 | 85.855 | −22.952 | −15.246 | 1.00 | 31.82 | C |
| ATOM | 9754 | O | ILE | A | 655 | 86.706 | −22.802 | −14.428 | 1.00 | 30.69 | O |

Y658

| ATOM | 9787 | N | TYR | A | 658 | 87.898 | −20.826 | −12.299 | 1.00 | 31.75 | N |
|---|---|---|---|---|---|---|---|---|---|---|---|
| ATOM | 9788 | CA | TYR | A | 658 | 87.503 | −21.236 | −10.962 | 1.00 | 31.49 | C |
| ATOM | 9790 | CB | TYR | A | 658 | 86.895 | −22.574 | −10.968 | 1.00 | 31.18 | C |
| ATOM | 9793 | CG | TYR | A | 658 | 86.469 | −23.042 | −9.615 | 1.00 | 33.38 | C |
| ATOM | 9794 | CD1 | TYR | A | 658 | 85.225 | −22.691 | −9.095 | 1.00 | 36.48 | C |
| ATOM | 9796 | CE1 | TYR | A | 658 | 84.790 | −23.168 | −7.847 | 1.00 | 37.73 | C |
| ATOM | 9798 | CZ | TYR | A | 658 | 85.615 | −24.007 | −7.106 | 1.00 | 38.10 | C |
| ATOM | 9799 | OH | TYR | A | 658 | 85.209 | −24.478 | −5.870 | 1.00 | 41.45 | O |
| ATOM | 9801 | CE2 | TYR | A | 658 | 86.859 | −24.369 | −7.601 | 1.00 | 37.18 | C |

TABLE 5-continued

NAGLU ACTIVE SITE COORDINATES

| | | | | | | | | | | |
|---|---|---|---|---|---|---|---|---|---|---|
| ATOM | 9803 | CD2 | TYR | A | 658 | 87.277 | −23.895 | −8.865 | 1.00 | 36.10 | C |
| ATOM | 9805 | C | TYR | A | 658 | 88.645 | −21.317 | −10.024 | 1.00 | 31.11 | C |
| ATOM | 9806 | O | TYR | A | 658 | 88.502 | −20.986 | −8.845 | 1.00 | 32.26 | O |

Table 5.2 at 2.4 Å

N134

| | | | | | | | | | | |
|---|---|---|---|---|---|---|---|---|---|---|
| ATOM | 823 | N | ASN | A | 134 | −72.112 | 63.068 | −2.136 | 1.00 | 36.65 | N |
| ATOM | 824 | CA | ASN | A | 134 | −71.795 | 62.001 | −1.228 | 1.00 | 36.21 | C |
| ATOM | 825 | CB | ASN | A | 134 | −70.478 | 62.344 | −0.509 | 1.00 | 36.95 | C |
| ATOM | 826 | CG | ASN | A | 134 | −69.752 | 61.136 | 0.116 | 1.00 | 38.60 | C |
| ATOM | 827 | OD1 | ASN | A | 134 | −70.156 | 60.591 | 1.184 | 1.00 | 40.66 | O |
| ATOM | 828 | ND2 | ASN | A | 134 | −68.552 | 60.848 | −0.438 | 1.00 | 35.78 | N |
| ATOM | 829 | C | ASN | A | 134 | −72.937 | 61.972 | −0.229 | 1.00 | 35.13 | C |
| ATOM | 830 | O | ASN | A | 134 | −73.603 | 62.970 | 0.011 | 1.00 | 33.15 | O |

C136

| | | | | | | | | | | |
|---|---|---|---|---|---|---|---|---|---|---|
| ATOM | 838 | N | CYS | A | 136 | −72.305 | 61.704 | 2.840 | 1.00 | 35.25 | N |
| ATOM | 839 | CA | CYS | A | 136 | −71.731 | 62.591 | 3.869 | 1.00 | 36.30 | C |
| ATOM | 840 | CB | CYS | A | 136 | −70.224 | 62.431 | 3.928 | 1.00 | 36.22 | C |
| ATOM | 841 | SG | CYS | A | 136 | −69.778 | 60.741 | 4.361 | 1.00 | 42.49 | S |
| ATOM | 842 | C | CYS | A | 136 | −72.015 | 64.052 | 3.634 | 1.00 | 35.37 | C |
| ATOM | 843 | O | CYS | A | 136 | −72.054 | 64.810 | 4.587 | 1.00 | 35.63 | O |

Y140

| | | | | | | | | | | |
|---|---|---|---|---|---|---|---|---|---|---|
| ATOM | 866 | N | TYR | A | 140 | −72.284 | 67.187 | 6.241 | 1.00 | 34.21 | N |
| ATOM | 867 | CA | TYR | A | 140 | −71.150 | 68.095 | 6.415 | 1.00 | 34.06 | C |
| ATOM | 868 | CB | TYR | A | 140 | −69.837 | 67.509 | 5.875 | 1.00 | 34.29 | C |
| ATOM | 869 | CG | TYR | A | 140 | −69.169 | 66.439 | 6.714 | 1.00 | 33.29 | C |
| ATOM | 870 | CD1 | TYR | A | 140 | −69.003 | 66.586 | 8.092 | 1.00 | 33.05 | C |
| ATOM | 871 | CE1 | TYR | A | 140 | −68.378 | 65.603 | 8.851 | 1.00 | 32.87 | C |
| ATOM | 872 | CZ | TYR | A | 140 | −67.889 | 64.496 | 8.236 | 1.00 | 33.44 | C |
| ATOM | 873 | OH | TYR | A | 140 | −67.275 | 63.539 | 8.978 | 1.00 | 34.74 | O |
| ATOM | 874 | CE2 | TYR | A | 140 | −68.030 | 64.326 | 6.876 | 1.00 | 33.29 | C |
| ATOM | 875 | CD2 | TYR | A | 140 | −68.652 | 65.298 | 6.123 | 1.00 | 34.30 | C |
| ATOM | 876 | C | TYR | A | 140 | −71.389 | 69.456 | 5.775 | 1.00 | 34.40 | C |
| ATOM | 877 | O | TYR | A | 140 | −70.835 | 70.430 | 6.250 | 1.00 | 34.46 | O |

W201

| | | | | | | | | | | |
|---|---|---|---|---|---|---|---|---|---|---|
| ATOM | 1381 | N | TRP | A | 201 | −74.427 | 59.112 | 9.130 | 1.00 | 35.66 | N |
| ATOM | 1382 | CA | TRP | A | 201 | −73.866 | 57.892 | 9.693 | 1.00 | 36.21 | C |
| ATOM | 1383 | CB | TRP | A | 201 | −72.602 | 58.237 | 10.523 | 1.00 | 36.25 | C |
| ATOM | 1384 | CG | TRP | A | 201 | −71.656 | 58.943 | 9.627 | 1.00 | 33.25 | C |
| ATOM | 1385 | CD1 | TRP | A | 201 | −70.817 | 58.381 | 8.723 | 1.00 | 34.61 | C |
| ATOM | 1386 | NE1 | TRP | A | 201 | −70.165 | 59.357 | 8.002 | 1.00 | 32.88 | N |
| ATOM | 1387 | CE2 | TRP | A | 201 | −70.604 | 60.576 | 8.437 | 1.00 | 31.20 | C |
| ATOM | 1388 | CD2 | TRP | A | 201 | −71.572 | 60.350 | 9.422 | 1.00 | 34.86 | C |
| ATOM | 1389 | CE3 | TRP | A | 201 | −72.222 | 61.449 | 9.988 | 1.00 | 34.70 | C |
| ATOM | 1390 | CZ3 | TRP | A | 201 | −71.890 | 62.700 | 9.557 | 1.00 | 33.13 | C |
| ATOM | 1391 | CH2 | TRP | A | 201 | −70.938 | 62.886 | 8.575 | 1.00 | 35.37 | C |
| ATOM | 1392 | CZ2 | TRP | A | 201 | −70.268 | 61.834 | 8.018 | 1.00 | 32.43 | C |
| ATOM | 1393 | C | TRP | A | 201 | −74.928 | 57.062 | 10.404 | 1.00 | 36.76 | C |
| ATOM | 1394 | O | TRP | A | 201 | −74.837 | 55.845 | 10.458 | 1.00 | 36.53 | O |

M204

| | | | | | | | | | | |
|---|---|---|---|---|---|---|---|---|---|---|
| ATOM | 1410 | N | MET | A | 204 | −76.506 | 55.040 | 7.455 | 1.00 | 37.88 | N |
| ATOM | 1411 | CA | MET | A | 204 | −75.713 | 53.891 | 7.000 | 1.00 | 37.85 | C |
| ATOM | 1412 | CB | MET | A | 204 | −74.340 | 54.372 | 6.544 | 1.00 | 37.69 | C |
| ATOM | 1413 | CG | MET | A | 204 | −74.396 | 55.111 | 5.207 | 1.00 | 38.00 | C |
| ATOM | 1414 | SD | MET | A | 204 | −72.765 | 55.434 | 4.526 | 1.00 | 43.75 | S |
| ATOM | 1415 | CE | MET | A | 204 | −72.183 | 56.718 | 5.647 | 1.00 | 37.85 | C |
| ATOM | 1416 | C | MET | A | 204 | −75.616 | 52.774 | 8.050 | 1.00 | 38.23 | C |
| ATOM | 1417 | O | MET | A | 204 | −75.112 | 51.705 | 7.756 | 1.00 | 37.19 | O |

W268

| | | | | | | | | | | |
|---|---|---|---|---|---|---|---|---|---|---|
| ATOM | 1922 | N | TRP | A | 268 | −68.219 | 51.109 | 15.370 | 1.00 | 47.56 | N |
| ATOM | 1923 | CA | TRP | A | 268 | −67.677 | 52.005 | 14.348 | 1.00 | 45.78 | C |
| ATOM | 1924 | CB | TRP | A | 268 | −68.739 | 52.270 | 13.291 | 1.00 | 45.13 | C |
| ATOM | 1925 | CG | TRP | A | 268 | −68.357 | 53.246 | 12.204 | 1.00 | 43.55 | C |
| ATOM | 1926 | CD1 | TRP | A | 268 | −67.839 | 52.943 | 10.985 | 1.00 | 42.18 | C |
| ATOM | 1927 | NE1 | TRP | A | 268 | −67.675 | 54.092 | 10.233 | 1.00 | 42.09 | N |
| ATOM | 1928 | CE2 | TRP | A | 268 | −68.068 | 55.166 | 10.981 | 1.00 | 41.65 | C |
| ATOM | 1929 | CD2 | TRP | A | 268 | −68.523 | 54.669 | 12.226 | 1.00 | 41.19 | C |
| ATOM | 1930 | CE3 | TRP | A | 268 | −69.019 | 55.572 | 13.166 | 1.00 | 40.05 | C |
| ATOM | 1931 | CZ3 | TRP | A | 268 | −69.020 | 56.934 | 12.844 | 1.00 | 40.11 | C |
| ATOM | 1932 | CH2 | TRP | A | 268 | −68.556 | 57.383 | 11.611 | 1.00 | 37.27 | C |
| ATOM | 1933 | CZ2 | TRP | A | 268 | −68.075 | 56.521 | 10.668 | 1.00 | 38.37 | C |

TABLE 5-continued

NAGLU ACTIVE SITE COORDINATES

| ATOM | 1934 | C | TRP | A | 268 | −67.222 | 53.323 | 14.970 | 1.00 | 44.95 | C |
| --- | --- | --- | --- | --- | --- | --- | --- | --- | --- | --- | --- |
| ATOM | 1935 | O | TRP | A | 268 | −67.865 | 53.860 | 15.872 | 1.00 | 44.19 | O |

N315

| ATOM | 2306 | N | ASN | A | 315 | −71.227 | 49.761 | 4.749 | 1.00 | 40.59 | N |
| --- | --- | --- | --- | --- | --- | --- | --- | --- | --- | --- | --- |
| ATOM | 2307 | CA | ASN | A | 315 | −70.284 | 50.857 | 4.563 | 1.00 | 41.14 | C |
| ATOM | 2308 | CB | ASN | A | 315 | −71.024 | 52.154 | 4.266 | 1.00 | 41.63 | C |
| ATOM | 2309 | CG | ASN | A | 315 | −70.157 | 53.156 | 3.545 | 1.00 | 43.78 | C |
| ATOM | 2310 | OD1 | ASN | A | 315 | −70.031 | 53.110 | 2.304 | 1.00 | 46.72 | O |
| ATOM | 2311 | ND2 | ASN | A | 315 | −69.560 | 54.068 | 4.302 | 1.00 | 40.92 | N |
| ATOM | 2312 | C | ASN | A | 315 | −69.408 | 51.017 | 5.814 | 1.00 | 40.93 | C |
| ATOM | 2313 | O | ASN | A | 315 | −69.894 | 51.381 | 6.884 | 1.00 | 40.18 | O |

E316

| ATOM | 2314 | N | GLU | A | 316 | −68.127 | 50.660 | 5.677 | 1.00 | 41.46 | N |
| --- | --- | --- | --- | --- | --- | --- | --- | --- | --- | --- | --- |
| ATOM | 2315 | CA | GLU | A | 316 | −67.164 | 50.727 | 6.760 | 1.00 | 41.62 | C |
| ATOM | 2316 | CB | GLU | A | 316 | −66.986 | 52.179 | 7.214 | 1.00 | 41.25 | C |
| ATOM | 2317 | CG | GLU | A | 316 | −66.448 | 53.059 | 6.071 | 1.00 | 42.20 | C |
| ATOM | 2318 | CD | GLU | A | 316 | −65.756 | 54.352 | 6.548 | 1.00 | 44.21 | C |
| ATOM | 2319 | OE1 | GLU | A | 316 | −65.948 | 54.784 | 7.716 | 1.00 | 42.48 | O |
| ATOM | 2320 | OE2 | GLU | A | 316 | −65.016 | 54.932 | 5.721 | 1.00 | 45.98 | O |
| ATOM | 2321 | C | GLU | A | 316 | −67.502 | 49.804 | 7.938 | 1.00 | 42.09 | C |
| ATOM | 2322 | O | GLU | A | 316 | −67.095 | 50.058 | 9.058 | 1.00 | 41.71 | O |

W352

| ATOM | 2581 | N | TRP | A | 352 | −67.648 | 52.263 | −2.112 | 1.00 | 41.67 | N |
| --- | --- | --- | --- | --- | --- | --- | --- | --- | --- | --- | --- |
| ATOM | 2582 | CA | TRP | A | 352 | −66.601 | 52.653 | −1.141 | 1.00 | 41.21 | C |
| ATOM | 2583 | CB | TRP | A | 352 | −67.128 | 53.711 | −0.176 | 1.00 | 40.35 | C |
| ATOM | 2584 | CG | TRP | A | 352 | −66.179 | 54.141 | 0.893 | 1.00 | 39.63 | C |
| ATOM | 2585 | CD1 | TRP | A | 352 | −66.252 | 53.817 | 2.213 | 1.00 | 39.75 | C |
| ATOM | 2586 | NE1 | TRP | A | 352 | −65.204 | 54.378 | 2.897 | 1.00 | 40.88 | N |
| ATOM | 2587 | CE2 | TRP | A | 352 | −64.449 | 55.122 | 2.034 | 1.00 | 38.25 | C |
| ATOM | 2588 | CD2 | TRP | A | 352 | −65.029 | 54.989 | 0.750 | 1.00 | 39.45 | C |
| ATOM | 2589 | CE3 | TRP | A | 352 | −64.440 | 55.649 | −0.333 | 1.00 | 40.99 | C |
| ATOM | 2590 | CZ3 | TRP | A | 352 | −63.301 | 56.414 | −0.105 | 1.00 | 41.86 | C |
| ATOM | 2591 | CH2 | TRP | A | 352 | −62.747 | 56.531 | 1.208 | 1.00 | 41.59 | C |
| ATOM | 2592 | CZ2 | TRP | A | 352 | −63.329 | 55.906 | 2.283 | 1.00 | 37.94 | C |
| ATOM | 2593 | C | TRP | A | 352 | −66.076 | 51.463 | −0.354 | 1.00 | 41.91 | C |
| ATOM | 2594 | O | TRP | A | 352 | −64.850 | 51.315 | −0.169 | 1.00 | 41.99 | O |

L383

| ATOM | 2835 | N | LEU | A | 383 | −66.537 | 55.238 | −6.137 | 1.00 | 42.27 | N |
| --- | --- | --- | --- | --- | --- | --- | --- | --- | --- | --- | --- |
| ATOM | 2836 | CA | LEU | A | 383 | −66.705 | 56.500 | −5.439 | 1.00 | 42.36 | C |
| ATOM | 2837 | CB | LEU | A | 383 | −67.263 | 56.291 | −4.018 | 1.00 | 41.85 | C |
| ATOM | 2838 | CG | LEU | A | 383 | −67.998 | 57.484 | −3.399 | 1.00 | 41.25 | C |
| ATOM | 2839 | CD1 | LEU | A | 383 | −69.300 | 57.764 | −4.106 | 1.00 | 38.16 | C |
| ATOM | 2840 | CD2 | LEU | A | 383 | −68.228 | 57.269 | −1.903 | 1.00 | 39.98 | C |
| ATOM | 2841 | C | LEU | A | 383 | −65.442 | 57.304 | −5.389 | 1.00 | 42.70 | C |
| ATOM | 2842 | O | LEU | A | 383 | −65.518 | 58.526 | −5.385 | 1.00 | 44.13 | O |

L407

| ATOM | 3032 | N | LEU | A | 407 | −64.050 | 61.742 | −5.815 | 1.00 | 39.89 | N |
| --- | --- | --- | --- | --- | --- | --- | --- | --- | --- | --- | --- |
| ATOM | 3033 | CA | LEU | A | 407 | −64.412 | 62.019 | −4.434 | 1.00 | 38.85 | C |
| ATOM | 3034 | CB | LEU | A | 407 | −63.995 | 60.860 | −3.522 | 1.00 | 38.31 | C |
| ATOM | 3035 | CG | LEU | A | 407 | −64.790 | 60.747 | −2.218 | 1.00 | 37.58 | C |
| ATOM | 3036 | CD1 | LEU | A | 407 | −64.566 | 59.408 | −1.557 | 1.00 | 37.21 | C |
| ATOM | 3037 | CD2 | LEU | A | 407 | −64.429 | 61.857 | −1.265 | 1.00 | 36.81 | C |
| ATOM | 3038 | C | LEU | A | 407 | −63.746 | 63.303 | −3.999 | 1.00 | 39.48 | C |
| ATOM | 3039 | O | LEU | A | 407 | −64.402 | 64.235 | −3.501 | 1.00 | 39.34 | O |

F410

| ATOM | 3058 | N | PHE | A | 410 | −62.395 | 65.225 | 1.717 | 1.00 | 39.99 | N |
| --- | --- | --- | --- | --- | --- | --- | --- | --- | --- | --- | --- |
| ATOM | 3059 | CA | PHE | A | 410 | −62.817 | 64.542 | 2.948 | 1.00 | 39.83 | C |
| ATOM | 3060 | CB | PHE | A | 410 | −61.731 | 63.559 | 3.381 | 1.00 | 39.95 | C |
| ATOM | 3061 | CG | PHE | A | 410 | −61.527 | 62.416 | 2.397 | 1.00 | 41.94 | C |
| ATOM | 3062 | CD1 | PHE | A | 410 | −62.342 | 61.280 | 2.441 | 1.00 | 42.71 | C |
| ATOM | 3063 | CE1 | PHE | A | 410 | −62.178 | 60.252 | 1.541 | 1.00 | 43.59 | C |
| ATOM | 3064 | CZ | PHE | A | 410 | −61.196 | 60.343 | 0.566 | 1.00 | 45.30 | C |
| ATOM | 3065 | CE2 | PHE | A | 410 | −60.393 | 61.474 | 0.503 | 1.00 | 44.19 | C |
| ATOM | 3066 | CD2 | PHE | A | 410 | −60.577 | 62.504 | 1.402 | 1.00 | 43.71 | C |
| ATOM | 3067 | C | PHE | A | 410 | −63.099 | 65.538 | 4.062 | 1.00 | 39.11 | C |
| ATOM | 3068 | O | PHE | A | 410 | −62.400 | 66.536 | 4.219 | 1.00 | 40.24 | O |

E446

| ATOM | 3306 | N | GLU | A | 446 | −67.074 | 64.899 | 0.220 | 1.00 | 38.26 | N |
| --- | --- | --- | --- | --- | --- | --- | --- | --- | --- | --- | --- |
| ATOM | 3307 | CA | GLU | A | 446 | −67.708 | 64.782 | 1.525 | 1.00 | 37.13 | C |
| ATOM | 3308 | CB | GLU | A | 446 | −66.766 | 64.216 | 2.545 | 1.00 | 37.26 | C |
| ATOM | 3309 | CG | GLU | A | 446 | −66.578 | 62.728 | 2.332 | 1.00 | 37.69 | C |

TABLE 5-continued

NAGLU ACTIVE SITE COORDINATES

| ATOM | 3310 | CD | GLU | A | 446 | −65.866 | 62.023 | 3.506 | 1.00 | 37.77 | C |
|---|---|---|---|---|---|---|---|---|---|---|---|
| ATOM | 3311 | OE1 | GLU | A | 446 | −65.311 | 62.692 | 4.410 | 1.00 | 35.63 | O |
| ATOM | 3312 | OE2 | GLU | A | 446 | −65.849 | 60.771 | 3.485 | 1.00 | 36.04 | O |
| ATOM | 3313 | C | GLU | A | 446 | −68.249 | 66.096 | 1.975 | 1.00 | 36.84 | C |
| ATOM | 3314 | O | GLU | A | 446 | −69.250 | 66.126 | 2.665 | 1.00 | 36.84 | O |

H512 (multiple conformation)

| ATOM | 3816 | N | HIS | A | 512 | −57.589 | 64.956 | 2.697 | 1.00 | 48.45 | N |
|---|---|---|---|---|---|---|---|---|---|---|---|
| ATOM | 3817 | CA | AHIS | A | 512 | −57.747 | 65.169 | 4.147 | 0.25 | 47.54 | C |
| ATOM | 3818 | CA | BHIS | A | 512 | −57.775 | 65.235 | 4.112 | 0.25 | 47.92 | C |
| ATOM | 3819 | CA | CHIS | A | 512 | −57.818 | 65.254 | 4.107 | 0.50 | 47.86 | C |
| ATOM | 3820 | CB | AHIS | A | 512 | −57.341 | 63.926 | 4.993 | 0.25 | 47.44 | C |
| ATOM | 3821 | CB | BHIS | A | 512 | −57.691 | 63.950 | 4.974 | 0.25 | 47.96 | C |
| ATOM | 3822 | CB | CHIS | A | 512 | −57.825 | 63.956 | 4.950 | 0.50 | 47.78 | C |
| ATOM | 3823 | CG | AHIS | A | 512 | −58.136 | 62.663 | 4.772 | 0.25 | 45.45 | C |
| ATOM | 3824 | CG | BHIS | A | 512 | −56.484 | 63.081 | 4.723 | 0.25 | 48.37 | C |
| ATOM | 3825 | CG | CHIS | A | 512 | −58.634 | 64.042 | 6.220 | 0.50 | 48.03 | C |
| ATOM | 3826 | ND1 | AHIS | A | 512 | −59.344 | 62.413 | 5.390 | 0.25 | 43.31 | N |
| ATOM | 3827 | ND1 | BHIS | A | 512 | −56.559 | 61.703 | 4.745 | 0.25 | 48.69 | N |
| ATOM | 3828 | ND1 | CHIS | A | 512 | −58.267 | 63.395 | 7.388 | 0.50 | 46.74 | N |
| ATOM | 3829 | CE1 | AHIS | A | 512 | −59.765 | 61.201 | 5.068 | 0.25 | 42.02 | C |
| ATOM | 3830 | CE1 | BHIS | A | 512 | −55.362 | 61.191 | 4.510 | 0.25 | 48.58 | C |
| ATOM | 3831 | CE1 | CHIS | A | 512 | −59.156 | 63.651 | 8.327 | 0.50 | 45.69 | C |
| ATOM | 3832 | NE2 | AHIS | A | 512 | −58.853 | 60.635 | 4.302 | 0.25 | 42.59 | N |
| ATOM | 3833 | NE2 | BHIS | A | 512 | −54.509 | 62.184 | 4.346 | 0.25 | 47.79 | N |
| ATOM | 3834 | NE2 | CHIS | A | 512 | −60.087 | 64.446 | 7.816 | 0.50 | 47.65 | N |
| ATOM | 3835 | CD2 | AHIS | A | 512 | −57.814 | 61.518 | 4.121 | 0.25 | 44.11 | C |
| ATOM | 3836 | CD2 | BHIS | A | 512 | −55.183 | 63.376 | 4.474 | 0.25 | 48.02 | C |
| ATOM | 3837 | CD2 | CHIS | A | 512 | −59.790 | 64.698 | 6.500 | 0.50 | 46.26 | C |
| ATOM | 3838 | C | HIS | A | 512 | −56.726 | 66.257 | 4.538 | 1.00 | 47.82 | C |
| ATOM | 3839 | O | HIS | A | 512 | −55.558 | 66.131 | 4.192 | 1.00 | 47.68 | O |

W649

| ATOM | 4943 | N | TRP | A | 649 | −66.166 | 65.489 | 17.169 | 1.00 | 39.55 | N |
|---|---|---|---|---|---|---|---|---|---|---|---|
| ATOM | 4944 | CA | TRP | A | 649 | −67.015 | 64.568 | 16.383 | 1.00 | 39.46 | C |
| ATOM | 4945 | CB | TRP | A | 649 | −66.215 | 63.634 | 15.457 | 1.00 | 39.04 | C |
| ATOM | 4946 | CG | TRP | A | 649 | −66.897 | 63.337 | 14.165 | 1.00 | 37.97 | C |
| ATOM | 4947 | CD1 | TRP | A | 649 | −66.650 | 63.926 | 12.957 | 1.00 | 35.62 | C |
| ATOM | 4948 | NE1 | TRP | A | 649 | −67.446 | 63.378 | 11.993 | 1.00 | 35.74 | N |
| ATOM | 4949 | CE2 | TRP | A | 649 | −68.258 | 62.438 | 12.565 | 1.00 | 36.71 | C |
| ATOM | 4950 | CD2 | TRP | A | 649 | −67.939 | 62.379 | 13.933 | 1.00 | 36.95 | C |
| ATOM | 4951 | CE3 | TRP | A | 649 | −68.635 | 61.485 | 14.749 | 1.00 | 37.24 | C |
| ATOM | 4952 | CZ3 | TRP | A | 649 | −69.601 | 60.687 | 14.179 | 1.00 | 38.16 | C |
| ATOM | 4953 | CH2 | TRP | A | 649 | −69.893 | 60.765 | 12.804 | 1.00 | 35.66 | C |
| ATOM | 4954 | CZ2 | TRP | A | 649 | −69.237 | 61.636 | 11.992 | 1.00 | 37.43 | C |
| ATOM | 4955 | C | TRP | A | 649 | −67.920 | 63.805 | 17.313 | 1.00 | 40.16 | C |
| ATOM | 4956 | O | TRP | A | 649 | −69.127 | 64.062 | 17.349 | 1.00 | 40.14 | O |

I655

| ATOM | 4989 | N | ILE | A | 655 | −63.561 | 60.936 | 16.597 | 1.00 | 40.72 | N |
|---|---|---|---|---|---|---|---|---|---|---|---|
| ATOM | 4990 | CA | ILE | A | 655 | −62.948 | 61.129 | 15.284 | 1.00 | 40.83 | C |
| ATOM | 4991 | CB | ILE | A | 655 | −63.930 | 60.872 | 14.069 | 1.00 | 40.04 | C |
| ATOM | 4992 | CG1 | ILE | A | 655 | −64.975 | 59.796 | 14.389 | 1.00 | 40.23 | C |
| ATOM | 4993 | CD1 | ILE | A | 655 | −65.915 | 59.447 | 13.201 | 1.00 | 36.48 | C |
| ATOM | 4994 | CG2 | ILE | A | 655 | −63.133 | 60.469 | 12.818 | 1.00 | 37.05 | C |
| ATOM | 4995 | C | ILE | A | 655 | −62.386 | 62.553 | 15.221 | 1.00 | 41.27 | C |
| ATOM | 4996 | O | ILE | A | 655 | −62.730 | 63.344 | 14.325 | 1.00 | 41.22 | O |

Y658

| ATOM | 5013 | N | TYR | A | 658 | −61.544 | 65.417 | 12.255 | 1.00 | 37.64 | N |
|---|---|---|---|---|---|---|---|---|---|---|---|
| ATOM | 5014 | CA | TYR | A | 658 | −61.795 | 64.865 | 10.940 | 1.00 | 36.91 | C |
| ATOM | 5015 | CB | TYR | A | 658 | −62.614 | 63.570 | 11.021 | 1.00 | 36.40 | C |
| ATOM | 5016 | CG | TYR | A | 658 | −62.812 | 62.992 | 9.646 | 1.00 | 38.05 | C |
| ATOM | 5017 | CD1 | TYR | A | 658 | −61.865 | 62.134 | 9.087 | 1.00 | 36.67 | C |
| ATOM | 5018 | CE1 | TYR | A | 658 | −62.028 | 61.640 | 7.807 | 1.00 | 37.90 | C |
| ATOM | 5019 | CZ | TYR | A | 658 | −63.151 | 62.020 | 7.042 | 1.00 | 38.19 | C |
| ATOM | 5020 | OH | TYR | A | 658 | −63.305 | 61.547 | 5.755 | 1.00 | 36.46 | O |
| ATOM | 5021 | CE2 | TYR | A | 658 | −64.092 | 62.893 | 7.558 | 1.00 | 36.53 | C |
| ATOM | 5022 | CD2 | TYR | A | 658 | −63.925 | 63.366 | 8.858 | 1.00 | 38.89 | C |

TABLE 5-continued

| | | | | | | | | | | | |
|---|---|---|---|---|---|---|---|---|---|---|---|
| ATOM | 5023 | C | TYR | A | 658 | −62.509 | 65.873 | 10.050 | 1.00 | 36.66 | C |
| ATOM | 5024 | O | TYR | A | 658 | −62.201 | 65.974 | 8.866 | 1.00 | 38.05 | O |

Column 4 - amino acid name
Column 5 - chain id
Column 6 - amino acid number
Columns 7, 8 and 9 are x, y, z coordinates
Column 10 - occupancy
Column 11 - B factor

TABLE 10

GLYCOSIDE HYDROLASE FAMILY 89

Bacteria (31)

| Protein Name EC # | Organism | GenBank | Uniprot | PDB/3D |
|---|---|---|---|---|
| ACP_3498 | *Acidobacterium capsulatum* ATCC 51196 | ACO33861.1 | | |
| Amuc_0060 | *Akkermansia muciniphila* ATCC BAA-835 | ACD03906.1 | B2ULB7 | |
| Amuc_1220 | *Akkermansia muciniphila* ATCC BAA-835 | ACD05045.1 | B2URG0 | |
| AL1_27260 | *Alistipes shahii* WAL 8301 | CBK64878.1 | | |
| BF0603 | *Bacteroides fragilis* NCTC 9343 ATCC 25285 | CAH06355.1 | Q5LHM5 | |
| BF0678 | *Bacteroides fragilis* YCH46 | BAD47426.1 | | |
| BT4359 | *Bacteroides thetaiotaomicron* VPI-5482 | AAO79464.1/NP_813270.1 | | |
| BT0438 | *Bacteroides thetaiotaomicron* VPI-5482 | AAO75545.1/NP_809351.1 | | |
| BT3590 | *Bacteroides thetaiotaomicron* VPI-5482 | AAO78695.1/NP_812501.1 | | |
| BVU_1860 | *Bacteroides vulgatus* ATCC 8482 | ABR39535.1 | A6L1H1 | |
| Bcav_0303 | *Beutenbergia cavernae* DSM 12333 | ACQ78567.1 | | |
| Bfae_05050 | *Brachybacterium faecium* DSM 4810 | ACU84374.1 | | |
| CC0540 | *Caulobacter crescentus* CB15 | AAK22527.1/NP_419359.1 | | |
| CCNA_00574 | *Caulobacter crescentus* NA1000 | ACL94039.1 | | |
| Cpin_3125 α-N-acetyl-glucosaminidase | *Chitinophaga pinensis* DSM 2588 | ACU60593.1 | | |
| CPF_0859) 3.2.1.50 | *Clostridium perfringens* ATCC 13124 | ABG84150.1 | Q0TST1 | 2VC9[A] 2VCA[A] 2VCB[A] 2VCC[A] |
| CPR_0850 α-N-acetyl-glucosaminidase | *Clostridium perfringens* SM101 | ABG85709.1 | Q0SUN2 | |
| (AgnC;CPE0866) | *Clostridium perfringens* str. 13 | BAB80572.1 BAI70446.1 NP_561782.1 | Q8XM24 | |
| Fjoh_3128 | *Flavobacterium johnsoniae* UW101 | ABQ06145.1 | A5FF78 | |
| Phep_3401 | *Pedobacter heparinus* DSM 2366 | ACU05595.1 | | |
| Phep_3402 | *Pedobacter heparinus* DSM 2366 | ACU05596.1 | | |
| Phep_3785 | *Pedobacter heparinus* DSM 2366 | ACU05976.1 | | |
| SARI_03139 | *Salmonella enterica* subsp. *arizonae* serovar 62:z4,z23:- RSK2980 | ABX22979.1 | A9MER3 | |
| SAML0573 | *Streptomyces ambofaciens* ATCC 23877 | CAJ89559.1 | A3KIM5 | |
| SAV2014 | *Streptomyces avermitilis* MA-4680 | BAC69725.1/NP_823190.1 | | |
| SAV5988 | *Streptomyces avermitilis* MA-4680 | BAC73700.1/NP_827165.1 | | |
| SCAB_18501 | *Streptomyces scabiei* 87.22 | CBG68977.1 | | |
| XAC0709 | *Xanthomonas axonopodis* pv. citri str. 306 | AAM35598.1/NP_641062.1 | | |
| XOO3922 | *Xanthomonas oryzae* pv. *oryzae* KACC10331 | AAW77176.1 | | |
| XOO3702 (fragment) | *Xanthomonas oryzae* pv. *oryzae* MAFF 311018 | BAE70457.1 | Q2NZ20 | |
| XOO3701 (prob.fragm.) | *Xanthomonas oryzae* pv. *oryzae* MAFF 311018 | BAE70456.1 | Q2NZ21 | |

Eukaryota (18)

| Protein Name EC # | Organism | GenBank | Uniprot |
|---|---|---|---|
| AgCG51100 α-N-acetyl-glucosaminidase | *Anopheles gambiae* str. PEST | EAA00039.1 | |
| (NAGLU;At5g13690) | *Arabidopsis thaliana* | AAL87291.1 AAM51254.1 BAB08696.1 BAD94027.1 NP_196873.1 | Q9FNA3 |
| AO090010000111 (prob. fragm.) | *Aspergillus oryzae* RIB40 | BAE66022.1 | |
| ORF (protein for MGC:157257) | *Bos taurus* | AAI48148.1 | A6QM01 |
| CBG20846 (fragment) | *Caenorhabditis briggsae* | CAE73404.1 | |

TABLE 10-continued

GLYCOSIDE HYDROLASE FAMILY 89

| | | | |
|---|---|---|---|
| K09E4.4 | *Caenorhabditis elegans* Bristol N2 | CAB70170.2 | Q9NAP6 |
| α-N-acetyl- | | NP_496948.1 | |
| glucosaminidase (Naglu) | | | |
| (lysosomal) | *Dromaius novaehollandiae* | AAK73654.1 | Q90Z75 |
| | | AAK73655.1 | Q90Z76 |
| CG13397 | *Drosophila melanogaster* | AAF52672.2 | |
| | | AAL13967.1 | |
| | | NP_652045.1 | Q9VLL5 |
| α-N-acetyl- | | | |
| glucosaminidase | | | |
| (Sanfilippo disease IIIB) | | | |
| (NAGLU) 3.2.1.50 | *Homo sapiens* | AAB06188.1 | |
| | | AAB36604.1 | |
| | | AAB36605.1 | |
| | | AAC50512.1 | |
| | | AAC50513.1 | |
| | | AAH53991.1 | |
| | | ACM85779.1 | |
| | | BAD92767.1 | |
| | | NP_000254.1 | |
| | | NP_000254.2 | P54802 |
| | | | Q14769 |
| MICPUN_59291 | *Micromonas* sp. RCC299 | ACO64474.1 | |
| α-N-acetyl- | | | |
| glucosaminidase | | | |
| (Naglu) 3.2.1.50 | *Mus musculus* | AAB88084.1 | |
| | | AAC26842.1 | |
| | | AAH55733.1 | |
| | | AAM21194.1 | |
| | | BAE37639.1 | |
| | | BAE42009.1 | |
| | | CAM24462.1 | |
| | | NP_038820.1 | O54752 |
| | | | O88325 |
| ORF | *Nicotiana tabacum* BRIGHT YELLOW 2 | CAA77084.1 | Q9ZR45 |
| H0212B02.15 | *Oryza sativa* Indica Group | CAJ86183.1/CAJ86322.1 | |
| Os04g0650900 | *Oryza sativa* Japonica Group B | AF 16009.1 | |
| | | CAE04506.1 | |
| | | CAE04506.2 | Q7XMP5 |
| VITISV_031934 (fragm.) | *Vitis vinifera* | CAN83148.1 | A5BEA1 |
| unknown (fragment) | *Zea mays* | ACG29992.1 | |
| unknown | | | |
| (ZM_BFb0134E13) | *Zea mays* B73 | ACF81735.1 | B4FHZ2 |
| (fragm.) unknown | | | |
| (ZM_BFb0029M16) | *Zea mays* B73 | ACF79958.1 | B4FCW5 |
| (short fragm.) | | | |

Known Activities: α-N-acetylglucosaminidase (EC 3.2.1.50)
Mechanism: Retaining
3D Structure Status: (β/α) 8
Catalytic Nucleophile/Base: Glu
Catalytic Proton Donor: Glu

SEQUENCE LISTING

```
Naglu amino acid sequence (SEQ ID NO: 1):
MEAVAVAAAVGVLLLAGAGGAAGDEAREAAAVRALVARLLGPGPAADFSVSVERALAAKPGLDTYSLGGG
GAARVRVRGSTGVAAAAGLHRYLRDFCGCHVAWSGSQLRLPRPLPAVPGELTEATPNRYRYYQNVCTQSY
SFVWWDWAREREIDWMALNGINLALAWSGQEAIWQRVYLALGLTQAEINEFFTGPAFLAWGRMGNLHTW
DGPLPPSWHIKQLYLQHRVLDQMRSFGMTPVLPAFAGHVPEAVTRVFPQVNVTKMGSWGHFNCSYSCSFL
LAPEDPIFPIIGSLFLRELIKEFGTDHIYGADTFNEMQPPSSEPSYLAAATTAVYEAMTAVDTEAVWLLQ
GWLFQHQPQFWGPAQIRAVLGAVPRGRLLVLDLFAESQPVYTRTASFQGQPFIWCMLHNFGGNHGLFGAL
EAVNGGPEAARLFPNSTMVGTGMAPEGISQNEVVYSLMAELGWRKDPVPDLAAWVTSFAARRYGVSHPDA
GAAWRLLLRSVYNCSGEACRGHNRSPLVRRPSLQMNTSIWYNRSDVFEAWRLLLTSAPSLATSPAFRYDL
LDLTRQAVQELVSLYYEEARSAYLSKELASLLRAGGVLAYELLPALDEVLASDSRFLLGSWLEQARAAAV
SEAEADFYEQNSRYQLTLWGPEGNILDYANKQLAGLVANYYTPRWRLFLEALVDSVAQGIPFQQHQPFDKN
VFQLEQAFVLSKQRYPSQPRGDTVDLAKKIFLKYYPRWVAGSW(SEQ ID NO: 1)
underlined: signal sequence cpGH89 (PDB ID: 2VCC) amino acid sequence (SEQ ID NO: 2):
GVEITEGVTVTAKGNTEGNTADLAIDGDLSTYWESSNDYKWIEVDLGGIYELSKIEIFNKDEAVYKYNIY
ASEDGENFNKIAYKNNDNVSDSNGNMHTIDNVRAGKIRIDVVQNSNSDRVNIAEINVFGKNTGESLPEVK
KIATSNFSETPWATEYEKFNSDSAYANEKTLNEIKNLVGRVIGREFKDKFIFEIRDQLNGNDVFEVSDSG
DGKVLIKGNNGVSLASGFNYYLKNYCNVSYNPIMGSNLKMPETMPSVGERVVIDTPYEHRYALNFCTYSY
```

SEQUENCE LISTING

```
TMSFWDWDQYEEFLDWCAMNGVNLVLDIIGQEEVLRRTLNEFGYSDEEVKEFISGPAYFAWFYMQNMTGF
GGPLPNDWFEQRAELGRKMHDRMQSFGINPVLQGYSGMVPRDFKEKNQEAQTISQGGWCGFDRPDMLKTY
VNEGEADYFQKVADVFYEKQKEVFGDVTNFYGVDPFHEGGNTGDLDNGKIYEIIQNKMIEHDNDAVWVIQ
NWQGNPSNNKLEGLTKKDQAMVLDLFSEVSPDWNRLEERDLPWIWNMLHNFGGRMGMDAAPEKLATEIPK
ALANSEHMVGIGITPEAINTNPLAYELLFDMAWTRDQINFRTWTEDYIERRYGKTNKEILEAWNIILDTA
YKKRNDYYQGAAESIINARPGFGIKSASTWGHSKIVYDKSEFEKAIEIFAKNYDEFKDSDAFLYDFADIL
KQLLANSAQEYYEVMCNAYNNGNGEKPKFVSGKFLELIKLQERVLSTRPEFLIGNWIEDARTMLKDSDDW
TKDLFEFNARALVTTWGSRNNADGGGLKDYSNRQWSGLTEDYYARWEKWINGLQAELDGGAKAPNIDWF
KMEYDWVNKKSDTDKLYPTEASNENLGELAKIAMESYSVTNMDKILGENES(SEQ ID NO: 2)

Naglu amino acid sequence 24-743 (SEQ ID NO: 3):
DEAREAAVRALVARLLGPGPAADFSVSVERALAAKPGLDTYSLGGGGAARVRVRGSTGVAAAAGLHRYL
RDFCGCHVAWSGSQLRLPRPLPAVPGELTEATPNRYRYYQNVCTQSYSFVWWDWARWEREIDWMALNGIN
LALAWSGQEAIWQRVYLALGLTQAEINEFFTGPAFLAWGRMGNLHTWDGPLPPSWHIKQLYLQHRVLDQM
RSFGMTPVLPAFAGHVPEAVTRVFPQVNVTKMGSWGHFNCSYSCSFLLAPEDPIFPIIGSLFLRELIKEF
GTDHIYGADTFNEMQPPSSEPSYLAAATTAVYEAMTAVDTEAVWLLQGWLFQHQPQFWGPAQIRAVLGAV
PRGRLLVLDLFAESQPVYTRTASFQGQPFIWCMLHNFGGNHGLFGALEAVNGGPEAARLFPNSTMVGTGM
APEGISQNEVVYSLMAELGWRKDPVPDLAAWVTSFAARRYGVSHPDAGAAWRLLLRSVYNCSGEACRGHN
RSPLVRRPSLQMNTSIWYNRSDVFEAWRLLLTSAPSLATSPAFRYDLLDLTRQAVQELVSLYYEEARSAY
LSKELASLLRAGGVLAYELLPALDEVLASDSRFLLGSWLEQARAAAVSEAEADFYEQNSRYQLTLWGPEG
NILDYANKQLAGLVANYYTPRWRLFLEALVDSVAQGIPFQQHQFDKNVFQLEQAFVLSKQRYPSQPRGDT
VDLAKKIFLKYYPRWVAGSW(SEQ ID NO: 3)

Naglu nucleotide sequence (SEQ ID NO: 4):
ATGGAGGCGGTGGCGGTGGCCGCGGCGGTGGGGGTCCTTCTCCTGGCCGGGGCCGGGGGCGCGGCAGGCG
ACGAGGCCCGGGAGGCGGCGGCCGTGCGGGCGCTCGTGGCCCGGCTGCTGGGGCAGGCCCCGCGGCCGA
CTTCTCCGTGTCGGTGGAGCGCGCTCTGGCTGCCAAGCCGGGCTTGGACACCTACAGCCTGGGCGGCGGC
GGCGCGGCCGCGTGCGGGTGCGCGGCTCCACGGGCGTGGCGGCCGCCGGGGCTGCACCGCTACCTGC
GCGACTTCTGTGGCTGCCACGTGGCCTGGTCCGGCTCTCAGCTGCGCCTGCCGCGGCCACTGCCAGCCGT
GCCGGGGGAGCTGACCGAGGCCACGCCCAACAGGTACCGCTATTACCAGAATGTGTGCACGCAAAGCTAC
TCCTTCGTGTGGTGGGACTGGGCCCGCTGGGAGCGAGAGATAGACTGGATGGCGCTGAATGGCATCAACC
TGGCACTGGCCTGGAGCGGCCAGGAGGCCATCTGGCAGCGGGTGTACCTGGCCTTGGGCCTGACCCAGGC
AGAGATCAATGAGTTCTTTACTGGTCCTGCCTTCCTGGCCTGGGGCGAATGGGCAACCTGCACACCTGG
GATGGCCCCCTGCCCCCCTCCTGGCACATCAAGCAGCTTTACCTGCAGCACCGGGTCCTGGACCAGATGC
GCTCCTTCGGCATGACCCCAGTGCTGCCTGCATTCGCGGGGCATGTTCCCGAGGCTGTCACCAGGGTGTT
CCCTCAGGTCAATGTCACGAAGATGGGCAGTTGGGGCCACTTTAACTGTTCCTACTCCTGCTCCTTCCTT
CTGGCTCCGGAAGACCCCATATTCCCCATCATCGGGAGCCTCTTCCTGCGAGAGCTGATCAAAGAGTTTG
GCACAGACCACATCTATGGGGCCGACACTTTCAATGAGATGCAGCCACCTTCCTCAGAGCCCTCCTACCT
TGCCGCAGCCACCACTGCCGTCTATGAGGCCATGACTGCAGTGGATACTGAGGCTGTGTGGCTGCTCCAA
GGCTGGCTCTTCCAGCACCAGCCGCAGTTCTGGGGGCCCGCCCAGATCAGGGCTGTGCTGGGAGCTGTGC
CCCGTGGCCGCCTCCTGGTTCTGGACCTGTTTGCTGAGAGCCAGCCTGTGTATACCCGCACTGCCTCCTT
CCAGGGCCAGCCCTTCATCGTGGTCATGCTGCACAACTTTGGGGGAAACCATGGTCTTTTTGGAGCCCTA
GAGGCTGTGAACGGAGGCCCAGAAGCTGCCCGCCTCTTCCCCAACTCCACCATGGTAGGCACGGGCATGG
CCCCCGAGGGCATCAGCCAGAACGAAGTGGTCTATTCCCTCATGGCTGAGCTGGGCTGGCGAAAGGACCC
AGTGCCAGATTTGGCAGCTGGGTGACCAGCTTTGCCGCCCGGCGGTAGGGGTCTCCCACCCGGACGCA
GGGGCAGCGTGGAGGCTACTGCTCCGGAGTGTGTACAACTGCTCCGGGGAGGCCTGCAGGGGCCACAATC
GTAGCCCGCTGGTCAGGCGGCCGTCCCTACAGATGAATACCAGCATCTGGTACAACCGATCTGATGTGTT
TGAGGCCTGGCGGCTGCTGCTCACATCTGCTCCCTCCCTGGCCACCAGCCCCGCCTTCCGCTACGACCTG
CTGGACCTCACTCGGCAGGCAGTGCAGGAGCTGGTCAGCTTGTACTATGAGGAGGCAAGAAGCGCCTACC
TGAGCAAGGAGCTGGCCTCCCTGTTGAGGGCTGGAGGCGTCCTGGCCTATGAGCTGCTGCCGGCACTGGA
CGAGGTGCTGGCTAGTGACAGCCGCTTCTTGCTGGGCAGCTGGCTAGAGCAGGCCCGAGCAGCGGCAGTC
AGTGAGGCCGAGGCCGATTTCTACGAGCAGAACAGCCGCTACCAGCTGACCTTGTGGGGGCCAGAAGGCA
ACATCCTGGACTATGCCAACAAGCAGCTGGCGGGGTTGGTGGCCAACTACTACACCCCTCGCTGGCGGCT
TTTCCTGGAGGCGCTGGTTGACAGTGTGGCCCAGGGCATCCCTTTCCAACAGCACCAGTTTGACAAAAAT
GTCTTCCAACTGGAGCAGGCCTTCGTTCTCAGCAAGCAGAGGTACCCCAGCCAGCCGCGAGGAGACACTG
TGGACCTGGCCAAGAAGATCTTCCTCAAATATTACCCCCGCTGGGTGGCCGGCTCTTGGTGA(SEQ ID
NO: 4)

Nucleotide sequence of pXD671 (SEQ ID NO: 5):
GAATTCTCGAGTCGAGATCCCCCGGGCTGCAGGAATTCGAGGCTGCAGTGCCCCAGATCACACTACTGC
ACTCCAGCCTGGGTGATAAAGTGAGACCTTCTCAATAAATAAATACAAAATTAAAAACCAGCACTT
AACTCTTCAGCTACCACATTAATTCTCAGCAAATACCTTCTTAGCAGTCGTTTGACAATCAAGTCAACTA
GAACTGGAACTAGAATGAGATAACATGGTATTGCTTCTTCTCACAGAGTAGATCCTCAATGAATGTTTGA
AAGGAGATGTCAGTCCGATGTTTACCTTTGATCAAAGAAAGGAATATAAGATTAAGACATCAGGGCCTCG
TCAGGCTGTTCTGCATTTCTGTATTAGCCAGACTCTCAACCATTTTCTTGCCATATATAAACATGTGGCC
CAGTTTGTAATCAGTGGGTTATAGGAAGCTAAAGAAATTATCTTTTCTTTCATAGAAAATAATTTGGCA
TAGGAACCCAGGTATTAACCGTCTAGCACCAAAGTTGTAGGAATCTTTAGTCTCCTCTGCCTCCCTTCTT
CCATCCCTCTACTCTCAGTCTTGACCCCACCCCACCCCTTACTTGTTTTTCCTTCTACTCATTTTCTCCT
CCCTCCCTCTCCCTCTCCCCACACTAGAACCATCAGGGCCCTCACCAGGGCATTCAGTTCAGGTTCTGG
GTCAGCTCTCACAGCTCTACCAGTCCCACCCCCATCCCCAGGAAAACTGCTCCTTATTTGGAGTCACAA
AAATATTTAACAGAGATCTAACTGACCACTAAAAATTCCTCCTTTAAAACAAACACCTAACTCAACTATTT
TCCCCCAAGTTATATGGAAAACAGCTGCAATTAGAACTTGATTCTCACTTTAAGAAAGAAAGATTCTTG
TTTGGTTTTCTCCACTTTCATTTTTTGTTTCTAGGTCCAGGGCCTCCCACCCAAATGCTGACGGCTGCCTG
CTTCAAACCCTGCCACATCAGCAGGGAGGGAGCACAGCGGCATTTGGTATTTGCATCAGTTTCCAGGAAT
GCTTTTCAAGTTATCAGTTCACTCTGCTGCCTTTAGCAGAGACGTTTTCCCTCTAAGTTTATAGATGTCT
GCTTCAATTTACAGTCCTCTAATTCTCAAAAACTTGCTGAGGATTTTTCTTTTTTGGCTAAAAGAGAAAT
TATAATCACACTTCTAAAAACATTCTATGTTTTAAACTATTTTGACAACAACAACAAAACCTACAATGAA
```

SEQUENCE LISTING

```
ATGTTTAAAACTTGGGATATCTATTGCAAATCCAATGATTGAGCCAACTTGACCCCAGAAGCGTTATCAG
ATAACCTCACTGAAGGGTATTTGGAGGGTTTCTTTCATAAATCTGTTGCATTACCACCCTGAGTCATTTT
GCTCAGAATTAGTCTCTGACTCTCAGCAACACAGGACAAATACACACATATGCCCTGCAAAGGTAATTCA
GCACAGTGGTAACAATGATTCTTAGAAATCATTTCTCACTCTTCTGATATGCAGAAAAAAATTTGTTATG
ATGTAGTATTGAAGTTTTTCTTTCCTGATAAAAATGATTTCCACTTTAAAAGTTTTTTGTTAGTTCTGTA
ACGGTGATATTTCAGGGAAATGTTAAAAATGTTCTTGGAATATACAATTCAACCTCAGGTCTTTTGTTGT
TGTTGTTCCTAGAACCTAGAAAACTTCAAACATTGTTGCCTAGTTAGAAAAAAAATTTGAATGTGGATTGC
TCCCTGTAAACCCCCTTCTAGGAATGACCAGTAACCCTTTCAAATTCTTTCACTCCCAGTTACTTCAAAA
AATCATCCAAAGTGGTCTCCCAAGTGAGTGCCTTTAATTAGAATAAAACAAGAGTTTATTATAGTTTTTG
GTTATCCACTTTTACTTGCATTAACCTTTTTTTCTTCTTTTACATTTAGAAAGAGTAACCTGCTTTAGAA
TAGTCCCTTTTATTTACAGAAGCTGCTGATGGAGTTAACTTCTGCAGAAATTCTTCCTTAAGGCAAAGCA
AAAAAAGCGGGGAGGGGGTGGGGGAAGGAAGGGAAAAAGATTCTCAGGGAACTACAGCCCACTTGCTTC
TGTTTCTTAGAGACAGAACTGACCTAAAGATGCCCCCTTTGCGATGACTTCTGGGATAGAGCAGCACTCT
AACTAGGCCCCGCTGCCTCATGGGGACCTTAGGCAAGTAGAGGAGAGGCCTGACACACACACACACACA
CACACACACACACGCACACGCGCGCGCACACACACACACACAGCCTTTCAAACCTAGGGCCTGGAA
TGCCATCCCAAGAGGCTTTAGAAAAAGGCACAGGACCTTTGGCCTCCCACCTCAGGGTCAAAGTACCAGT
TCCTCCTCTCCCTAGTAGGGAGTGGAGGGTTGGATGGAGGCGGCCAGAGAAGAGGGAAGTTGGGTGCTGG
GGAGAGAGTTAACATCCACGTTGGTGGGCGCACTGCTTGGGGTGTTACCAGCGAAGACTACGAAGACCCC
AAGCTCGAATCAGAAGGGCCTCTGGATGTGCTAGGGGAGGTGCTTGGGTGTGGCTGTAAGAGATGGGACA
GAGAGTAAGCAGCAAGGTCAAGAGGGACCGGGGGGCTCACGGGAGGGTTGAAGGGTCCAGGCTCAGGGTA
GAACTGGTAAATCCAGACAAGGAGCCCATGGAGAAGGGGAGGGGAGACTGGAAACCATGAAAGATCCCCC
ACCGCAGCCTCAGAAAGGAGAGACTGAGAAATAAGTTCTCGGTCTCCAGGTCGGTTGGAGTCGTGTCGGA
GTGCCAGACCATCCCCAAAAGACCCTCTTTGGAATGAGCCTCAGCAAAGGCAAGCTAGGAGGTCGAAGG
ACTTCCCCAGGTGACTCGGTCTAGTCTAGAGTTCGCAAAGCCTATCCTCCCTGTAGCCGGGTGCCAAGCA
GCCTCGAGCCTGCTCCCCAGCCCACCTGCCAACAAAAGGCGCCCTCCGACTGCAACCCAGCCCTCCACAG
ACAGGACCCGCCCTTTCCCGAAGTCATAAGACAAAGAGAGTGCATCACTGCTGAAACAGTGGGCGCACAC
GAGCCCCAAAGCTAGAGAAAAGCTGGACGGGGCTGGGGGCGGGTGCAGGGGTGGAGGGGCGGGAGGCG
GGCTCCGGCTGCGCCACGCTATCGAGTCTTCCCTCCCTCCTTCTCTGCCCCCTCCGCTCCCGCTGGAGCC
CTCCACCCTACAAGTGGCCTACAGGGCACAGGTGAGGCGGGACTGGACAGCTCCTGCTTTGATCGCCGGA
GATCTGCAAATTCTGCCCATGTCGGGCTGCAGAGCACTCCGACGTGTCCCATAGTGTTTCCAAACTTGGA
AAGGGCGGGGAGGGCGGGAGGATGCGGAGGGCGGAGGTATGCAGACAACGAGTCAGAGTTTCCCCTTGA
AAGCCTCAAAAGTGTCCACGTCCTCAAAAAGAATGGAACCAATTTTAAGCACCAGCCCCGTGGCCACGTC
CCTACCGGGTTGGTACCGAGCTCAATAATGACGTATGTTCCCATAGTAACGCCAATAGGGACTTTCCATT
GACGTCAATGGGTGGAGTATTTACGGTAAACTGCCCACTTGGCAGTACATCAAGTGTATCATATGCCAAG
TACGCCCCCTATTGACGTCAATGACGGTAAATGGCCCGCCTGGCATTATGCCCAGTACATGACCTTATGG
GACTTTCCTACTTGGCAGTACATCTACGTATTAGTCATCGCTATTACCATGGTGATGCGGTTTTGGCAGT
ACATCAATGGGCGTGGATAGCGGTTTGACTCACGGGGATTTCCAAGTCTCCACCCCATTGACGTCAATGG
GAGTTTGTTTTGGGTACCAACCCGGTATTCGCTCCCTCCTCTGCGCCCCCGCAGGCTCCTCCCAGCTGTG
GCTGCCCGGCCCCCAGCCCCAGCCCTCCCATTGGTGGAGGCCCTTTTGGAGGCACCCTAGGGCCAGGGA
AACTTTTTGCCGTATAAATAGGGCAGATCCGGGCTTTATTATTTTAGCACCACGGCAGCAGGAGGTTTCGG
CTAAGTTGGAGGTACTGGCCACGACTGCATTCCCGCGCCCGCCATTTGATACCTCCGCCGGTGACCCAGG
GCTCTGCGACACAAGGAGTCGCATTTCTAAGTGCTAGACAAAAGGCCGGCGCCGCCTTCCGCTGCCCGC
CTCCTGCGCCGCCCCTTCCGAGGCTAAATCGGCTGCGTTCCTCTCGGAACGCGCCGCAGAAGGGGTCCTG
GTGACGAGTCCCGCGTTCTCTCCTTGAATCCACTCGCCAGCCCGCCGCCCTCTGCCGCCGCACCCTGCAC
ACCCGCCCTCTCCTGTGCCAGGTGAGCGCCCCTCTTCACGTGCGGGATCCTAAGAGGCAGGGACCGTGGAGAGGGAT
CTTGGGGGCAGTGGCGGGTTGGGCGTCCGCGTGGAGGCCTCCCCCATCCCATGCCAGCGTCTCCCCACTA
CCAGGCACACACAGGCTCCCCGGCCCCTCCAGCCTGAGGTCCTCTAACTGCGCAATGCAGCGGCTGCGCG
CGCTGAGTCATGGCGGGGAGGAAGCCGGACGAGATGAAGGACCATTCTCCCCCTTTTCTTGCAGGGACC
CCTGTGGCAAAGGATTAGGGCCCCTTAGCCCTGGCGGGGATCCTAAGAGGCATGAGGGGTGGGGGCCGG
CCCATGTACAGCCCCAGGGTTCTCGCAAGTGGGAGCTTGGTTTCTGTCCTGGGAAACGGGGCGCCCTTCG
CGAGGAGGGAAACCCCTCCGCGGTGCTTGATGCCCCCTTAACACTTTCCCTGTCTCCTTATCGGGCGA
CCTTGATTCTGAGCCCGGAACAGCTGCAGCCATGCGAAGCGACGGGAGCATTTTTCAGGGGAAGGCGCTT
GCTCCTCCACGTTCTTGCCCCGTAGGAACAGTGACGATGGCAAAGCTTACCGCTTTCCTCGCCTCGGGCT
AGGGCTTGTTCCGCCGCCCTTTCCTGGGCTTCTCCTTGCTCTCTTTATATTTTTCCTAATGCCCCTTTCCT
ACCACCCGCCCCCTCCCTTGTGGGGAAAAGCCTGACCTTGGGATGTCCTTGAAGCCTTGGAGCCCGGGCC
AGCCCTGGGATCTTGAGGGGATTGAAGGAACACCCCAGTGGCAGTCAGAAGAGCTGGGTTCTAATCTCA
GATCTGGCTCCGGGGTTGCTGTGTGGCTTGAAGCACAGACCTTTCCCATATCTGGGCCCTTTCCCACGAG
GGTGTTGGGCCCTCTGCTTGATTCACGATCTTTACATTCTAAAATACTCCGGTTCGGTTTTGTTTTCAGG
CAAGGTGACCCCATGGCAAGCGCAAGCCAGAAGGGTCCAGCTTCAACATGACCCACCTGTCCATGGCTA
TGGCCTTTTCCTTTCCCCCAGTTGCCAGTGGGCAACTCCACCCTCAGCTGGGCAACACCCAGCACCAGAC
AGAGTTAGGAAAGGTACAGGGGCAGGCCTAGCAAAGGGAAGTTGGGCGTAAGAGAGAGCTGGGGACCAGA
AGTGCCCCAGGGCCTGCTGGGTGTGGGCAGGGGAGGTAGGGAACATTTCCCTGACCTCCAGGAGAGGGG
CCCTGGTCATCGGGAGATGATGGGAAACCCTAGCTAACTAGTCCTTCCCCTCTGTTTCCTGTATCCAGGA
ACTTGCTACTACCAGCACCGTCGCTAGCACGCGTTTAATTAAGTTTAAACGGTGGCATCCCTGTGACCC
CTCCCCAGTGCCTCTCCTGGCCCTGGAAGTTGCCACTCCAGTGCCCACCAGCCTTGTCCTAATAAAATTA
AGTTGCATCATTTTGTCTGACTAGGTGTCCTTCTATAATATTATGGGGTGAGGGGGGTGGTATGGAGCA
AGGGGCAAGTTGGGAAGACAACCTGTAGGGCCTGCGGGGTCTATTGGGAACCAAGCTGGAGTGCAGTGGC
ACAATCTTGGCTCACTGCAATCTCCGCCTCCTGGGTTCAAGCGATTCTCCTGCCTCAGCCTCCCGAGTTG
TTGGGATTCCAGGCATGCATGACTGCAGGAATTCGATATCAAGCTTATCGATAAGAGCTTGGCTGTGGAA
TGTGTGTCAGTTAGGGTGTGGAAAGTCCCCAGGCTCCCCAGCAGGCAGAAGTATGCAAAGCATGCATCTC
AATTAGTCAGCAACCAGGTGTGGAAAGTCCCCAGGCTCCCCAGCAGGCAGAAGTATGCAAAGCATGCATC
TCAATTAGTCAGCAACCATAGTCCCGCCCCTAACTCCGCCCATCCCGCCCCTAACTCCGCCCAGTTCCGC
CCATTCTCCGCCCCATGGCTGACTGATTTTTTTTATTTATGCAGAGGCCGAGGCCGCCTCGGCCTCTGAG
CTATTCCAGAAGTAGTGAGGAGGCTTTTTTGGAGGCCTAGGCTTTTGCAAAAAGCTCCTCGAGGAACTGA
AAAACCAGAAAGTTAACTGGTAAGTTTAGTCTTTTTGTCTTTTATTTCAGGTCCCGGATCTGATCAAGAG
ACAGGATGAGGATCGTTTCGCATGATTGAACAAGATGGATTGCACGCAGGTTCTCCGGCCGCTTGGGTGG
AGAGGCTATTCGGCTATGACTGGGCACAACAGACAATCGGCTGCTCTGATGCCGCCGTGTTCCGGCTGTC
```

SEQUENCE LISTING

```
AGCGCAGGGGCGCCCGGTTCTTTTTGTCAAGACCGACCTGTCCGGTGCCCTGAATGAACTGCAGGACGAG
GCAGCGCGGCTATCGTGGCTGGCCACGACGGGCGTTCCTTGCGCAGCTGTGCTCGACGTTGTCACTGAAG
CGGGAAGGGACTGGCTGCTATTGGGCGAAGTGCCGGGGCAGGATCTCCTGTCATCTCACCTTGCTCCTGC
CGAGAAAGTATCCATCATGGCTGATGCAATGCGGCGGCTGCATACGCTTGATCCGGCTACCTGCCCATTC
GACCACCAAGCGAAACATCGCATCGAGCGAGCACGTACTCGGATGGAAGCCGGTCTTGTCGATCAGGATG
ATCTGGACGAAGAGCATCAGGGGCTCGCGCCAGCCGAACTGTTCGCCAGGCTCAAGGCGCGCATGCCCGA
CGGCGAGGATCTCGTCGTGACCCATGGCGATGCCTGCTTGCCGAATATCATGGTGGAAAATGGCCGCTTT
TCTGGATTCATCGACTGTGGCCGGCTGGGTGTGGCGGACCGCTATCAGGACATAGCGTTGGCTACCCGTG
ATATTGCTGAAGAGCTTGGCGGCGAATGGGCTGACCGCTTCCTCGTGCTTTACGGTATCGCCGCTCCCGA
TTCGCAGCGCATCGCCTTCTATCGCCTTCTTGACGAGTTCTTCTGAGCGGGACTCTGGGGTTCGAAATGA
CCGACCAAGCGACGCCCAACCTGCCATCACGAGATTTCGATTCCACCGCCGCCTTCTATGAAAGGTTGGG
CTTCGGAATCGTTTTCCGGGACGCCGGCTGGATGATCCTCCAGCGCGGGATCTCATGCTGGAGTTCTTC
GCCCACCCCGGGCTCGATCCCCTCGCGAGTTGGTTCAGCTGCTGCCTGAGGCTGGACGACCTCGCGAGT
TCTACCGGCAGTGCAAATCCGTCGGCATCCAGGAAACCAGCAGCGGCTATCCGCGCATCCATGCCCCGA
ACTGCAGGAGTGGGGAGGCACGATGGCCGCTTTGGTCCCGGATCCAGACATGATAAGATACATTGATGAG
TTTGGACAAACCACAACTAGAATGCAGTGAAAAAAATGCTTTATTTGTGAAATTTGTGATGCTATTGCTT
TATTTGTAACCATTATAAGCTGCAATAAACAAGTTAACAACAACAATTGCATTCATTTTATGTTTCAGGT
TCAGGGGGAGGTGTGGGAGGTTTTTTAAAGCAAGTAAAACCTCTACAAATGTGGTATGGCTGATTATGAT
CCGGCTGCCTCGCGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGGTGTTGGCGGGTGT
CGGGGCGCAGCCATGACCCAGTCACGTAGCGATAGCGGAGTGCGGCCgcAAGGATCTAAAGCCAGCAAAA
GTCCCATGGTCTTATAAAAATGCATAGCTTTAGGAGGGGAGCAGAGAACTTGAAAGCATCTTCCTGTTAG
TCTTTCTTCTCGTAGACTTCAAACTTATACTTGATGCCTTTTTCCTCCTGGACCTCAGAGAGGACGCCTG
GGTATTCTGGGAGAAGTTTATATTTCCCCAAATCAATTTCTGGGAAAAACGTGTCACTTTCAAATTCCTG
CATGATCCTTGTCACAAAGAGTCTGAGGTGGCCTGGTTGATTCATGGCTTCCTGGTAAACAGAACTGCCT
CCGACTATCCAAACCATGTCTACTTTACTTGCCAATTCCGGTTGTTCAATAAGTCTTAAGGCATCATCCA
AACTTTTGGCAAGAAAATGAGCTCCTCGTGGTGGTTCTTTGAGTTCTCTACTGAGAACTATATTAATTCT
GTCCTTTAAAGGTCGATTCTTCTCAGGAATGGAGAACCAGGTTTTCCTACCCATAATCACCAGATTCTGT
TTACCTTCCACTGAAGAGGTTGTGGTCATTCTTTGGAAGTACTTGAACTCGTTCCTGAGCGGAGGCCAGG
GTAGGTCTCCGTTCTTGCCAATCCCCATATTTTGGGACACGGCGACGATGCAGTTCAATGGTCGAACCAT
GATGGCAGCGGGGATAAAATCCTCTTATCGCGATAAGCTTTTTGCAAAAGCCTAGGCCTCCAAAAAAGCC
TCCTCACTACTTCTGGAATAGCTCAGAGGCCGAGGCGGCCTCGGCCTCTGCATAAATAAAAAAAATTAGT
CAGCCATGGGGCGGAGAATGGGCGGAACTGGGCGGAGTTAGGGGCGGGATGGGCGGAGTTAGGGGCGGGA
CTATGGTTGCTGACTAATTGAGATGCATGCTTTGCATACTTCTGCCTGCTGGGGAGCCTGGGGACTTTCC
ACACCTGGTTGCTGACTAATTGAGATGCATGCTTTGCATACTTCTGCCTGCTGGGGAGCCTGGGGACTTT
CCACACCCTAACTGACACACATTCCACAGCTGGTTCTTTCCGCCTCAGAAGGTACCTAACCAAGTTCCTC
TTTCAGAGGTTATTTCAGGCCATGGTGCTGCGCCGAATTCATCGATACCGTCGATCCGAACAAACGACCC
AACACCCGTGCGTTTTATTCTGTCTTTTTATTGCCGCGGCCGCTCGACCTCGAGGGGGGGCCCGGTACCC
AGCTTTTGTTCCCTTTAGTGAGGGTTAATTGCGCGCTTGGCGTAATCATGGTCATAGCTGTTTCCTGTGT
GAAATTGTTATCCGCTCACAATTCCACACAACATACGAGCCGGAAGCATAAAGTGTAAAGCCTGGGGTGC
CTAATGAGTGAGCTAACTCACATTAATTGCGTTGCGCTCACTGCCCGCTTTCCAGTCGGGAAACCTGTCG
TGCCAGCTGCATTAATGAATCGGCCAACGCGCGGGGAGAGGCGGTTTGCGTATTGGGCGCTCTTCCGCTT
CCTCGCTCACTGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCATCACAAAA
ATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGA
AGCGTGGCGCTTTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTTGAGTCCAA
CCCGGTAAGACACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGAACAGTATTTGGTATCT
GCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCT
TTGATCTTTTCTACGGGGTCTGACGCTCAGTGGAACGAAAACTCACGTTAAGGGATTTTGGTCATGAGAT
TATCAAAAAGGATCTTCACCTAGATCCTTTTAAATTAAAAATGAAGTTTTAAATCAATCTAAAGTATATA
TGAGTAAACTTGGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTGTCAGAAGTAAGTTGGCCGCA
GTGTTATCACTCATGGTTATGGCAGCACTGCATAATTCTCTTACTGTCATGCCATCCGTAAGATGCTTTT
CTGTGACTGGTGAGTACTCAACCAAGTCATTCTGAGAATAGTGTATGCGGCGACCGAGTTGCTCTTGCCC
GGCGTCAATACGGGATAATACCGCGCCACATAGCAGAACTTTAAAGTGCTCATCATTGGAAAACGTTCT
TCGGGGCGAAAACTCTCAAGGATCTTACCGCTGTTGAGATCCAGTTCGATGTAACCCACTCGTGCACCCA
ACTGATCTTCAGCATCTTTTACTTTCACCAGCGTTTCTGGGTGAGCAAAAACAGGAAGGCAAATGCCGC
AAAAAAGGGAATAAGGGCGACACGGAAATGTTGAATATTCATCTCTTCCTTTTTCAATATTATTGAAGC
ATTTATCAGGGTTATTGTCTCATGAGCGGATACATATTTGAATGTATTTAGAAAAATAAACAAATAGGGG
TTCCGCGCACATTTCCCCGAAAAGTGCCACCTGACGTCTAAGAAACCATTATTATCATGACATTAACCTA
TAAAAATAGGCGTATCACGAGGCCCTTTCGTCTCGCGCGTTTCGGTGATGACGGTGAAAACCTCTGACAC
ATGCAGCTCCCGGAGACGGTCACAGCTTGTCTGTAAGCGGATGCCGGGAGCAGACAAGCCCGTCAGGGCG
CGTCAGCGGGTGTTGGCGGGTGTCGGGGCTGGCTTAACTATGCGGCATCAGAGCAGATTGTACTGAGAGT
GCACCATATGCGGTGTGAAATACCGCACAGATGCGTAAGGAGAAAATACCGCATCAGGCGCCATTCGCCA
```

```
TTCAGGCTGCGCAACTGTTGGGAAGGGCGATCGGTGCGGGCCTCTTCGCTATTACGCCAGCTGGCGAAAG
GGGGATGTGCTGCAAGGCGATTAAGTTGGGTAACGCCAGGGTTTTCCCAGTCACGACGTTGTAAAACGAC
GGCCAGT (SEQ ID NO: 5)
```

Conseusus sequence of CpGH89 amino acid sequence of Clostridium perfringens and wild-type human NAGLU amino acid sequence (SEO ID NO: 6):

(SEQ ID NO: 6)

```
GVEITEGVTVTAKGNTEGNTADLAIDGDLSTYWESSNDYKWIEVDLGGIYE
LSKIEIFNKDEAVYKYNIYASEDGENFNKIAYKNNDNVSDSNGNMHTIDNV
RAGKIRIDVVQNSNSDRVNIAEINVFGKNTGESLPEMEAXATAAASETLLA
AEAEGAAGDEARAAAATRAEXARLIGRGIAAXFKDKFERAIAAQLNGNDTX
ELGDGGAARVRXRGNNGVAAAAGLNRYLRXXCNCSHNAIMGSXLRXPRPXP
AVGERLTEATPNRHRYAQNFCTQSYSMSFWDWARWEREIDWCAXNGXNLAL
AIIGQEAXLRRTLNALGLSXAEXNEFISGPAXLAWGRMQNXHGFDGPLPND
WHEQRAELQRRMHDRMRSFGINPVLQAXAGHVPRAFKRKNQXAXTIKQGGW
```

-continued

```
CGFXRPDMCKSXLNAGEADIFQIXADLFLREQIEEFGDIDNIYGADPFNEG
QNPGDEDNYLAAATEAXQXAMIAHDNXAVWLIQNWQFQHQPQFWGNAQNRA
LEGATKRDRAXVLDLFAESQPDWNRLAEFRDQPFIWNMLHNFGGRHGXDAA
LEALAGEIEAARLANNEHMVGIGIAPEAINQNELAYELXAXXAWRRDQXPX
LAAWTEDXAARRYGKSNKXAGAAWRIILRSAYNCRNXACRGAARSIINARP
GLQINSASTWGHSKIWYXRSXFEEAIRILAKNADELADSDAFRYDLADILR
QALAXLAQEYYEEARNAYNNGXGAKLLRAGGKLAYELIKAQXRVLASRPRF
LIGNWIEXARAAAKDEAXWTADLXEQNARAQLTLWGPRNNADGGGILDYAN
RQLAGLTAXYYTARWRLFIXALQAELAQGAKAQXHXFDKNEXXLEXAKSDS
DQRYPSXARNXNLDEAAKIAXESYPGTNADKILGENES
```

What is claimed is:

1. A method of obtaining a purified recombinant a-N-acetylglucosaminidase (NAGLU) polypeptide with an altered glycosylation pattern compared to native NAGLU, the method comprising:
   a) expressing a recombinant NAGLU polypeptide in a host cell,
   b) treating the host cell with a glycosidase inhibitor, and
   c) purifying the recombinant NAGLU polypeptide in a solution to obtain a purified recombinant NAGLU polypeptide with an altered glycosylation pattern compared to native NAGLU;
   wherein the recombinant NAGLU polypeptide is at least 90% identical to the amino acid sequence set forth in SEQ ID NO: 1 or 3; and
   wherein the recombinant NAGLU polypeptide comprises one or more glycans at each of the following asparagine (N) residues: N261, N272, N435, N503, N526, and N532 corresponding to SEP ID NO: 1 or 3.

2. The method of claim 1, wherein the glycosidase inhibitor is a mannosidase I inhibitor.

3. The method of claim 2, wherein the mannosidase I inhibitor is kifunensine.

4. The method of claim 1, wherein the recombinant NAGLU polypeptide is expressed in mammalian cells.

5. The method of claim 1, wherein the recombinant NAGLU polypeptide comprises the amino acid sequence set forth in SEQ ID NO: 3.

6. The method of claim 1, wherein the recombinant NAGLU polypeptide comprises one or more amino acid substitutions, deletions, or additions as set forth in Table 4 compared to wild-type human NAGLU polypeptide.

7. The method of claim 1 further comprising crystallizing the recombinant NAGLU polypeptide from a solution with:
   a pH ranging from about 6.5 to about 9.0;
   a precipitant selected from the group consisting of $Li_2SO_4$, monomethyl ether (MME), polyethylene glycol (PEG), 2-methyl-2,4-pentanediol (MPD), and combinations thereof; and
   optionally a salt selected from the group consisting of $ZnSO_4$, $Zn(OAc)_2$, NaCl, $(NH_4)_2SO_4$, $NiCl_2$, and combinations thereof, wherein the recombinant NAGLU polypeptide is identical to the amino acid of SEQ ID NO: 1 or 3.

8. The method of claim 7, wherein the crystallized NAGLU is characterized with space group P6₃ and has unit cell parameters of a=b=205.66 Å, c=78.69 Å, a=b=207.5 Å, c=79.6 Å, or a=b=205.13 Å, c=78.44 Å and bond angles of α=β=90°, γ=120°.

9. The method of claim 7, comprising crystallizing the recombinant NAGLU polypeptide by concentrating a solution of the purified recombinant NAGLU polypeptide to a polypeptide concentration at which the NAGLU polypeptide precipitates and forms crystals.

10. The method of claim 9, wherein the recombinant NAGLU polypeptide concentration in solution at which the NAGLU polypeptide precipitates and forms crystals is about 1 mg/ml.

11. The method of claim 7, wherein the solution has a pH of 8.5 and comprises $Li_2SO_4$ and $NiCl_2$.

12. The method of claim 1, wherein the recombinant NAGLU polypeptide is a mutant recombinant NAGLU.

13. The method of claim 12, wherein the recombinant mutant NAGLU polypeptide is a-N-acetylglucosaminidase-kifunensine (NAGLU-kif).

14. The method of claim 1, wherein the recombinant NAGLU polypeptide comprises an amino acid sequence having at least 98% amino acid sequence identity to the amino acid sequence set forth in SEQ ID NO: 3.

15. The method of claim 1, wherein the recombinant NAGLU polypeptide comprises one or more sites of amino acid substitutions, deletions or duplications associated with Mucopolysaccharidosis type III-B (MPS III-B).

16. The method of claim 1, wherein the recombinant NAGLU polypeptide comprises at least one N-acetylglucosamine molecule each on N261, N503, N526 and N532, and at least two N-acetylglucosamine molecules each on N272 and N435.

17. The method of claim 1, wherein the recombinant NAGLU polypeptide is expressed in HT1080 cells.

18. The method of claim 1, wherein the recombinant NAGLU polypeptide is secreted from mammalian cells.

19. The method of claim 1, wherein purifying the recombinant NAGLU polypeptide comprises using column purification.

20. The method of claim 1, wherein the recombinant NAGLU polypeptide comprises the amino acid sequence set forth in SEQ ID NO: 1.

* * * * *

UNITED STATES PATENT AND TRADEMARK OFFICE
CERTIFICATE OF CORRECTION

PATENT NO. : 9,708,590 B2  
APPLICATION NO. : 14/120882  
DATED : July 18, 2017  
INVENTOR(S) : Muthuraman Meiyappan et al.

It is certified that error appears in the above-identified patent and that said Letters Patent is hereby corrected as shown below:

In the Claims

In Claim 1, at Column 109, Line 65, the text: "SEP ID NO: 1 or 3" should be replaced with the text: --SEQ ID NO: 1 or 3--.

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*